United States Patent
Halby et al.

(10) Patent No.: US 10,450,299 B2
(45) Date of Patent: Oct. 22, 2019

(54) SUBSTITUTED QUINAZOLINE DERIVATIVES AS DNA METHYLTRANSFERASE INHIBITORS

(71) Applicants: Pierre Fabre Medicament, Boulogne-Billancourt (FR); Centre National de la Recherche Scientifique (CNRS), Paris (FR); Sapienza Universita di Roma, Rome (IT)

(72) Inventors: Ludovic Halby, Toulouse (FR); Paola Arimondo, Toulouse (FR); Antonello Mai, Rome (IT); Dante Rotili, Rome (IT)

(73) Assignees: Centre National de la Recherche Scientifique (CNRS), Paris (FR); Pierre Fabre Medicament, Boulogne-Billancourt (FR); Sapienza Universita di Roma, Rome (IT)

( * ) Notice: Subject to any disclaimer, the term of this patent is extended or adjusted under 35 U.S.C. 154(b) by 0 days.

(21) Appl. No.: 15/560,883

(22) PCT Filed: Mar. 25, 2016

(86) PCT No.: PCT/EP2016/056734
§ 371 (c)(1),
(2) Date: Sep. 22, 2017

(87) PCT Pub. No.: WO2016/151144
PCT Pub. Date: Sep. 29, 2016

(65) Prior Publication Data
US 2018/0118717 A1    May 3, 2018

(30) Foreign Application Priority Data
Mar. 25, 2015 (EP) .................... 15305431

(51) Int. Cl.
A61K 31/517 (2006.01)
C07D 401/14 (2006.01)
A61P 35/00 (2006.01)

(52) U.S. Cl.
CPC ............ C07D 401/14 (2013.01); A61P 35/00 (2018.01)

(58) Field of Classification Search
CPC .................. A61K 31/517; C07D 401/14
See application file for complete search history.

(56) References Cited

FOREIGN PATENT DOCUMENTS

| EP | 0602851 A1 | 6/1994 |
|---|---|---|
| WO | 2008/020302 A2 | 2/2008 |
| WO | 2015/040169 A1 | 3/2015 |

OTHER PUBLICATIONS

Elslager, E.F. et al., Folate Antagonists 16. Antimalarial and Antibacterial Effects of 2,4-Diamino-6[(heterocyclic)thio, sulfinyl, and sulfonyl]quinazolines (1-3), Journal of Heterocyclic Chemistry, Jan. 1, 1980, vol. 17, No. 1, pp. 129-136.
Srimongkolpithak, N., Identification of 2,4-diamino-6,7-dimethoxyquinoline derivatives as G9a inhibitors, MedChemComm, Aug. 26, 2014, vol. 5, No. 12, pp. 1821-1828.
Thurmond, J. et al., Synthesis and Biological Evaluation of Novel 2,4-Diaminoquinazoline Derivatives as SMN2 Promoter Activators for the Potential Treatment of Spinal Muscular Atrophy, Journal of Medicinal Chemistry, Feb. 1, 2008, vol. 51, No. 3, pp. 449-469.
Vedadi, M. et al., A Chemical Probe Selectively Inhibits G9a and GLP Methyltransferase Activity in Cells, Nature Chemical Biology, Aug. 1, 2011, vol. 7, No. 8, pp. 566-574.

*Primary Examiner* — Brenda L Coleman
(74) *Attorney, Agent, or Firm* — Banner & Witcoff, Ltd.

(57) ABSTRACT

The present invention relates to compounds of the following formula (I) and pharmaceutically acceptable salts and solvates thereof, their methods of preparation, their use as a drug, notably in the treatment of cancer, and pharmaceutical compositions containing such compounds.

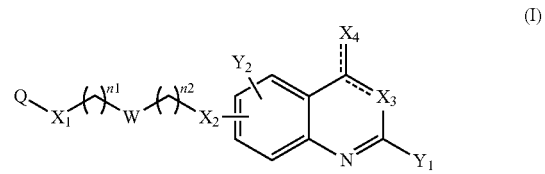

18 Claims, No Drawings
Specification includes a Sequence Listing.

SUBSTITUTED QUINAZOLINE DERIVATIVES AS DNA METHYLTRANSFERASE INHIBITORS

RELATED APPLICATION DATA

This application is a National Stage Application under 35 U.S.C. 371 of co-pending PCT application number PCT/EP2016/056734 designating the United States and filed Mar. 25, 2016; which claims the benefit of EP application number 15305431.7 and filed Mar. 25, 2015 each of which are hereby incorporated by reference in their entireties.

The present invention relates to substituted quinazoline derivatives useful as DNA methyltransferase (DNMT) inhibitors, notably in the treatment of cancer.

Gene expression is modulated by epigenetic modifications. Methylation of deoxycytidines (dC) in the DNA was shown to play a key role in epigenetic regulation in mammals (Berger et al. *Genes Dev.* 2009, 23, 781; Kelly et al. *Biotechnol.* 2010, 28, 1069). It is the most stable epigenetic mark and occurs at CpG sites, which are regrouped in island and essentially located in promoters, repeated sequences and CpG island shores (Gros et al. *Biochimie* 2012, 94, 2280). Hypermethylation of promoters' CpG islands induces gene silencing while hypomethylation induces gene expression (Sharma et al. *Carcinogenesis* 2010, 31, 27; Esteller *N. Engl. J. Med.* 2008, 358, 1148).

The enzymes responsible for DNA methylation are DNA methyltransferases (DNMTs). Two families of catalytically active DNMTs have been identified: DNMT1, responsible for DNA methylation maintenance during replication, and DNMT3A and 3B, responsible for de novo DNA methylation. DNMTs add a methyl group on the carbon-5 position of the deoxycytosine at the CpG site in the DNA by using S-adenosyl-L-methionine (AdoMet) as methyl donor (Jurkowska et al. *ChemBioChem* 2011, 12, 206).

Alteration of DNA methylation patterns lead to various diseases such as cancer (Baylin and Jones *Nat. Rev. Cancer* 2011, 11, 726). Cancerous cells often present aberrant DNA methylation, in particular a specific hypermethylation of tumour suppressor genes is observed. Restoring their expression by specific inhibition of DNA methylation represents an attractive therapeutic strategy (Fahy et al. *Expert Opin. Ther. Pat.* 2012, 22, 1427; Ahuja et al. *J. Clin. Invest.* 2014, 124, 56-63).

DNMT inhibitors can be divided into two families: nucleoside analogues and non-nucleosides. The first are the most active ones. Two of them were FDA approved: 5-azacytidine (Vidaza®) and 5-azadeoxycytidine (Dacogene®) (Gros et al. *Biochimie* 2012, 94, 2280). Despite their high efficiency, their poor bioavailability, their instability in physiologic media and their little selectivity restrict their use (Erdmann et al. *J. Med. Chem.* Article ASAP, DOI: 10.1021/jm500843d, Publication Date (Web): Nov. 19, 2014). Non-nucleoside analogues present various structures and mechanisms of action. Many of them were shown to target the catalytic site but suffer from high toxicity, lack of specificity and weak activity.

There exists thus a need for novel DNMT inhibitors.

The inventors of the present invention have thus discovered that substituted quinazoline derivatives can be used as DNA methyltransferase (DNMT) inhibitors.

The present invention concerns thus a compound of the following formula (I):

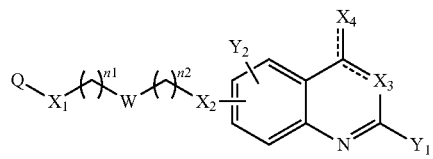

or a pharmaceutically acceptable salt or solvate thereof, wherein:
- ══ represents a single bond or a double bond on the condition that the two bonds ══ do not represent a double bond at the same time,
- n1 and n2 represent, independently of each other, an integer comprised between 0 and 8, notably between 1 and 8,
- Q represents an optionally substituted aryl or an optionally substituted nitrogen-containing heterocycle,
- W represents a bond, a divalent monoglycosyl, $NR_0$, a piperidinediyl, a piperazinediyl or a pyrrolidinediyl, and preferably a divalent monoglycosyl, $NR_0$, a piperidinediyl, a piperazinediyl or a pyrrolidinediyl,
- $X_1$ represents O or $NR_1$,
- $X_2$ represents O, $NR_2$ or a bond,
- $X_3$ represents:
  - N when ══ $X_3$ represents a double bond ═$X_3$, and
  - $NR_3$ when ══ $X_3$ represents a single bond —$X_3$,
- $X_4$ represents:
  - O or $NR_4$ when ══ $X_4$ represents a double bond ═$X_4$, and
  - $OR_4$ or $NR_4R_5$ when ══ $X_4$ represents a single bond —$X_4$,
- $Y_1$ and $Y_2$ represent, independently of each other, a halogen atom, $R_{100}$, $OR_{101}$ or $NR_{102}R_{103}$, provided that at least one of $Y_1$ and $Y_2$ represent a group other than H,
- $R_0$ represents H; CHO; $CO_2$—(($C_1$-$C_6$)alkyl); or a ($C_1$-$C_6$)alkyl optionally substituted with CHO, $CO_2H$ or $CO_2$—(($C_1$-$C_6$)alkyl),
- $R_1$ and $R_2$ represent, independently of each other, H or a ($C_1$-$C_6$)alkyl,
- $R_3$ and $R_4$ represent, independently of each other, H, ($C_1$-$C_6$)alkyl, aryl, heterocycle, —(($C_1$-$C_6$)alkyl)-$X_5$-aryl or —(($C_1$-$C_6$)alkyl)-$X_5$-heterocycle, with $X_5$ representing a bond, O, S or $NR_6$ and each aryl or heterocycle moiety being optionally substituted,
- $R_5$ and $R_6$ represent, independently of each other, H or a ($C_1$-$C_6$)alkyl, and notably H,
- $R_{100}$, $R_{101}$, $R_{102}$ and $R_{103}$ represent, independently of one another, H, optionally substituted aryl, optionally substituted heterocycle, or —(($C_1$-$C_6$)alkyl)-$X_6$-$A_1$, with $X_6$ representing a bond, O, S or $NR_{104}$ and $A_1$ representing H, ($C_1$-$C_6$)alkyl, optionally substituted aryl or optionally substituted heterocycle,
- or, for the $R_{102}$ and $R_{103}$ groups, $R_{102}$ and $R_{103}$ form together, with the nitrogen carrying them, an optionally substituted heterocycle, and
- $R_{104}$ represents H or a ($C_1$-$C_6$)alkyl.

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "$(C_1-C_6)$alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "$(C_2-C_6)$alkenyl", as used in the present invention, refers to a straight or branched unsaturated hydrocarbon chain containing from 2 to 6 carbon atoms and comprising at least one double bond, notably one double bond, including, but not limited to, ethenyl, propenyl, butenyl, pentenyl, hexenyl and the like. It can be in particular an allyl group.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group. Advantageously, it will be a phenyl group.

The term "aryl-$(C_1-C_6)$alkyl", as used in the present invention, refers to an aryl group as defined above bound to the molecule via a $(C_1-C_6)$alkyl group as defined above. In particular, the aryl-$(C_1-C_6)$alkyl group is a benzyl group.

The term "$(C_1-C_6)$alkyl-aryl", as used in the present invention, refers to a $(C_1-C_6)$alkyl group as defined above bound to the molecule via an aryl group as defined above. In particular, it can be a tolyl group (-$PhCH_3$).

The term "heterocycle" as used in the present invention refers to a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, and notably being a nitrogen atom. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom.

A heterocycle can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc.

The term "nitrogen-containing heterocycle" as used in the present invention refers to a heterocycle as defined above containing at least one nitrogen atom.

Such a nitrogen-containing heterocycle is thus a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, at least one of the heteroatom(s) being a nitrogen atom, and notably all the heteroatoms are nitrogen. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members, in which one carbon atom has been replaced with a nitrogen atom and optionally 1 to 3, notably 1, additional carbon atom(s) has/have each been replaced with a nitrogen or oxygen atom, notably a nitrogen atom.

A nitrogen-containing heterocycle can be notably pyrrole, imidazole, pyrazole, oxazole, isoxazole, thiazole, isothiazole, triazoles (1,2,3-triazole and 1,2,4-triazole), indole, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc.

The term "heterocycle-$(C_1-C_6)$alkyl", as used in the present invention, refers to a heterocycle group as defined above bound to the molecule via a $(C_1-C_6)$alkyl group as defined above.

The term "heteroaryl" as used in the present invention refers to an aromatic heterocycle as defined above.

According to a particular embodiment, the heteroaryl is an aromatic hydrocarbon monocycle or bicycle (i.e. comprising two fused rings), each cycle having 5 or 6 members, notably 6 members, and 1 to 4, notably 1 or 2, carbon atoms having each been replaced with a nitrogen or oxygen atom, notably a nitrogen atom.

A heteroaryl can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, etc.

The term "nitrogen-containing heteroaryl" as used in the present invention refers to an aromatic nitrogen-containing heterocycle as defined above.

According to a particular embodiment, the nitrogen-containing heteroaryl is an aromatic hydrocarbon monocycle or bicycle (i.e. comprising two fused rings), each cycle having 5 or 6 members, notably 6 members, in which one carbon atom has been replaced with a nitrogen atom and optionally 1 to 3, notably 1, additional carbon atom(s) has/have each been replaced with a nitrogen or oxygen atom, notably a nitrogen atom.

A nitrogen-containing heteroaryl can be notably pyrrole, imidazole, pyrazole, oxazole, isoxazole, thiazole, isothiazole, triazoles (1,2,3-triazole and 1,2,4-triazole), indole, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, etc.

The term "piperidinediyl", as used in the present invention, refers to a divalent piperidine moiety. It can be in particular

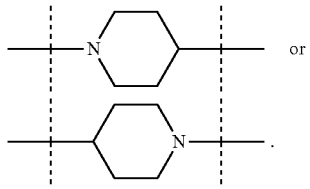

The term "piperazinediyl", as used in the present invention, refers to a divalent piperazine moiety. It can be in particular

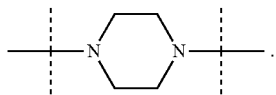

The term "pyrrolidinediyl", as used in the present invention, refers to a divalent pyrrolidine moiety. It can be in particular

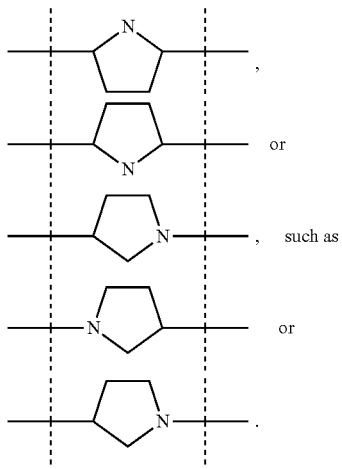

The term "divalent monoglycosyl", as used in the present invention, refers to a divalent monosaccharide moiety in its cyclic form. This monosaccharide will be advantageously linked by two of its oxygen atoms. Advantageously, the monosaccharide is a pentose (deoxyribose, ribose, arabinose, xylose, lyxose, ribulose, xylulose), a hexose (allose, altrose, galactose, glucose, gulose, idose, mannose, talose, fructose, psicose, sorbose, tagatose), fucose or rhamnose, in their D or L forms. The monosaccahride is advantageously a hexose in its pyranose form such as allose, altrose, galactose, glucose, gulose, idose, mannose, talose, fructose, psicose, sorbose or tagatose, notably allose, altrose, galactose, glucose, gulose, idose, mannose or talose, and in particular glucose. The divalent monoglycosyl will be advantageously a group

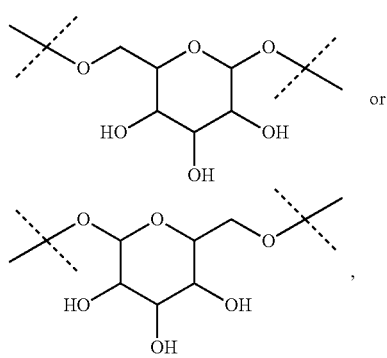

such as

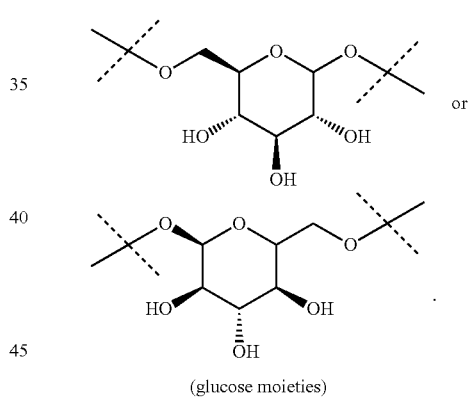

(glucose moieties)

An "optionally substituted" radical, as used in the present invention, refers to a radical optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-($C_1$-$C_6$)alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, with $R_{11}$ to $R_{40}$ and $R_{50}$ to $R_{61}$ representing, independently of one another, H or ($C_1$-$C_6$)alkyl.

The person skilled in the art will understand however that oxo (=O) cannot represent a substituent of an aryl moiety.

The term "halogen", as used in the present invention, refers to a fluorine, bromine, chlorine or iodine atom.

According to a particular embodiment of the present invention, the compound of the present invention is a compound of the following formula (I-1) or (I-2), in particular of the following formula (I-1):

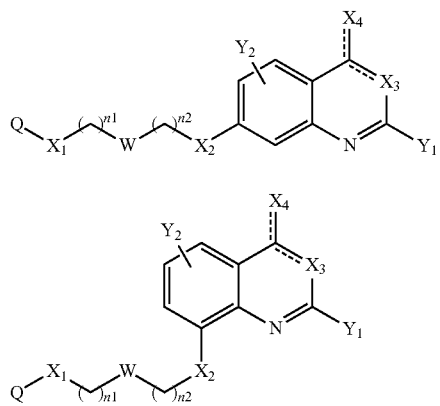
(I-1)

(I-2)

or a pharmaceutically acceptable salt or solvate thereof.

According to another particular embodiment of the present invention, the compound of the present invention is a compound of the following formula (I-3) or (I-4), in particular of the following formula (I-3):

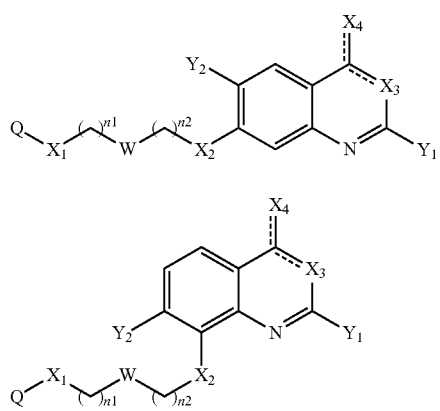
(I-3)

(I-4)

or a pharmaceutically acceptable salt or solvate thereof.

The formula (I) of the present invention comprises two bonds =====. According to a particular embodiment, one of them is a single bond and the other is a double bond. Thus the compound of the present invention can correspond to a compound of the following formula (Ia) or (Ib), preferably of the following formula (Ia):

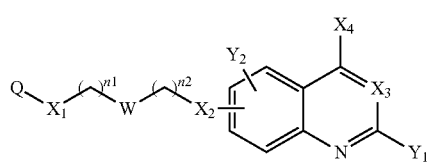
(Ia)

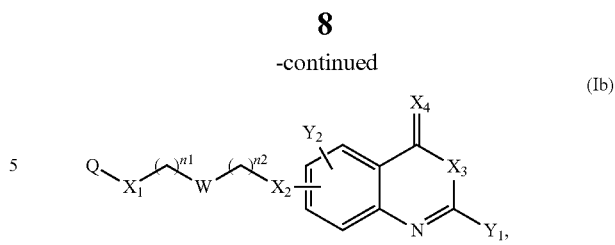
(Ib)

or a pharmaceutically acceptable salt or solvate thereof.

According to another particular embodiment of the present invention, the compound of the present invention is a compound of the following formula (I-1a), (I-1b), (I-2a) or (I-2b), preferably of the following formula (I-1a) or (I-2a), in particular of the following formula (I-1a):

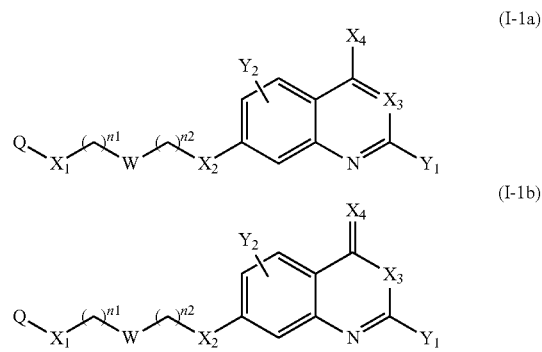
(I-1a)

(I-1b)

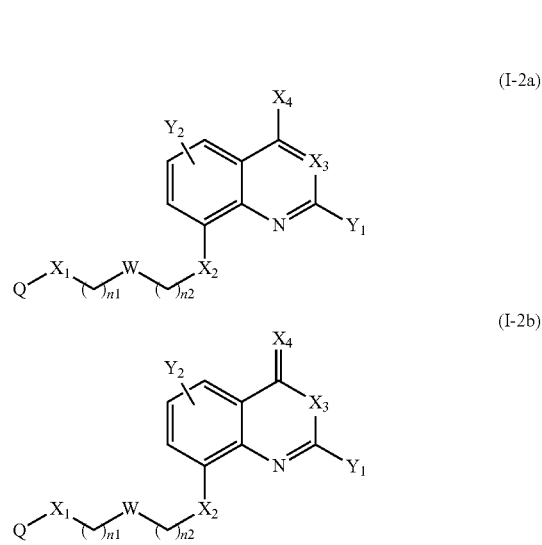
(I-2a)

(I-2b)

or a pharmaceutically acceptable salt or solvate thereof.

According to another particular embodiment of the present invention, the compound of the present invention is a compound of the following formula (I-3a), (I-3b), (I-4a) or (I-4b), preferably of the following formula (I-3a) or (I-4a), in particular of the following formula (I-3a):

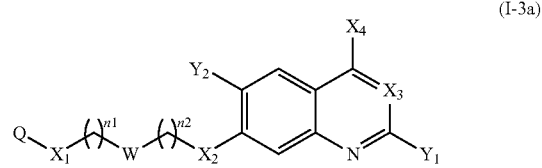
(I-3a)

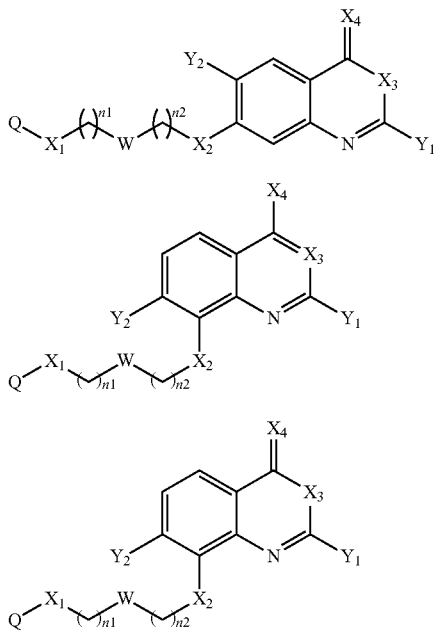

or a pharmaceutically acceptable salt or solvate thereof.

In particular, n1 can represent 0, 1, 2, 3 or 4, notably 0, 1 or 2.

n1 can represent also 1, 2, 3 or 4, notably 1 or 2.

In particular, n2 can represent 0, 1, 2, 3 or 4, notably 0, 1 or 2.

n2 can represent also 1, 2, 3 or 4, notably 1 or 2.

According to a preferred embodiment, n1 represents 1, 2, 3 or 4, notably 1 or 2, and n2 represents 0, 1, 2, 3 or 4, notably 0, 1 or 2, provided that n2≠0 when $X_2$=O or $NR_2$.

$X_1$ represents advantageously NH or O, in particular NH.

$X_2$ represents advantageously a bond, NH or O, in particular a bond or O, such as O.

According to a particular embodiment, $X_1$ represents $NR_1$ and $X_2$ represents a bond or O, such as O; notably $X_1$ represents NH and $X_2$ represents a bond or O, such as O.

According to a first embodiment, W represents a bond, a divalent monoglycosyl, $NR_0$, a piperidinediyl, a piperazinediyl or a pyrrolidinediyl.

According to a second embodiment, W represents a bond, a divalent monoglycosyl, a piperidinediyl, a piperazinediyl or a pyrrolidinediyl. Advantageously, W represents a bond, a piperidinediyl or a piperazinediyl.

According to a third embodiment, W represents $NR_0$, a divalent monoglycosyl, a piperidinediyl, a piperazinediyl or a pyrrolidinediyl, notably $NR_0$, a piperidinediyl or a piperazinediyl.

According to a fourth embodiment, W represents a divalent monoglycosyl, a piperidinediyl, a piperazinediyl or a pyrrolidinediyl, notably a divalent monoglycosyl, a piperidinediyl or a piperazinediyl. Advantageously, W represents a piperidinediyl or a piperazinediyl.

According to sixth embodiment, W represents a divalent monoglycosyl.

In these six embodiments, the piperidinediyl group can be

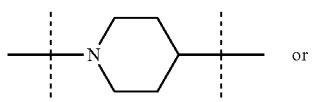 or

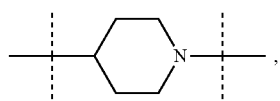

and in particular is

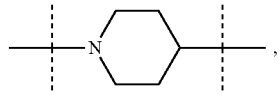

the nitrogen atom being linked to $(CH_2)_{n1}$. The piperazinediyl group is in particular

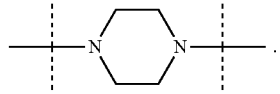.

The pyrrolidinediyl group can be

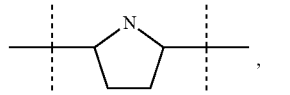

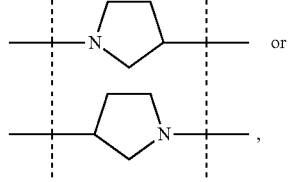

such as

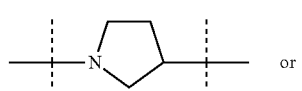 or

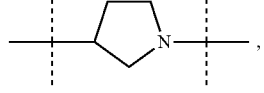, and in particular is

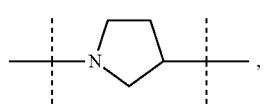, the nitrogen atom being linked to $(CH_2)_{n1}$. The divalent monoglycosyl group can be

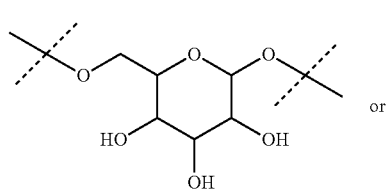 or

-continued

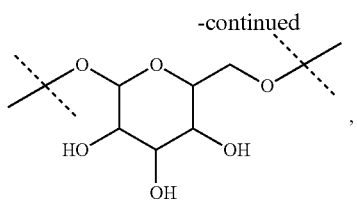

such as

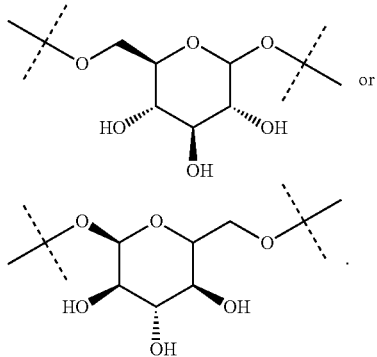

or

In particular, the divalent monoglycosyl group can be

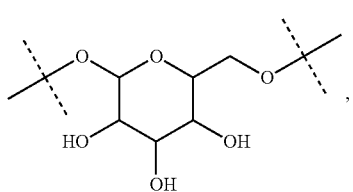

such as

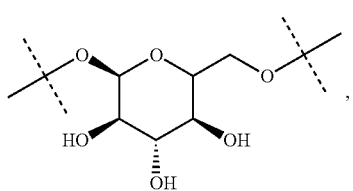

the oxygen atom of the CH$_2$O moiety being linked to (CH$_2$)$_{n1}$. R$_0$ represents notably H; CHO; or a (C$_1$-C$_6$)alkyl optionally substituted with CO$_2$H or CO$_2$—((C$_1$-C$_6$)alkyl) (e.g. CO$_2$Me). According to a first particular embodiment, R$_0$ represents H. According to a second particular embodiment, R$_0$ represents CHO or CO$_2$—((C$_1$-C$_6$)alkyl), such as CHO. According to a third particular embodiment, R$_0$ represents a (C$_1$-C$_6$)alkyl optionally substituted with CHO, CO$_2$H or CO$_2$—((C$_1$-C$_6$)alkyl); notably a (C$_1$-C$_6$)alkyl optionally substituted with CO$_2$H or CO$_2$—((C$_1$-C$_6$)alkyl) (e.g. CO$_2$Me); in particular an unsubstituted (C$_1$-C$_6$)alkyl. According to a fourth particular embodiment, R$_0$ represents H or a (C$_1$-C$_6$)alkyl.

Q represents notably an aryl or nitrogen-containing heterocycle, notably a nitrogen-containing heterocycle, optionally substituted with one or several groups selected from halogen; oxo (=O); NO$_2$; OR$_{11}$; NR$_{12}$R$_{13}$; C(O)R$_{14}$; CO$_2$R$_{15}$; OC(O)R$_{16}$; C(O)NR$_{17}$R$_{18}$; NR$_{19}$C(O)R$_{20}$; S(O)R$_{50}$; S(O)$_2$R$_{51}$; S(O)$_2$NR$_{52}$R$_{53}$; (C$_1$-C$_6$)alkyl optionally substituted with one or several groups selected from halogen, OR$_{21}$, NR$_{22}$R$_{23}$, C(O)R$_{24}$, CO$_2$R$_{25}$, OC(O)R$_{26}$, C(O)NR$_{27}$R$_{28}$, NR$_{29}$C(O)R$_{30}$, S(O)R$_{54}$, S(O)$_2$R$_{55}$, and S(O)$_2$NR$_{56}$R$_{57}$; and aryl or aryl-(C$_1$-C$_6$)alkyl optionally substituted with one or several groups selected from halogen, OR$_{31}$, NR$_{32}$R$_{33}$, C(O)R$_{34}$, CO$_2$R$_{35}$, OC(O)R$_{36}$, C(O)NR$_{37}$R$_{38}$, NR$_{39}$C(O)R$_{40}$, S(O)R$_{58}$, S(O)$_2$R$_{59}$, and S(O)$_2$NR$_{60}$R$_{61}$, with R$_{11}$ to R$_{40}$ and R$_{50}$ to R$_{61}$ representing, independently of one another, H or (C$_1$-C$_6$)alkyl.

Q represents notably an aryl or nitrogen-containing heterocycle, notably a nitrogen-containing heterocycle, optionally substituted with one or several groups selected from halogen; oxo (=O); OR$_{11}$; NR$_{12}$R$_{13}$; C(O)R$_{14}$; CO$_2$R$_{15}$; OC(O)R$_{16}$; C(O)NR$_{17}$R$_{18}$; NR$_{19}$C(O)R$_{20}$; (C$_1$-C$_6$)alkyl optionally substituted with one or several groups selected from halogen, OR$_{21}$, NR$_{22}$R$_{23}$, C(O)R$_{24}$, CO$_2$R$_{25}$, OC(O)R$_{26}$, C(O)NR$_{27}$R$_{28}$, and NR$_{29}$C(O)R$_{30}$; and aryl optionally substituted with one or several groups selected from halogen, OR$_{31}$, NR$_{32}$R$_{33}$, C(O)R$_{34}$, CO$_2$R$_{35}$, OC(O)R$_{36}$, C(O)NR$_{37}$R$_{38}$, and NR$_{39}$C(O)R$_{40}$, with R$_{11}$ to R$_{40}$ representing, independently of one another, H or (C$_1$-C$_6$)alkyl.

Q represents in particular an aryl or nitrogen-containing heterocycle, notably a nitrogen-containing heterocycle, optionally substituted with one or several groups selected from halogen; oxo (=O); (C$_1$-C$_6$)alkyl optionally substituted with one or several groups selected from halogen, OR$_{21}$, NR$_{22}$R$_{23}$, C(O)R$_{24}$, CO$_2$R$_{25}$, OC(O)R$_{26}$, C(O)NR$_{27}$R$_{28}$, and NR$_{29}$C(O)R$_{30}$; and aryl optionally substituted with one or several groups selected from halogen, OR$_{31}$, NR$_{32}$R$_{33}$, C(O)R$_{34}$, CO$_2$R$_{35}$, OC(O)R$_{36}$, C(O)NR$_{37}$R$_{38}$, and NR$_{39}$C(O)R$_{40}$.

Q can also represent an aryl or nitrogen-containing heterocycle, notably a nitrogen-containing heterocycle, optionally substituted with one or several groups selected from halogen; oxo (=O); OR$_{11}$; NR$_{12}$R$_{13}$; C(O)R$_{14}$; CO$_2$R$_{15}$; OC(O)R$_{16}$; C(O)NR$_{17}$R$_{18}$; NR$_{19}$C(O)R$_{20}$; and (C$_1$-C$_6$)alkyl optionally substituted with one or several groups selected from halogen, OR$_{21}$, NR$_{22}$R$_{23}$, C(O)R$_{24}$, CO$_2$R$_{25}$, OC(O)R$_{26}$, C(O)NR$_{27}$R$_{28}$, and NR$_{29}$C(O)R$_{30}$.

Q can represent in particular an aryl or nitrogen-containing heterocycle, notably a nitrogen-containing heterocycle, optionally substituted with one or several groups selected from halogen; oxo (=O); OR$_{11}$; NR$_{12}$R$_{13}$; and (C$_1$-C$_6$)alkyl optionally substituted with one or several groups selected from halogen, OR$_{21}$ and NR$_{22}$R$_{23}$.

Q represents particularly an aryl or nitrogen-containing heterocycle, notably a nitrogen-containing heterocycle, optionally substituted with one or several groups selected from halogen; oxo (=O); and (C$_1$-C$_6$)alkyl optionally substituted with one or several groups selected from halogen, OR$_{21}$ and NR$_{22}$R$_{23}$.

Q represents more particularly an aryl or nitrogen-containing heterocycle, notably a nitrogen-containing heterocycle, optionally substituted with one or several groups selected from halogen, oxo (=O), and (C$_1$-C$_6$)alkyl. Q can represent also an aryl or nitrogen-containing heterocycle, notably a nitrogen-containing heterocycle.

In the definitions of Q above, the aryl is preferably a phenyl or a naphtyl, in particular a phenyl.

In the definitions of Q above, the nitrogen-containing heterocycle is notably a saturated, unsaturated or aromatic hydrocarbon monocycle or bicycle (comprising fused, bridged or spiro rings, notably fused rings), each cycle having 5 or 6 members, in which one carbon atom has been replaced with a nitrogen atom and optionally 1 to 3, notably 1, additional carbon atom(s) has/have each been replaced with a nitrogen or oxygen atom, notably a nitrogen atom. The heterocycle can be notably chosen among pyrrole, imidazole, pyrazole, triazoles, indole, benzimidazole, indazole, pyridine, pyrimidine, pyridazine, pyrazine, triazine, quinoline, isoquinoline, quinoxaline, quinazoline, piperidine, piperazine, triazinane, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines and tetrahydrotriazines. In particular, the heterocycle can be chosen among pyridine, pyrimidine, pyridazine, pyrazine, quinoline, isoquinoline, quinoxaline, quinazoline, piperidine, piperazine, dihydropyridines, dihydropyrimidines (notably 1,2-dihydropyrimidine), dihydropyridazines, dihydropyrazines, tetrahydropyridines, tetrahydropyrimidines, tetrahydropyridazines and tetrahydropyrazines. More particularly, the heterocycle can be chosen among quinoline, quinazoline, pyridine, pyrimidine and dihydropyrimidines (notably 1,2-dihydropyrimidine). Notably, the heterocycle can be chosen among quinoline, pyridine and dihydropyrimidines (notably 1,2-dihydropyrimidine).

In the definitions of Q above, the nitrogen-containing heterocycle is preferably a nitrogen-containing heteroaryl, such as an aromatic hydrocarbon monocycle or bicycle (i.e. comprising fused rings), each cycle having 5 or 6 members, notably 6 members, in which one carbon atom has been replaced with a nitrogen atom and optionally 1 to 3, notably 1, additional carbon atom(s) has/have each been replaced with a nitrogen or oxygen atom, notably a nitrogen atom. Preferably, the nitrogen-containing hereoaryl is an aromatic hydrocarbon monocycle or bicycle (i.e. comprising fused rings), each cycle having 6 members, in which one carbon atom has been replaced with a nitrogen atom and optionally one additional carbon atom has been replaced with a nitrogen or oxygen atom, notably a nitrogen atom. The nitrogen-containing heteroaryl can be notably chosen among pyrrole, imidazole, pyrazole, oxazole, isoxazole, thiazole, isothiazole, triazoles (1,2,3-triazole and 1,2,4-triazole), indole, benzimidazole, indazole, benzoxazole, benzisoxazole, benzothiazole, benzisothiazole, pyridine, pyrimidine, pyridazine, pyrazine, triazine, quinoline, isoquinoline, quinoxaline and quinazoline. In particular, the nitrogen-containing heteroaryl can be chosen among pyridine, pyrimidine, pyridazine, pyrazine, quinoline, isoquinoline, quinoxaline, and quinazoline. Notably, the nitrogen-containing heteroaryl can be chosen among quinoline, quinazoline, pyridine and pyrimidine. In particular, it is quinoline or pyridine.

In the definitions of Q above, the nitrogen-containing heterocycle can be in particular a quinoline.

According to a preferred embodiment, Q represents a cycle of the following formula:

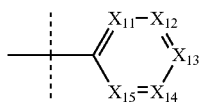

wherein:
$X_{11}$ represents N or $CR_{41}$,
$X_{12}$ represents N or $CR_{42}$,
$X_{13}$ represents N or C—$NR_{43a}R_{43b}$, notably N,
$X_{14}$ represents N or $CR_{44}$,
$X_{15}$ represents N or $CR_{45}$,
$R_{43a}$ and $R_{43b}$ each represent, independently of each other, H or ($C_1$-$C_6$)alkyl (such as methyl),
$R_{41}$, $R_{42}$, $R_{44}$ and $R_{45}$ each represent, independently of each other, hydrogen; halogen; $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; or aryl or aryl-($C_1$-$C_6$)alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, or in the case of $R_{44}$ and $R_{45}$, $R_{44}$ and $R_{45}$ form together a chain of the following formula:

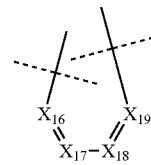

wherein:
$X_{16}$ represents N or $CR_{46}$,
$X_{17}$ represents N or $CR_{47}$,
$X_{18}$ represents N or $CR_{48}$,
$X_{19}$ represents N or $CR_{49}$, and
$R_{46}$, $R_{47}$, $R_{48}$ and $R_{49}$ each represent, independently of one another, hydrogen; halogen; $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; or aryl or aryl-($C_1$-$C_6$)alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, on the proviso that no more than three, notably two, and preferably one, of $X_{11}$, $X_{12}$, $X_{14}$, $X_{15}$, $X_{16}$, $X_{17}$, $X_{18}$ and $X_{19}$ represent N.

In particular, none of $X_{11}$, $X_{12}$, $X_{14}$, $X_{15}$, $X_{16}$, $X_{17}$, $X_{18}$ and $X_{19}$ represents N.

In particular, none of $X_{11}$, $X_{12}$, $X_{14}$, $X_{15}$, $X_{16}$, $X_{17}$, $X_{18}$ and $X_{19}$ represents N and $X_{13}$ represents N.

Advantageously, $R_{41}$, $R_{42}$, $R_{44}$ and $R_{45}$ each represent, independently of each other, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; or aryl or aryl-($C_1$-$C_6$)alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$, or in the case of $R_{44}$ and $R_{45}$, $R_{44}$ and $R_{45}$ form together a chain of the following formula:

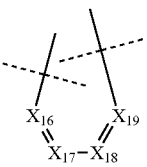

with $R_{46}$, $R_{47}$, $R_{48}$ and $R_{49}$ each representing, independently of one another, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; or aryl or aryl-($C_1$-$C_6$)alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$.

In particular, $R_{41}$, $R_{42}$, $R_{44}$ and $R_{45}$ each represent, independently of each other, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; or ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$, or in the case of $R_{44}$ and $R_{45}$, $R_{44}$ and $R_{45}$ form together a chain of the following formula:

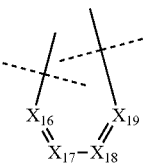

with $R_{46}$, $R_{47}$, $R_{48}$ and $R_{49}$ each representing, independently of one another, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; or ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$.

Notably, $R_{41}$, $R_{42}$, $R_{44}$ and $R_{45}$ each represent, independently of each other, hydrogen; halogen; $OR_{11}$; $NR_{12}R_{13}$; or ($C_1$-$C_6$)alkyl optionally substituted with one or several groups selected from halogen, $OR_{21}$, and $NR_{22}R_{23}$, or in the case of $R_{44}$ and $R_{45}$, $R_{44}$ and $R_{45}$ form together a chain of the following formula:

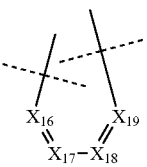

with $R_{46}$, $R_{47}$, $R_{48}$ and $R_{49}$ each representing, independently of one another, hydrogen; halogen; $OR_{11}$; $NR_{12}R_{13}$; or ($C_1$-$C_6$)alkyl optionally substituted with one or several groups selected from halogen, $OR_{21}$, and $NR_{22}R_{23}$.

In particular, $R_{41}$, $R_{42}$, $R_{44}$ and $R_{45}$ each represent, independently of each other, hydrogen; halogen; $OR_{11}$; or $NR_{12}R_{13}$; and notably hydrogen, or in the case of $R_{44}$ and $R_{45}$, $R_{44}$ and $R_{45}$ form together a chain of the following formula:

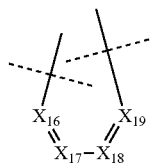

with $R_{46}$, $R_{47}$, $R_{48}$ and $R_{49}$ each representing, independently of one another, hydrogen; halogen; $OR_{11}$; or $NR_{12}R_{13}$.

Preferably, $R_{44}$ and $R_{45}$ form together a chain of the following formula

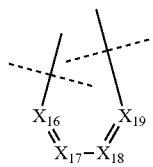

According to a most preferred embodiment, Q represents one of the following cycles:

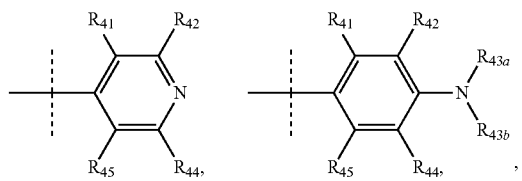

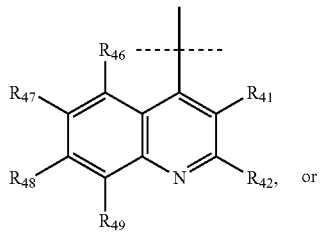   or

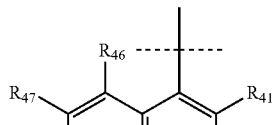

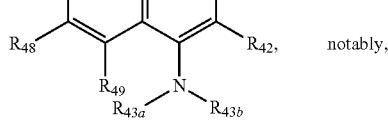   notably,

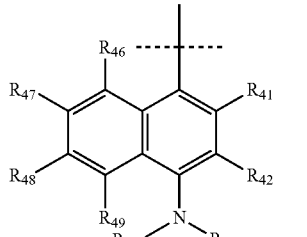   or

-continued

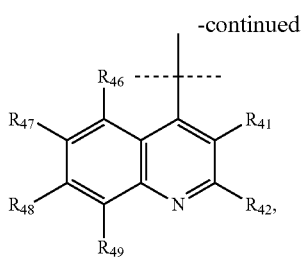

and preferably represents the cycle

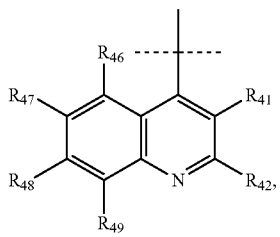

with $R_{43a}$ and $R_{43b}$ as defined above and with $R_{41}$, $R_{42}$ and $R_{44}$ to $R_{49}$ as defined according to one of the definitions above, and in particular with $R_{41}$, $R_{42}$ and $R_{44}$ to $R_{49}$ each representing, independently of one another, hydrogen; halogen; $OR_{11}$; or $NR_{12}R_{13}$.

In particular, Q represents one of the following cycles:

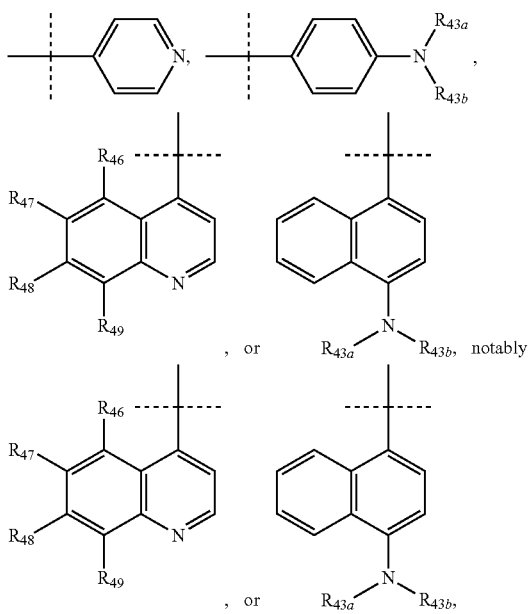

, or and preferably represents the cycle

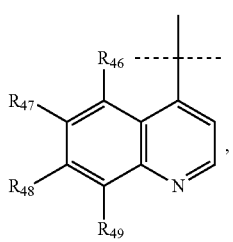

with $R_{43a}$ and $R_{43b}$ as defined above and with $R_{46}$ to $R_{49}$ as defined according to one of the definitions above, and in particular with $R_{46}$ to $R_{49}$ each representing, independently of one another, hydrogen; halogen; $OR_{11}$; or $NR_{12}R_{13}$.

Q can be for example one of the following cycles:

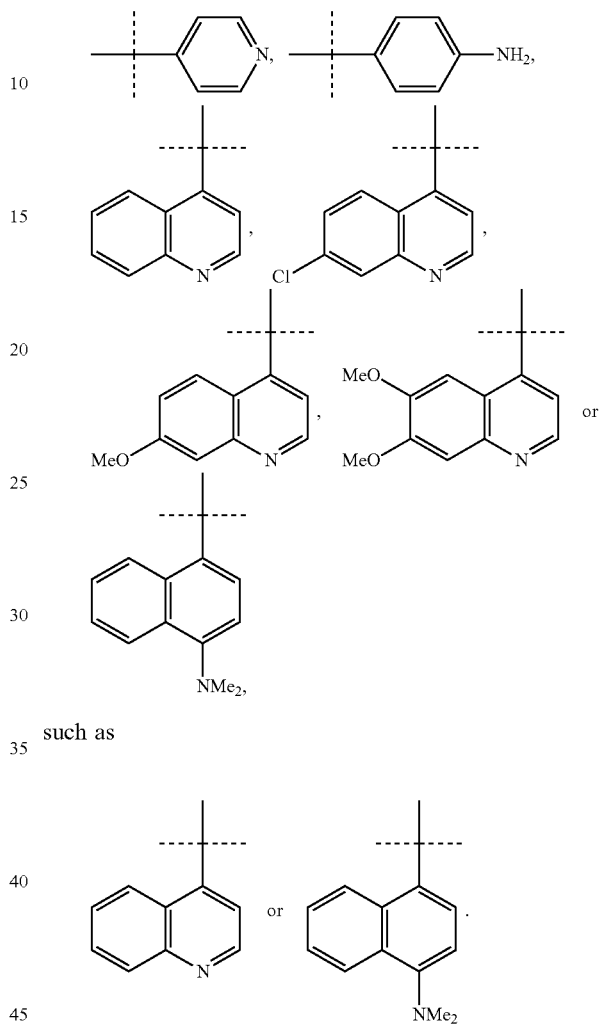

such as

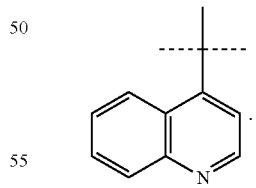

Q can be in particular

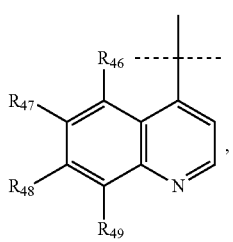

According to a particular embodiment, $X_3$ represents:
N when $=\!=\!= X_3$ represents a double bond $=\!X_3$, and
$NR_3$ when $=\!=\!= X_3$ represents a single bond $-X_3$, According to another particular embodiment, $X_4$ represents:
O when $=\!=\!= X_4$ represents a double bond $=\!X_4$, and
$NR_4R_5$ when $=\!=\!= X_4$ represents a single bond $-X_4$, The compound of the present invention can correspond in particular to a compound of the following formula (Ic) or (Id), preferably of the following formula (I-c):

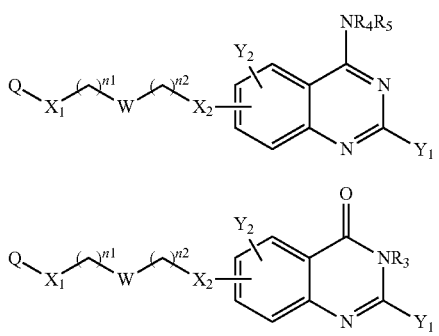

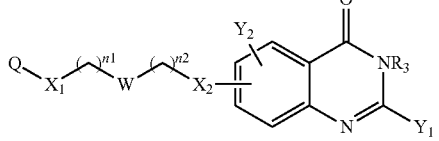

or a pharmaceutically acceptable salt or solvate thereof.

According to another particular embodiment of the present invention, the compound of the present invention is a compound of the following formula (I-1c), (I-1d), (I-2c) or (I-2d), preferably of the following formula (I-1c) or (I-2c), in particular of the following formula (I-1c):

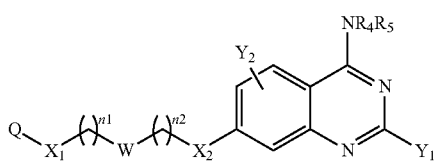

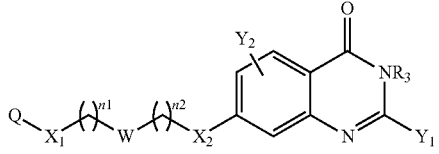

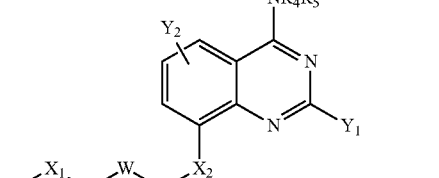

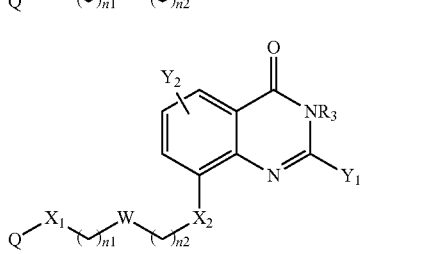

or a pharmaceutically acceptable salt or solvate thereof.

According to another particular embodiment of the present invention, the compound of the present invention is a compound of the following formula (I-3c), (I-3d), (I-4c) or (I-4d), preferably of the following formula (I-3c) or (I-4c), in particular of the following formula (I-3c):

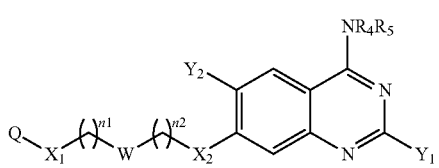

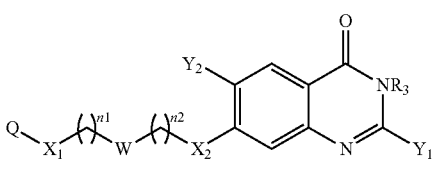

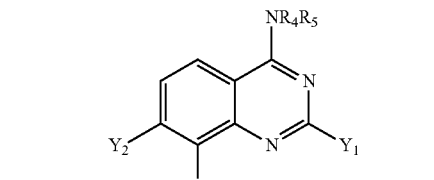

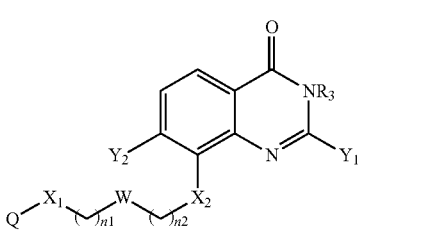

or a pharmaceutically acceptable salt or solvate thereof.

More particularly, $R_3$ and $R_4$ will represent, independently of each other, H, $(C_1-C_6)$alkyl, aryl, heterocycle, —(($C_1$-$C_6$)alkyl)-$X_5$-aryl or —(($C_1$-$C_6$)alkyl)-$X_5$-heterocycle; such as H, $(C_1-C_6)$alkyl, aryl, heterocycle, aryl-$(C_1-C_6)$alkyl, heterocycle-$(C_1-C_6)$alkyl, —(($C_1$-$C_6$)alkyl)-NH-aryl or —(($C_1$-$C_6$)alkyl)-NH-heterocycle; notably aryl, heterocycle, aryl-$(C_1-C_6)$alkyl, heterocycle-$(C_1-C_6)$alkyl, —(($C_1$-$C_6$)alkyl)-NH-aryl or —(($C_1$-$C_6$)alkyl)-NH-heterocycle; more particularly heterocycle, aryl-$(C_1-C_6)$alkyl or —(($C_1$-$C_6$)alkyl)-NH-aryl, each aryl or heterocycle moiety being optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, with $R_{11}$ to $R_{40}$ and $R_{50}$ to $R_{61}$ representing, independently of one another, H or $(C_1-C_6)$alkyl.

$R_3$ and $R_4$ represent notably, independently of each other, H, $(C_1-C_6)$alkyl, aryl, heterocycle, —(($C_1$-$C_6$)alkyl)-$X_5$-aryl or —(($C_1$-$C_6$)alkyl)-$X_5$-heterocycle; such as H, $(C_1-C_6)$alkyl, aryl, heterocycle, aryl-$(C_1-C_6)$alkyl, heterocycle-$(C_1-C_6)$alkyl, —(($C_1$-$C_6$)alkyl)-NH-aryl or —(($C_1$-$C_6$)alkyl)-NH-heterocycle; notably aryl, heterocycle, aryl-$(C_1-C_6)$alkyl, heterocycle-$(C_1-C_6)$alkyl, —(($C_1$-$C_6$)alkyl)-NH-aryl or —(($C_1$-$C_6$)alkyl)-NH-heterocycle; more particularly heterocycle, aryl-$(C_1-C_6)$alkyl or —(($C_1$-$C_6$)alkyl)-NH-aryl, each aryl or heterocycle moiety being optionally substituted with one or several groups selected from halogen; oxo (=O); $NO_2$; $OR_{11}$; $NR_{12}R_{13}$; $C(O)R_{14}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, $S(O)_2R_{55}$, and $S(O)_2NR_{56}R_{57}$; and aryl or aryl- ($C_1$-$C_6$)alkyl optionally substituted with one or several groups selected from halogen, $OR_{31}$, $NR_{32}R_{33}$, $C(O)R_{34}$, $S(O)_2R_{59}$, and $S(O)_2NR_{60}R_{61}$.

$R_3$ and $R_4$ represent notably, independently of each other, H, ($C_1$-$C_6$)alkyl, aryl, heterocycle, —(($C_1$-$C_6$)alkyl)-$X_5$-aryl or —(($C_1$-$C_6$)alkyl)-$X_5$-heterocycle; such as H, ($C_1$-$C_6$)alkyl, aryl, heterocycle, aryl-($C_1$-$C_6$)alkyl, heterocycle-($C_1$-$C_6$)alkyl, —(($C_1$-$C_6$)alkyl)-NH-aryl or —(($C_1$-$C_6$)alkyl)-NH-heterocycle; notably aryl, heterocycle, aryl-($C_1$-$C_6$)alkyl, heterocycle-($C_1$-$C_6$)alkyl, —(($C_1$-$C_6$)alkyl)-NH-aryl or —(($C_1$-$C_6$)alkyl)-NH-heterocycle; more particularly heterocycle, aryl-($C_1$-$C_6$)alkyl or —(($C_1$-$C_6$)alkyl)-NH-aryl, each aryl or heterocycle moiety being optionally substituted with one or several groups selected from halogen; oxo (=O); $NO_2$; $OR_{11}$; $NR_{12}R_{13}$; $C(O)R_{14}$; ($C_1$-$C_6$)alkyl optionally substituted with one or several groups selected from halogen, $OR_{21}$ and $NR_{22}R_{23}$; and aryl or aryl-($C_1$-$C_6$)alkyl optionally substituted with one or several groups selected from halogen, $OR_{31}$ and $NR_{32}R_{33}$.

$R_3$ and $R_4$ represent notably, independently of each other, H, ($C_1$-$C_6$)alkyl, aryl, heterocycle, —(($C_1$-$C_6$)alkyl)-$X_5$-aryl or —(($C_1$-$C_6$)alkyl)-$X_5$-heterocycle; such as H, ($C_1$-$C_6$)alkyl, aryl, heterocycle, aryl-($C_1$-$C_6$)alkyl, heterocycle-($C_1$-$C_6$)alkyl, —(($C_1$-$C_6$)alkyl)-NH-aryl or —(($C_1$-$C_6$)alkyl)-NH-heterocycle; notably aryl, heterocycle, aryl-($C_1$-$C_6$)alkyl, heterocycle-($C_1$-$C_6$)alkyl, —(($C_1$-$C_6$)alkyl)-NH-aryl or —(($C_1$-$C_6$)alkyl)-NH-heterocycle; more particularly heterocycle, aryl-($C_1$-$C_6$)alkyl or —(($C_1$-$C_6$)alkyl)-NH-aryl, each aryl or heterocycle moiety being optionally substituted with one or several groups selected from halogen; oxo (=O); $NO_2$; $OR_{11}$; $NR_{12}R_{13}$; $S(O)_2R_{51}$; $S(O)_2NR_{52}R_{53}$; $C_1$-$C_6$)alkyl optionally substituted with one or several groups selected from halogen, $OR_{21}$ and $NR_{22}R_{23}$; and aryl or aryl-($C_1$-$C_6$)alkyl optionally substituted with one or several groups selected from halogen, $OR_{31}$ and $NR_{32}R_{33}$.

$R_3$ and $R_4$ represent notably, independently of each other, H, ($C_1$-$C_6$)alkyl, aryl, heterocycle, —(($C_1$-$C_6$)alkyl)-$X_5$-aryl or —(($C_1$-$C_6$)alkyl)-$X_5$-heterocycle; such as H, ($C_1$-$C_6$)alkyl, aryl, heterocycle, aryl-($C_1$-$C_6$)alkyl, heterocycle-($C_1$-$C_6$)alkyl, —(($C_1$-$C_6$)alkyl)-NH-aryl or —(($C_1$-$C_6$)alkyl)-NH-heterocycle; notably aryl, heterocycle, aryl-($C_1$-$C_6$)alkyl, heterocycle-($C_1$-$C_6$)alkyl, —(($C_1$-$C_6$)alkyl)-NH-aryl or —(($C_1$-$C_6$)alkyl)-NH-heterocycle; more particularly heterocycle, aryl-($C_1$-$C_6$)alkyl or —(($C_1$-$C_6$)alkyl)-NH-aryl, each aryl or heterocycle moiety being optionally substituted with one or several groups selected from halogen; $OR_{11}$; $NR_{12}R_{13}$; ($C_1$-$C_6$)alkyl optionally substituted with one or several groups selected from halogen, $OR_{21}$ and $NR_{22}R_{23}$; and aryl or aryl-($C_1$-$C_6$)alkyl optionally substituted with one or several groups selected from halogen, $OR_{31}$ and $NR_{32}R_{33}$.

$R_3$ and $R_4$ represent advantageously, independently of each other, a group:

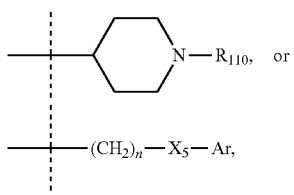

where $R_{110}$ represents an aryl or aryl-($C_1$-$C_6$)alkyl group, such as an aryl-($C_1$-$C_6$)alkyl group, optionally substituted with one or several halogen atoms, n is an integer comprised between 1 and 6, $X_5$ is as defined above and notably is a bond or NH, and Ar is an aryl group such as phenyl or naphtyl, in particular where $R_{110}$ represents a benzyl or naphtylmethyl group optionally substituted with one or several halogen atoms, n is an integer comprised between 1 and 6, $X_5$ is a bond or NH, and Ar is phenyl or naphtyl.

In the definitions of $R_3$ and $R_4$ above, the aryl preferably is a phenyl or a naphtyl.

In the definitions of $R_3$ and $R_4$ above, the heterocycle is notably a saturated, unsaturated or aromatic (notably aromatic) hydrocarbon monocycle or bicycle (comprising fused, bridged or spiro rings, notably fused rings), notably a monocycle, each cycle having 5 or 6 members and 1 to 4, notably 1 or 2, carbon atoms having each been replaced with a nitrogen or oxygen atom, notably a nitrogen atom. The heterocycle can be a heteroaryl. The heterocycle can be notably chosen among pyrrole, imidazole, pyrazole, triazoles, indole, benzimidazole, indazole, pyridine, pyrimidine, pyridazine, pyrazine, triazine, quinoline, isoquinoline, quinoxaline, quinazoline, piperidine, piperazine, triazinane, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines and tetrahydrotriazines. According to a first embodiment, the heterocycle is chosen among pyrrole, imidazole, pyrazole, triazoles, indole, benzimidazole, indazole, pyridine, pyrimidine, pyridazine, pyrazine, triazine, quinoline, isoquinoline, quinoxaline and quinazoline; notably chosen among pyridine, pyrimidine, pyridazine, pyrazine, triazine, quinoline, isoquinoline, quinoxaline and quinazoline. According to a second embodiment, the heterocycle is chosen among piperidine, piperazine, triazinane or pyrrolidine; and in particular is piperidine.

In the definitions of $R_3$ and $R_4$ above, $X_5$ represents in particular a bond or $NR_6$, notably a bond or NH.

According to a preferred embodiment, $R_5$ represents H.

$Y_1$ and $Y_2$ represent, independently of each other, a halogen atom, $R_{100}$, $OR_{101}$ or $NR_{102}R_{103}$; notably H, a halogen atom, $OR_{101}$ or $NR_{102}R_{103}$, provided that at least one of $Y_1$ and $Y_2$ represent a group other than H.

According to a particular embodiment, $Y_1$ represents H, a halogen atom, $OR_{101}$ or $NR_{102}R_{103}$; notably H, a halogen atom or $NR_{102}R_{103}$, provided that $Y_2$ does not represent a hydrogen atom when $Y_1$=H.

According to a particular embodiment, $Y_2$ represents H, a halogen atom, $OR_{101}$ or $NR_{102}R_{103}$; notably H, a halogen atom or $OR_{101}$; in particular H or $OR_{101}$, provided that $Y_1$ does not represent a hydrogen atom when $Y_2$=H.

According to another particular embodiment, $Y_1$ represents H, a halogen atom or $NR_{102}R_{103}$, and $Y_2$ represents H or $OR_{101}$, provided that at least one of $Y_1$ and $Y_2$ represent a group other than H.

Advantageously, $R_{100}$, $R_{101}$, $R_{102}$ and $R_{103}$ represent, independently of one another, H, optionally substituted aryl, optionally substituted heterocycle, or —(($C_1$-$C_6$)alkyl)-$X_6$-$A_1$, with $X_6$ representing a bond, O or $NR_{104}$, for ex. a bond or $NR_{104}$, and $A_1$ representing H, ($C_1$-$C_6$)alkyl, optionally substituted aryl or optionally substituted heterocycle, or, for the $R_{102}$ and $R_{103}$ groups, $R_{102}$ and $R_{103}$ form together, with the nitrogen carrying them, an optionally substituted heterocycle, and where the optionally substituted aryl and optionally substituted heterocycle are optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, with $R_{11}$ to $R_{40}$ and $R_{50}$ to $R_{61}$ representing, independently of one another, H or $(C_1-C_6)$alkyl.

Notably, $R_{100}$, $R_{101}$, $R_{102}$ and $R_{103}$ represent, independently of one another, H, optionally substituted aryl, optionally substituted heterocycle, or —$((C_1-C_6)$alkyl$)$-$X_6$-$A_1$, with $X_6$ representing a bond, O or $NR_{104}$, for ex. a bond or $NR_{104}$, and $A_1$ representing H, $(C_1-C_6)$alkyl, optionally substituted aryl or optionally substituted heterocycle, or, for the $R_{102}$ and $R_{103}$ groups, $R_{102}$ and $R_{103}$ form together, with the nitrogen carrying them, an optionally substituted heterocycle, and where the optionally substituted aryl and optionally substituted heterocycle are optionally substituted with one or several groups selected from halogen; oxo (═O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1-C_6)$alkyl optionally substituted with one or several groups selected from halogen, $OR_{21}$ or $NR_{22}R_{23}$; and aryl or aryl-$(C_1-C_6)$alkyl optionally substituted with one or several groups selected from halogen, $OR_{31}$ or $NR_{32}R_{33}$.

Notably, $R_{100}$, $R_{101}$, $R_{102}$ and $R_{103}$ represent, independently of one another, H, optionally substituted aryl, optionally substituted heterocycle, or —$((C_1-C_6)$alkyl$)$-$X_6$-$A_1$, with $X_6$ representing a bond, O or $NR_{104}$, for ex. a bond or $NR_{104}$, and $A_1$ representing H, $(C_1-C_6)$alkyl, optionally substituted aryl or optionally substituted heterocycle, or, for the $R_{102}$ and $R_{103}$ groups, $R_{102}$ and $R_{103}$ form together, with the nitrogen carrying them, an optionally substituted heterocycle, and where the optionally substituted aryl and optionally substituted heterocycle are optionally substituted with one or several groups selected from halogen; oxo (═O); $NO_2$; $OR_{11}$; $NR_{12}R_{13}$; $(C_1-C_6)$alkyl optionally substituted with one or several groups selected from halogen, $OR_{21}$ or $NR_{22}R_{23}$; and aryl or aryl-$(C_1-C_6)$alkyl optionally substituted with one or several groups selected from halogen, $OR_{31}$ or $NR_{32}R_{33}$.

In particular, $R_{100}$, $R_{101}$, $R_{102}$ and $R_{103}$ represent, independently of one another, H, $(C_1-C_6)$alkyl, aryl, heterocycle, aryl-$(C_1-C_6)$alkyl, heterocycle-$(C_1-C_6)$alkyl or —$((C_1-C_6)$alkyl$)$-$NR_{104}$-$A_1$, with $A_1$ representing H, $(C_1-C_6)$alkyl, aryl or heterocycle, or, for the $R_{102}$ and $R_{103}$ groups, $R_{102}$ and $R_{103}$ form together, with the nitrogen carrying them, a heterocycle, and where each aryl and heterocycle moiety is optionally substituted with one or several groups selected from halogen; oxo (═O); $(C_1-C_6)$alkyl; aryl; and aryl-$(C_1-C_6)$alkyl.

According to a particular embodiment, $R_{101}$ represents H, $(C_1-C_6)$alkyl, aryl, aryl-$(C_1-C_6)$alkyl or $(C_1-C_6)$alkyl-aryl; notably H or $(C_1-C_6)$alkyl.

According to a particular embodiment, $R_{102}$ and $R_{103}$ represent, independently of one another, H, $(C_1-C_6)$alkyl, aryl, heterocycle, aryl-$(C_1-C_6)$alkyl, heterocycle-$(C_1-C_6)$alkyl or —$((C_1-C_6)$alkyl$)$-$NR_{104}$-$A_1$; notably heterocycle, heterocycle-$(C_1-C_6)$alkyl or —$((C_1-C_6)$alkyl$)$-$NR_{104}$-$A_1$, with $A_1$ representing H, $(C_1-C_6)$alkyl, aryl or heterocycle, or, for the $R_{102}$ and $R_{103}$ groups, $R_{102}$ and $R_{103}$ form together, with the nitrogen carrying them, a heterocycle, and where each aryl and heterocycle moiety is optionally substituted with one or several groups selected from halogen, oxo (═O), $(C_1-C_6)$alkyl, aryl, and aryl-$(C_1-C_6)$alkyl; notably selected from $(C_1-C_6)$alkyl, aryl, and aryl-$(C_1-C_6)$alkyl.

In the above definitions of $R_{100}$, $R_{101}$, $R_{102}$ and $R_{103}$, the aryl preferably is a phenyl or a naphtyl, notably a phenyl.

In the above definitions of $R_{100}$, $R_{101}$, $R_{102}$ and $R_{103}$, the heterocycle is notably a saturated, unsaturated or aromatic (notably aromatic) hydrocarbon monocycle or bicycle (comprising fused, bridged or spiro rings, notably fused rings), notably a monocycle, each cycle having 5 or 6 members and 1 to 4, notably 1 or 2, carbon atoms having each been replaced with a nitrogen or oxygen atom, notably a nitrogen atom. The heterocycle can be notably chosen among pyrrole, imidazole, pyrazole, triazoles, indole, benzimidazole, indazole, pyridine, pyrimidine, pyridazine, pyrazine, triazine, quinoline, isoquinoline, quinoxaline, quinazoline, piperidine, piperazine, triazinane, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines and tetrahydrotriazines. According to a first embodiment, the heterocycle is chosen among pyrrole, imidazole, pyrazole, triazoles, indole, benzimidazole, indazole, pyridine, pyrimidine, pyridazine, pyrazine, triazine, quinoline, isoquinoline, quinoxaline and quinazoline; notably chosen among pyridine, pyrimidine, pyridazine, pyrazine, triazine, quinoline, isoquinoline, quinoxaline and quinazoline. According to a second embodiment, the heterocycle is chosen among piperidine, piperazine, triazinane or pyrrolidine; and in particular is piperazine.

According to a particular embodiment, the compounds according to the present invention are compounds of formula (I-3c) or (I-4c), such as (I-3c), or a pharmaceutically acceptable salt or solvate thereof, wherein:

n1 and n2 represent, independently of each other, 0, 1, or 2,

Q represents

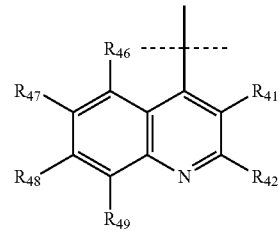

where $R_{40}$ where $R_{41}$, $R_{42}$, $R_{46}$, $R_{47}$, $R_{48}$ and $R_{49}$ each represent, independently of each other, hydrogen, halogen, $OR_{11}$, or $NR_{12}R_{13}$; and notably Q represents

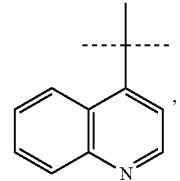

W represents a bond,

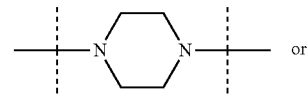

or

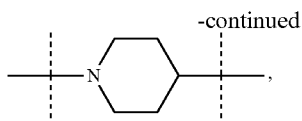

the nitrogen atom being linked to $(CH_2)_{n1}$; notably

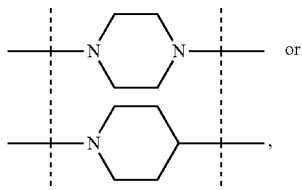

the nitrogen atom being linked to $(CH_2)_{n1}$, and preferably

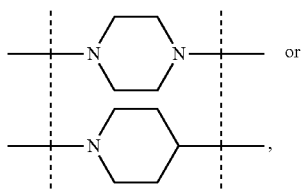

the nitrogen atom being linked to $(CH_2)_{n1}$; notably

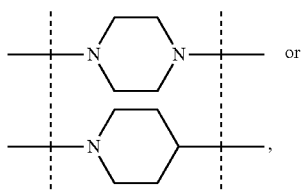

the nitrogen atom being linked to $(CH_2)_{n1}$, $X_1$ represents NH, $X_2$ represents a bond or O, notably O, $Y_1$ and $Y_2$ represent, independently of each other, H, a halogen atom, $OR_{101}$ or $NR_{102}R_{103}$; notably $Y_1$ represents H, a halogen atom or $NR_{102}R_{103}$ and $Y_2$ represents H or $OR_{101}$, provided that at least one of $Y_1$ and $Y_2$ represent a group other than H, where $R_{101}$ represents H, $(C_1\text{-}C_6)$alkyl, aryl or aryl-$(C_1\text{-}C_6)$alkyl; such as H or $(C_1\text{-}C_6)$alkyl, $R_{102}$ and $R_{103}$ represent, independently of one another, H, $(C_1\text{-}C_6)$alkyl, aryl, heterocycle, aryl-$(C_1\text{-}C_6)$alkyl, heterocycle-$(C_1\text{-}C_6)$alkyl or —$((C_1\text{-}C_6)$alkyl$)$-$NR_{104}$-$A_1$, with $A_1$ representing H, $(C_1\text{-}C_6)$alkyl, aryl or heterocycle; notably H or —$((C_1\text{-}C_6)$alkyl$)$-$NR_{104}$-$A_1$, with $A_1$ representing H, $(C_1\text{-}C_6)$alkyl or aryl, such as H or $(C_1\text{-}C_6)$alkyl, or $R_{102}$ and $R_{103}$ form together, with the nitrogen carrying them, a heterocycle, where each aryl and heterocycle moiety is optionally substituted with one or several groups selected from halogen, oxo (=O), $(C_1\text{-}C_6)$alkyl, aryl and aryl-$(C_1\text{-}C_6)$alkyl, $R_4$ represent, independently of each other, aryl heterocycle, aryl-$(C_1\text{-}C_6)$alkyl, heterocycle-$(C_1\text{-}C_6)$alkyl, —$((C_1\text{-}C_6)$alkyl$)$-NH-aryl or —$((C_1\text{-}C_6)$alkyl$)$-NH-heterocycle; notably heterocycle, aryl-$(C_1\text{-}C_6)$alkyl, or —$((C_1\text{-}C_6)$alkyl$)$-NH-aryl, each aryl or heterocycle moiety being optionally substituted with one or several groups selected from halogen, oxo (=O), $(C_1\text{-}C_6)$alkyl, aryl and aryl-$(C_1\text{-}C_6)$alkyl, and $R_5$ represents H, wherein:

the aryl is phenyl or naphtyl, the heterocycle is a saturated hydrocarbon monocycle having 5 or 6 members and 1 to 3, notably 1 or 2, carbon atoms having each been replaced with a nitrogen or oxygen atom, notably a nitrogen atom; such as piperidine, piperazine, triazinane or pyrrolidine; and in particular piperidine or piperazine.

In the above particular embodiment, $R_4$ represents advantageously a group:

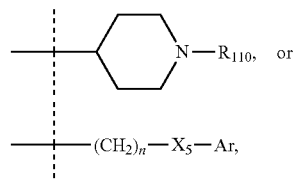

where $R_{110}$ represents an aryl or aryl-$(C_1\text{-}C_6)$alkyl group, such as an aryl-$(C_1\text{-}C_6)$alkyl group, optionally substituted with one or several halogen atoms, n is an integer comprised between 1 and 6, $X_5$ is as defined above and notably is a bond or NH, and Ar is an aryl group such as phenyl or naphtyl, in particular where $R_{110}$ represents a benzyl or naphtylmethyl group optionally substituted with one or several halogen atoms, n is an integer comprised between 1 and 6, $X_5$ is a bond or NH, and Ar is phenyl or naphtyl.

The compounds of the present invention can be selected from compounds A to H, notably from compounds A to G, described in the experimental part below and the pharmaceutically acceptable salts and solvates thereof (notably the hydrochloride thereof).

The present invention relates also to a compound of formula (I) as defined above, for use as a drug, notably intended for the treatment of cancer.

The present invention also relates to the use of a compound of formula (I) as defined above, for the manufacture of a drug, notably intended for the treatment of cancer.

The present invention also relates to a method for the treatment of cancer comprising the administration to a person in need thereof of an effective dose of a compound of formula (I) as defined above.

The cancer may be more particularly colon cancer, breast cancer, kidney cancer, liver cancer, pancreatic cancer, prostate cancer, glioblastoma, non-small cell lung cancer, neuroblastoma, inflammatory myofibroblastic tumor, leukemia (acute myeloid leukemia, myelodysplastic syndrome, chronic myelomonocytic leukemia), melanoma, diffuse B-cell lymphoma or anaplastic large-cell lymphoma.

The present invention relates also to a compound of formula (I) as defined above, for use as a DNA methylation inhibitor, in particular as a DNMT inhibitor.

According to the invention, the expression "DNA methylation inhibitor" and "DNMT inhibitor" refers to molecules that are able to reduce or inhibit the DNA methylation and the DNA methyltransferase activity respectively. Preferentially, the use of a DNMT inhibitor according to the invention makes it possible to suppress the activity of said DNMT.

The present invention also relates to a pharmaceutical composition comprising at least one compound of formula (I) as defined above and at least one pharmaceutically acceptable excipient.

The pharmaceutical compositions according to the invention may be formulated notably for oral administration or for injection, wherein said compositions are intended for mammals, including humans.

The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by the person skilled in the art.

The pharmaceutical compositions according to the invention may further comprise at least one other active ingredient, such as an anticancer agent.

The present invention relates also to a pharmaceutical composition comprising:
(i) at least one compound of formula (I) as defined above, and
(ii) at least one other active ingredient, such as an anticancer agent,
as a combination product for simultaneous, separate or sequential use.

The present invention also relates to a pharmaceutical composition as defined above for use as a drug, notably intended for the treatment of cancer.

The present invention also relates to methods for the preparation of the compounds of formula (I) according to the invention.

A first method is a method to prepare a compound of formula (I) or a pharmaceutically acceptable salt or solvate thereof, in which $W=NR_0$ with $R_0 \neq H$, comprising:
(a) reacting a compound of formula (I) in which $W=NH$ with:
a compound of formula $R_0$-LG where $R_0$ represents a $(C_1$-$C_6)$alkyl optionally substituted with CHO, $CO_2H$ or $CO_2$—$((C_1$-$C_6)$alkyl) and LG represents a leaving group to give a compound of formula (I) in which $W=NR_0$ with $R_0$ representing a $(C_1$-$C_6)$alkyl optionally substituted with CHO, $CO_2H$ or $CO_2$—$((C_1$-$C_6)$alkyl), dimethylformamide (DMF) to give a compound of formula (I) in which $W=NR_0$ with $R_0=CHO$, or
a compound of formula $R_0$-$A_1$ where $R_0$ represents $CO_2$—$((C_1$-$C_6)$alkyl) and $A_1$ represents a $(C_1$-$C_6)$ alkoxy group or a halogen atom (such as Cl or Br) to give a compound of formula (I) in which $W=NR_0$ with $R_0$ representing $CO_2$—$((C_1$-$C_6)$alkyl), and
(b) optionally salifying or solvating the compound obtained in step (a) to give a pharmaceutically acceptable salt or solvate of a compound of formula (I) in which $W=NR_0$ with $R_0$ as defined above.

Step (a):

When $R_0$ Represents a $(C_1$-$C_6)$Alkyl Optionally Substituted with CHO, $CO_2H$ or $CO_2$—$((C_1$-$C_6)$alkyl):

The term "leaving group", as used in the present invention, refers to a chemical group which can be easily replaced with a nucleophile during a nucleophile substitution reaction, the nucleophile being in the case of step (a) a secondary amine, i.e. a molecule carrying a group NH. Such a leaving group can be in particular a halogen atom or a sulfonate. The sulfonate is in particular a group —$OSO_2$—$R_7$ with $R_7$ representing a $(C_1$-$C_6)$alkyl, aryl, aryl-$(C_1$-$C_6)$-alkyl or $(C_1$-$C_6)$-alkyl-aryl group. The sulfonate can be in particular a mesylate ($CH_3$—$S(O_2)O$—), a triflate ($CF_3$—$S(O)_2O$—) or a tosylate (p-Me-$C_6H_4$—$S(O)_2O$—).

The LG group can be in particular a halogen atom such as a bromine.

Step (a) is advantageously carried out in the presence of a base such as triethylamine.

When $R_0$ represents a substituted $(C_1$-$C_6)$alkyl group, the $(C_1$-$C_6)$alkyl group will be advantageously substituted with a $CO_2$—$((C_1$-$C_6)$alkyl) group. This group can then be hydrolysed, notably in the presence of NaOH or KOH, to give a $CO_2H$ group ($R_0$ represents then a $(C_1$-$C_6)$alkyl substituted with $CO_2H$). A reduction step in conditions well known to the one skilled in the art allows obtaining a CHO group ($R_0$ represents then a $(C_1$-$C_6)$alkyl substituted with CHO).

When $R_0$ Represents CHO:

The reaction is advantageously performed using DMF as solvent, notably in the presence of a base such as triethylamine.

When $R_0$ Represents $CO_2$—$((C_1$-$C_6)$Alkyl):

This reaction can be carried out in conditions to prepare carbamates well known to the one skilled in the art.

Step (b):

The salification or solvatation step can be carried out by methods well known to the one skilled in the art, in particular by reaction of the compound of formula (I) obtained in step (a) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (a).

Thus steps (a) and (b) can be carried out in a single step, without isolating intermediate compounds.

A second method is a method to prepare a compound of formula (I) or a pharmaceutically acceptable salt or solvate thereof, in which W represents $NR_0$, a divalent monoglycosyl,

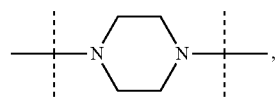

-continued

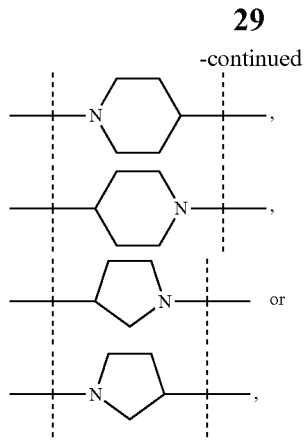

comprising:
(1) reacting a compound of the following formula (II):

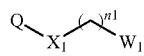
(II)

in which Q, $X_1$ and n1 are as defined above and $W_1$ represents $LG_1$, $NHR_8$, a monovalent monoglycosyl,

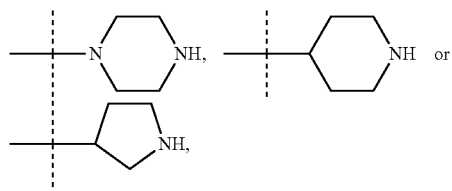

with a compound of the following formula (III):

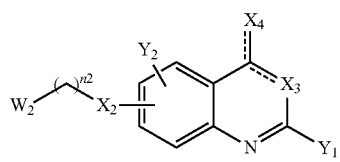
(III)

in which $X_2$, $X_3$, $X_4$, $Y_1$, $Y_2$ and n2 are as defined above and $W_2$ represents $LG_2$, $NHR_8$, a monovalent monoglycosyl,

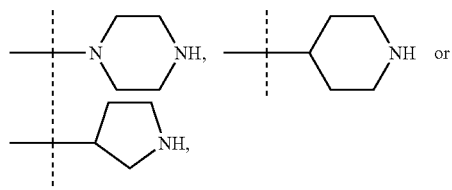

wherein $LG_1$ and $LG_2$ represent, independently of each other, a leaving group and $R_8$ represents $R_0$ or a N-protecting group, on the condition that:
when $W_1$ represents $LG_1$, then $W_2$ represents $NHR_8$, a monovalent monoglycosyl,

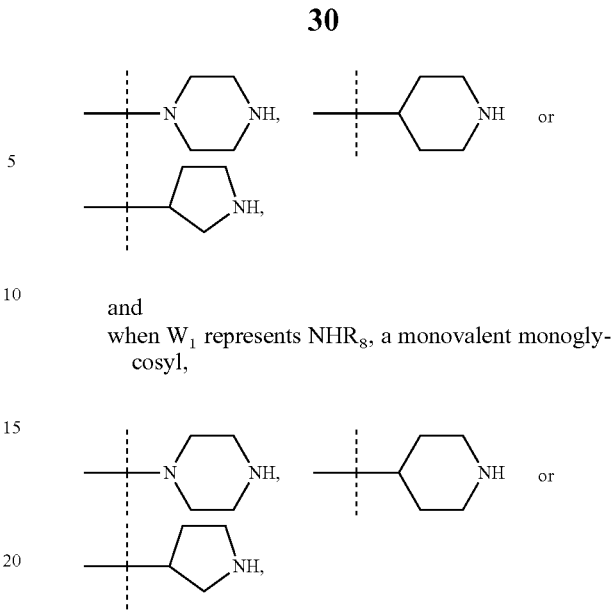

and
when $W_1$ represents $NHR_8$, a monovalent monoglycosyl, then $W_2$ represents $LG_2$,
and, when $W_1$ or $W_2$ represents $NHR_8$ with $R_8$ representing a N-protecting group, deprotecting the nitrogen atom bearing the N-protecting group, to give a compound of formula (I) as defined above, and
(2) optionally salifying or solvating the compound obtained in step (1) to give a pharmaceutically acceptable salt or solvate of a compound of formula (I) as defined above.

Step (1):
The $LG_1$ and $LG_2$ groups can be in particular a halogen atom such as a bromine or chlorine.
The reaction between the compounds of formula (II) and (III) can be carried out in the presence of a base, such as $K_2CO_3$. A catalytic amount of KI can also be added to the reaction medium.
$R_8$ can represent in particular H or a N-protecting group, notably a N-protecting group. When $W_1$ or $W_2$ represents $NHR_8$ with $R_8$ representing H or a N-protecting group, it is possible to prepare compounds of formula (I) with W=NH.
The term "protecting group", as used in the present invention, refers to a chemical group which selectively blocks a reactive site in a multifunctional compound so as to allow selectively performing a chemical reaction on another unprotected reactive site.
The term "N-protecting group", as used in the present invention, refers to those groups intended to protect an amine function (notably a primary amine function) against undesirable reactions (such as a disubstitution of the primary amine function) during synthetic procedures. Commonly used N-protecting groups are disclosed in Greene, "Protective Groups In Organic Synthesis," (John Wiley & Sons, New York (1981)). An amine function protected by a N-protecting group can be a carbamate, an amide, a sulfonamide, an N-alkyl derivative, an amino acetal derivative, a N-benzyl derivative, an imine derivative, an enamine derivative or a N-heteroatom derivative. In particular, N-protecting groups include formyl; benzyl (Bn); —CO—$R_9$ such as acetyl (Ac), pivaloyl (Piv or Pv) or benzoyl (Bz); —CO$_2$—$R_9$ such as tbutyloxycarbonyl (Boc), trichloroethoxycarbonyl (TROC), allyloxycarbonyl (Alloc) or benzyloxycarbonyl (Cbz or Z); —SO$_2$—$R_9$ such as phenylsulfonyl or 2-nitrobenzenesulfonyl (Nos or Ns); and the like, with $R_9$ representing a ($C_1$-$C_6$)alkyl optionally substituted with one or several halogen atoms such as F or Cl; a $(C_2-C_6)$alkenyl such as an allyl; an aryl, such as a phenyl, optionally substituted with $NO_2$; or an aryl-$(C_1-C_6)$alkyl such as a benzyl.

The step of deprotecting the nitrogen atom bearing the N-protecting group can be carried out by methods well known to the one skilled in the art, notably as disclosed in Greene, "Protective Groups In Organic Synthesis," (John Wiley & Sons, New York (1981)).

The N-protecting group will be in particular 2-nitrobenzenesulfonyl (Nos or Ns). It can be deprotected in the presence of thiophenol.

The compounds of formulas (II) and (III) are either commercially available or prepared by methods well known to the one skilled in the art, notably as illustrated in the examples below.

In particular, the compound of formula (II) can be prepared by reacting a compound of formula Q-Hal with a compound of formula $HX_1—(CH_2)_{n1}—W_3$ where:
Q, $X_1$ and n1 are as defined above,
Hal represents a halogen atom such as Cl or Br, and
$W_3$ represents a group $W_1$, optionally in a protected form ($W_3$ can represent notably OH).

This reaction can be performed optionally in the presence of a base.

Further steps of protection(s), deprotection(s) and/or functionalization(s) well known to the one skilled in the art can be carried out, in particular a deprotection step of the $W_3$ group can be carried out to introduce the $W_1$ function on the molecule.

When the compound of formula (III) is a compound of the following formula (IIIc):

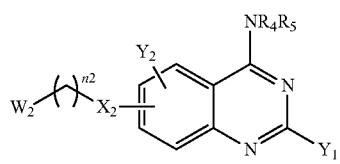

(IIIc)

with $W_2$, $X_2$, $Y_1$, $Y_2$, $R_4$, $R_5$ and n2 as defined above, this compound can be prepared by reacting a compound of the following formula (IV):

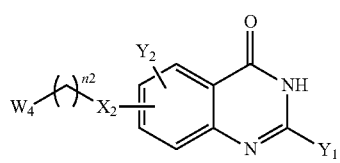

(IV)

with $X_2$, $Y_1$, $Y_2$ and n2 as defined above and $W_4$ representing a group $W_2$, optionally in a protected form,
with an amine of formula $R_4R_5NH$ with $R_4$ and $R_5$ as defined above.

This reaction can be performed in the presence of a base such as $K_2CO_3$, DIPEA or triethylamine.

The carbonyl function of the compound of formula (IV) can be activated in the form of a triazole, notably by reaction with $POCl_3$ and triazole (more particularly 1,2,3-triazole) preferably in the presence of a base such as triethylamine, or also in the form of a halogen, such as a chlorine, notably by reaction with $POCl_3$.

Thus the compound of formula (IIIc) can be prepared by: activating the compound of formula (IV) in the form of a triazole or a halogen atom of the following formula (V):

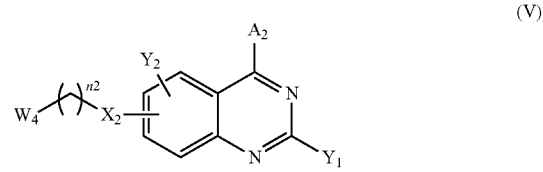

(V)

with $W_4$, $X_2$, $Y_1$, $Y_2$ and n2 as defined above and $A_2$ represents a halogen atom such as Cl or

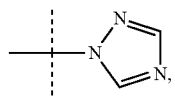

reacting the compound of formula (V) with the amine of formula $R_4R_5NH$.

Further steps of protection(s), deprotection(s) and/or functionalization(s) well known to the one skilled in the art can be carried out, in particular a deprotection step of the $W_4$ group can be carried out to introduce the $W_2$ function on the molecule.

When the compound of formula (III) is a compound of the following formula (IIId):

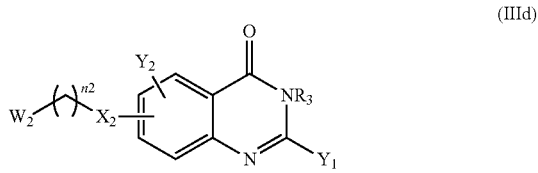

(IIId)

with $W_2$, $X_2$, $Y_1$, $Y_2$, $R_3$ and n2 as defined above, and $R_3 \neq H$, this compound can be prepared by reacting a compound of formula (IV) as defined above with a compound of formula $R_3$-$LG_3$ with $R_3$ as defined above and $LG_3$ representing a leaving group, such as a halogen atom (e.g. Cl or Br).

This reaction can be carried out in the presence of a base, such as $K_2CO_3$. A catalytic amount of KI can also be added to the reaction medium.

Further steps of protection(s), deprotection(s) and/or functionalization(s) well known to the one skilled in the art can be carried out, in particular a deprotection step of the $W_4$ group can be carried out to introduce the $W_2$ function on the molecule.

The compound of formula (IV) can be prepared by reacting a compound of the following formula (VI):

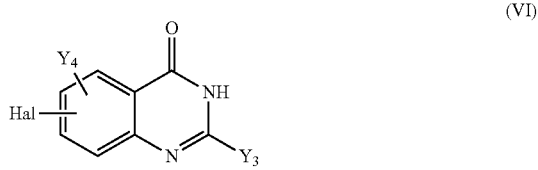

(VI)

where Hal represents a halogen atom such as F, and $Y_3$ and $Y_4$ represent respectively a $Y_1$ or $Y_2$ group optionally in a protected form, with a compound of formula $W_4$—$(CH_2)_{n2}$—$X_2H$ where $W_4$, $X_2$ and n2 are as defined above and $X_2$ is not a bond.

This reaction can be carried out in the presence of a base such as NaH.

Further steps of protection(s), deprotection(s) and/or functionalization(s) well known to the one skilled in the art can be carried out, in particular a deprotection step of the $Y_3$ and $Y_4$ groups can be carried out to introduce the $Y_1$ and $Y_2$ functions on the molecule.

Step (2):

The salification or solvatation step can be carried out by methods well known to the one skilled in the art, in particular by reaction of the compound of formula (I) obtained in step (1) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (1).

Thus steps (1) and (2) can be carried out in a single step, without isolating intermediate compounds.

A third method is a method to prepare a compound of formula (I) or a pharmaceutically acceptable salt or solvate thereof, comprising:

(A) reacting a compound of the following formula (VII):

$$Q\text{-}X_6 \quad (VII)$$

in which Q is as defined above and $X_6$ represents a halogen atom (e.g. Cl or Br) or —$X_1$—$(CH_2)_{n1}$—$W$—$(CH_2)_{n2}$—$X_2H$ with W, $X_1$, $X_2$, n1 and n2 as defined above and $X_2$ is not a bond, with a compound of the following formula (VIII):

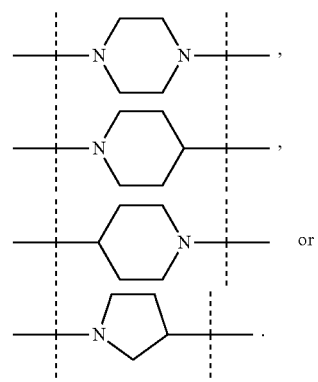

in which $Y_1$, $Y_2$, $X_3$ and $X_4$ are as defined above and $X_7$ represents a halogen atom (e.g. F) or —$X_2$—$(CH_2)_{n2}$—$W$—$(CH_2)_{n1}$—$X_1H$ with W, $X_1$, $X_2$, n1 and n2 as defined above (and can be a bond), on the condition that:

when $X_6$ represents a halogen atom, then $X_7$ represents —$X_2$—$(CH_2)_{n2}$—$W$—$(CH_2)_{n1}$—$X_1H$, and when $X_6$ represents —$X_1$—$(CH_2)_{n1}$—$W$—$(CH_2)_{n2}$—$X_2H$, then $X_7$ represents a halogen atom, to give a compound of formula (I) in which W represents $NR_0$,

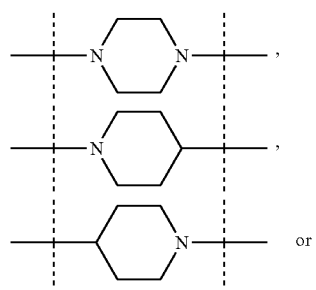

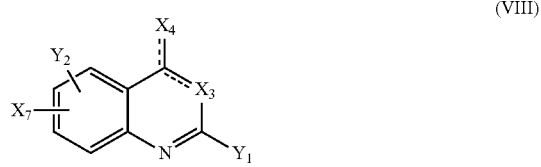

and (B) optionally salifying or solvating the compound obtained in step (A) to give a pharmaceutically acceptable salt or solvate of a compound of formula (I) as defined above in which W represents $NR_0$,

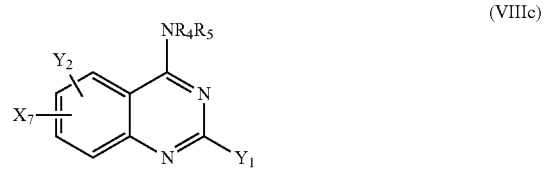

Step (A):

The reaction between the compounds of formula (VII) and (VIII) can be carried out in the presence of a base, such as $K_2CO_3$. A catalytic amount of KI can also be added to the reaction medium.

The compounds of formulas (VII) and (VIII) are either commercially available or prepared by methods well known to the one skilled in the art, notably as illustrated in the examples below.

In particular, the compound of formula (VII), when $X_6$ represents —$X_1$—$(CH_2)_{n1}$—$W$—$(CH_2)_{n2}$—$X_2H$, can be prepared by reacting a compound of formula Q-Hal with a compound of formula $HX_1$—$(CH_2)_{n1}$—$W$—$(CH_2)_{n2}$—$X_8$ where:

Q, $X_1$, W, n1 and n2 are as defined above,

Hal represents a halogen atom such as Cl or Br, and $X_8$ represents a group $X_2H$, optionally in a protected form.

This reaction can be performed optionally in the presence of a base.

Further steps of protection(s), deprotection(s) and/or functionalization(s) well known to the one skilled in the art can be carried out, in particular a deprotection step of the $X_8$ group can be carried out to introduce the $X_2H$ function on the molecule.

When the compound of formula (VIII) is a compound of the following formula (VIIIc):

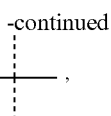

(VIIIc)

with $Y_1$, $Y_2$, $X_7$, $R_4$ and $R_5$ as defined above, this compound can be prepared by reacting a compound of the following formula (IX):

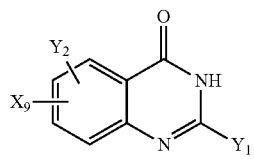

with $Y_1$ and $Y_2$ as defined above and $X_9$ representing a group $X_7$, optionally in a protected form,
with an amine of formula $R_4R_5NH$ with $R_4$ and $R_5$ as defined above.

This reaction can be performed in the presence of a base such as $K_2CO_3$ or triethylamine.

The carbonyl function of the compound of formula (IX) can be activated in the form of a triazole, notably by reaction with $POCl_3$ and triazole (more particularly 1,2,3-triazole) preferably in the presence of a base such as triethylamine, or also in the form of a halogen, such as a chlorine, notably by reaction with $POCl_3$.

Thus the compound of formula (VIIIc) can be prepared by:
activating the compound of formula (IX) in the form of a triazole or a halogen atom of the following formula (X):

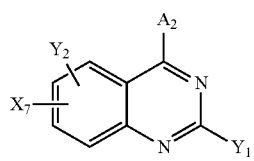

with $Y_1$, $Y_2$ and $X_9$ as defined above and $A_2$ represents a halogen atom such as Cl or

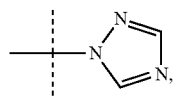

and
reacting the compound of formula (X) with the amine of formula $R_4R_5NH$.

Further steps of protection(s), deprotection(s) and/or functionalization(s) well known to the one skilled in the art can be carried out, in particular a deprotection step of the $X_9$ group can be carried out to introduce the $X_7$ group on the molecule.

When the compound of formula (VIII) is a compound of the following formula (VIIId):

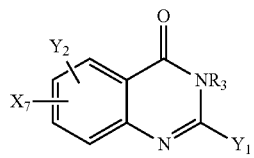

with $Y_1$, $Y_2$, $X_7$ and $R_3$ as defined above, and $R_3 \neq H$, this compound can be prepared by reacting a compound of formula (IX) as defined above with a compound of formula $R_3$-$LG_3$ with $R_3$ as defined above and $LG_3$ representing a leaving group, such as a halogen atom (e.g. Cl or Br).

This reaction can be carried out in the presence of a base, such as $K_2CO_3$. A catalytic amount of KI can also be added to the reaction medium.

Further steps of protection(s), deprotection(s) and/or functionalization(s) well known to the one skilled in the art can be carried out, in particular a deprotection step of the $X_9$ group can be carried out to introduce the $X_7$ group on the molecule.

The compound of formula (IX), when $X_9$ represents $-X_2-(CH_2)_{n2}-W-(CH_2)_{n1}-X_{10}$ where $X_{10}$ represents $X_1H$ optionally in a protected form, can be prepared by reacting a compound of formula (VI) with a compound of formula $HX_2-(CH_2)_{n2}-W-(CH_2)_{n1}-X_{10}$ where W, $X_2$, $X_{10}$, n1 and n2 are as defined above.

This reaction can be carried out in the presence of a base such as NaH.

Step (B):
The salification or solvatation step can be carried out by methods well known to the one skilled in the art, in particular by reaction of the compound of formula (I) obtained in step (A) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (A).

Thus steps (A) and (B) can be carried out in a single step, without isolating intermediate compounds.

A fourth method is a method to prepare a compound of formula (I) or a pharmaceutically acceptable salt or solvate thereof, in which at least one of $Y_1$ and $Y_2$ represents a $OR_{101}$ or $NR_{102}R_{103}$ group, comprising:
(i) reacting a compound of the following formula (XI):

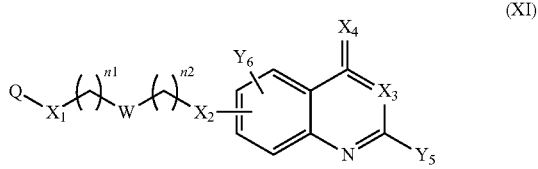

in which $Y_5$ represents $Y_1$ as defined above or a halogen atom such as a chlorine, and $Y_6$ represents $Y_2$ as defined above or a halogen atom such as a chlorine, provided that at least one of $Y_5$ and $Y_6$, and notably $Y_5$, represents a halogen atom such as a chlorine, with $HOR_{101}$ or $HNR_{102}R_{103}$,
to give a compound of formula (I) as defined above where at least one of $Y_1$ and $Y_2$ represents a $OR_{101}$ or $NR_{102}R_{103}$ group, and
(ii) optionally salifying or solvating the compound obtained in step (i) to give a pharmaceutically acceptable salt or solvate of a compound of formula (I) as defined above in which at least one of $Y_1$ and $Y_2$ represents a $OR_{101}$ or $NR_{102}R_{103}$ group.

Step (i):
The reaction between the compounds of formula (XI) and $HOR_{101}$ or $HNR_{102}R_{103}$ can be carried out in the presence of sodium.

The compounds of formulas (XI), $HOR_{101}$ and $HNR_{102}R_{103}$ are either commercially available or prepared by methods well known to the one skilled in the art, notably as illustrated in the examples below.

Step (ii):
The salification or solvatation step can be carried out by methods well known to the one skilled in the art, in particular by reaction of the compound of formula (I) obtained in step (i) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (i).

Thus steps (i) and (ii) can be carried out in a single step, without isolating intermediate compounds.

Further steps of protection(s), deprotection(s) and/or functionalization(s) well known to the one skilled in the art can be carried out to obtain the compounds of formula (I).

The compound according to the present invention obtained by one of the methods described above can be separated from the reaction medium by methods well known to the one skilled in the art, such as by extraction, evaporation of the solvent or by precipitation or crystallisation (followed by filtration).

This compound can also be purified if necessary by methods well known to the one skilled in the art, such as by recrystallization, by distillation, by chromatography on a column of silica gel or by high performance liquid chromatography (HPLC).

The examples which follow illustrate the invention without limiting its scope in any way.

EXAMPLES

The following abbreviations have been used in the following examples.
a.a.: Amino acid
AdoMet: S-Adenosyl-L-methionine
ATP: Adenosine triphosphate
BSA: Bovine Serum Albumin
CMV: Cytomegalovirus
DCM: Dichloromethane
DIAD: Diisopropyl azodicarboxylate
DiPEA: N,N-Diisopropylethylamine
DMF: Dimethylformamide
DMSO: Dimethylsulfoxide
DNA: Deoxyribonucleic acid
EDTA: Ethylenediaminetetraacetic acid
ESI: Electrospray ionisation
HEPES: 4-(2-Hydroxyethyl)-1-piperazineethanesulfonic acid
HPLC: High Performance Liquid Chromatography
HRMS: High Resolution Mass Spectrometry
MS: Mass Spectrometry
MW: Microwave
ND: Not determined
NMR: Nuclear Magnetic Resonance
PBS: Phosphate buffered saline
PBST: Phosphate buffered saline+Tween-20
RPMI: Roswell Park Memorial Institute medium
RT: Room temperature
SAH: S-Adenosyl-L-homocysteine
SAM: S-Adenosyl-L-methionine
TEA: Triethylamine
TFA: Trifluoroacetic acid
Tris: Tris(hydroxymethyl)aminomethane

I. Synthesis of the Compounds According to the Invention

Example 1: Compound A

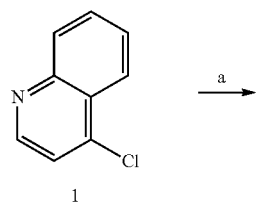

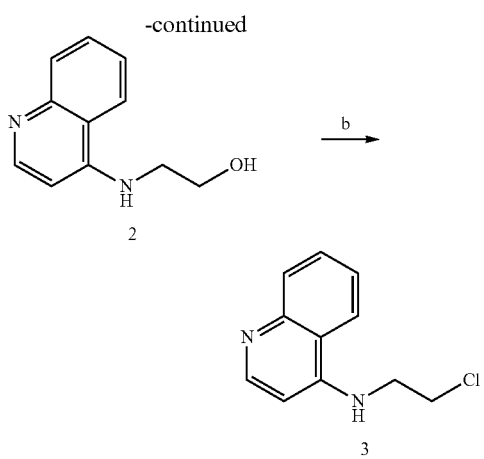

a) Ethanolamine, 125° C., 4 h, quantitative yield. b) SOCl$_2$, DMF cat., Flash boiling, quantitative yield.

4-((2-Hydroxyethyl)amino)quinoline (2)

A mixture of 4-chloroquinoline (360 mg; 2.21 mmol) in ethanolamine (1.5 mL; 22 mmol) was stirred at 110° C. for 3 h. The solvent was removed and the residue was purified by silica gel flash chromatography using a linear gradient of methanol (0→10% MeOH) in dichloromethane to afford 2 as a white powder (414 mg; 2.20 mmol; quantitative yield).

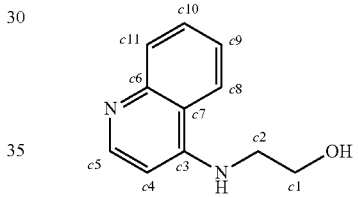

$^1$H NMR (500 MHz, CDCl$_3$) δ 8.38 (d, J=5.4 Hz, 1H, Hc5), 8.19 (dd, J=0.9, 8.3 Hz, 1H, Hc8), 7.77 (dd, J=0.9, 8.3 Hz, 1H, Hc11), 7.59 (ddd, J=1.3, 6.7, 8.3 Hz, 1H, Hc10), 7.40 (ddd, J=1.3, 6.7, 8.3 Hz, 1H, Hc9), 7.07 (brt, J=5.2 Hz, 1H, HOH), 6.46 (d, J=5.4 Hz, 1H, Hc4), 4.83 (brt, J=5.5 Hz, 1H, HNHc), 3.66 (q, J=6.0 Hz, 2H, Hc1), 3.35 (q, J=5.4 Hz, 2H, Hc2).

$^{13}$C NMR (125 MHz, CDCl$_3$) δ 151.1 (Cc5), 150.5 (Cc3), 148.8 (Cc6), 129.5 (Cc8), 129.1 (Cc10), 124.2 (Cc9), 122.1 (Cc11), 119.3 (Cc7), 98.6 (Cc4), 59.3 (Cc1), 45.5 (Cc2).

HRMS-ESI (m/z) calculated for C$_{11}$H$_{13}$N$_2$O [M+H]$^+$: 189.1022. found: 189.1031.

4-((2-chloroethyl)amino)quinoline hydrochloride (3)

2 (360 mg; 1.92 mmol) was solubilized in thionyl chloride (3 ml). The mixture was flash boiled and the solvent was removed. Toluene was added to remove the residual thionyl chloride by co-evaporation. The residue was triturated in dichloromethane and the solid was filtrated to afford 3 as a white solid (360 mg; 1.75 mmol; 91%).

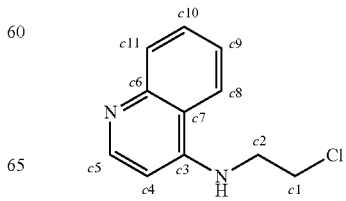

¹H NMR (500 MHz; CDCl₃) δ 8.59 (d, J=5.2 Hz, 1H, Hc5), 8.00 (dd, J=0.7, 8.3 Hz, 1H, Hc8), 7.79 (d, J=8.3 Hz, 1H, Hc11), 7.65 (ddd, J=1.3, 7.9, 8.3 Hz, 1H, Hc10), 7.45 (ddd, J=1.3, 7.0, 8.3 Hz, 1H, Hc9), 6.43 (d, J=5.3 Hz, 1H, Hc4), 5.51 (brs, 1H, HNHc), 3.84 (t, J=5.8 Hz, 2H, Hc1), 3.70 (q, J=5.8 Hz, 2H, Hc1).

¹³C NMR (125 MHz, CDCl₃) δ 151.0 (Cc5), 148.9 (Cc3), 148.5 (Cc6), 130.0 (Cc8), 129.2 (Cc10), 125.0 (Cc9), 119.3 (Cc11), 118.9 (Cc7), 99.0 (Cc4), 44.4 (Cc2), 42.6 (Cc1).

HRMS-ESI (m/z) calculated for $C_{11}H_{13}N_2Cl$ [M+H]⁺: 207.0684. found: 207.0678.

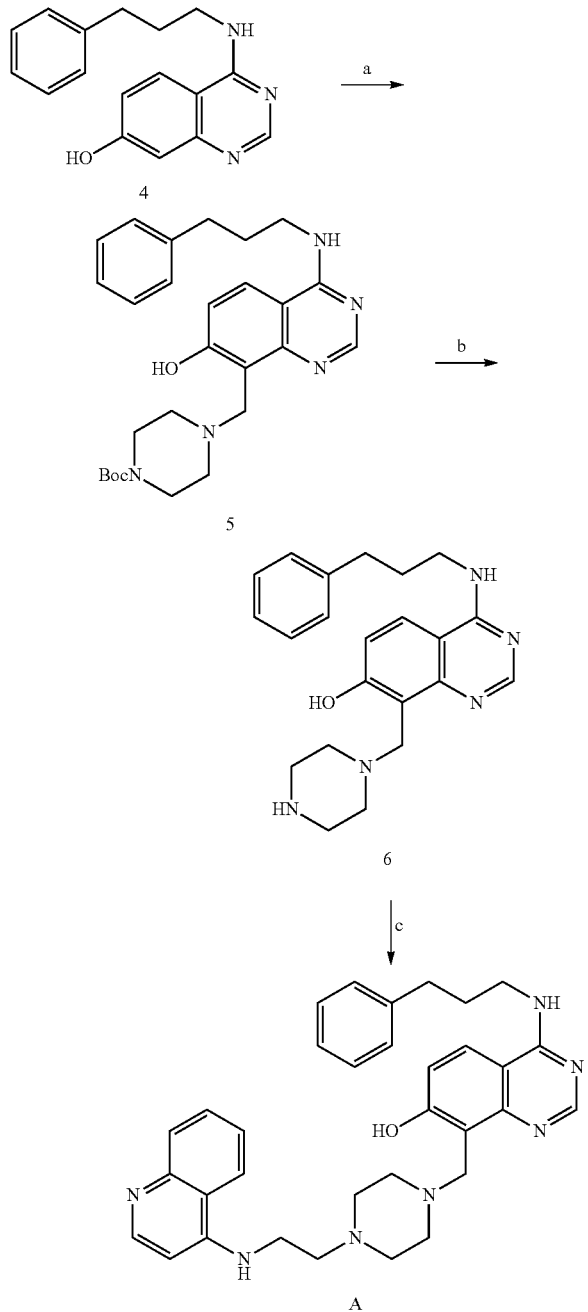

a) N-Boc-piperazine, formaldehyde, isopropanol, 110° C., 1 h, 94%. b) TFA, DCM, RT, 1 h. 97% c) 3, K₂CO₃, KI, DMF, 65° C., 12 h, 23%.

4-((3-phenylpropyl)amino)-8-((N-Boc)piperazin-N4-ylmethy)quinazolin-7-ol (5)

To a solution of compound 4 (purchased from Pharmaron) (195 mg; 0.70 mmol) and N-Boc-piperazine (715 mg; 3.84 mmol) in 6 mL of isopropanol was added paraformaldehyde (160 mg). The reaction mixture was stirred at 110° C. for 1 h. and the solvents were removed and the residue was purified by silica gel flash chromatography using a linear gradient of ethylacetate (0→100% AcOEt) in cyclohexane to afford 5 as a white powder (314 mg; 0.66 mmol; 94%).

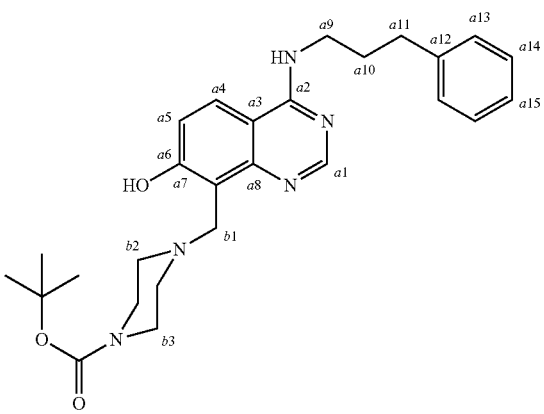 [SMILES: CC(C)(C)OC(=O)N1CCN(Cc2c(O)ccc3c(NCCCc4ccccc4)ncnc23)CC1]

¹H NMR (500 MHz; CDCl₃) δ 8.37 (s, 1H, Hal), 8.05 (d, 1H, J=9.1 Hz, Ha4), 8.02 (t, 1H, J=5.7 Hz, HNH), 7.31-7.22 (m, 4H, Ha13 and Ha14), 7.18 (dt, 1H, J=1.4, 7.1 Hz, Ha15), 6.95 (d, J=9.0 Hz, 1H, Ha5), 4.23 (s, 2H, Hb1), 3.51 (q, J=6.8 Hz, 2H, Ha9), 3.37 (m, 4H, Hb3), 2.67 (t, 2H, J=7.7 Hz, Ha11), 2.49 (m, 4H, Hb2), 1.93 (quint, J=7.3 Hz, 2H, Ha10), 1.40 (s, 9H, HBoc).

¹³C NMR (125 MHz; CDCl₃) δ 162.2 (Ca6), 159.8 (Ca2), 155.3 (Ca1), 154.2 (CBoc), 149.5 (Ca8), 142.2 (Ca12), 128.8 (Ca13), 128.7 (Ca14), 126.2 (Ca15), 122.5 (Ca4), 116.7 (Ca5), 114.0 (Ca7), 108.4 (Ca3), 79.4 (CBoc), 55.7 (Cb1), 54.0 (Cb2), 52.4 (Cb2), 40.5 (Ca9), 33.2 (Ca11), 30.9 (Ca10), 28.5 (CBoc).

HRMS-ESI (m/z) calculated for $C_{27}H_{35}N_5O_3$ [M+Na]⁺: 500.2632. found: 500.2661.

4-((3-phenylpropyl)amino)-8-(piperazin-1-ylmethyl))quinazoline-7ol (6)

A mixture of 5 (314 mg; 0.67 mmol) in TFA was stirred for 1 h at room temperature. TFA was removed. The residue was diluted with dichloromethane and the organic phase was washed with saturated Na₂CO₃. The solvent was removed and 6 was obtained as pale yellow foam (245 mg; 0.65 mmol; 97%).

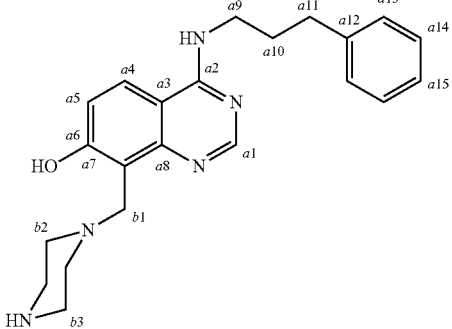

<sup>1</sup>H NMR (500 MHz; CDCl<sub>3</sub>) δ 8.36 (s, 1H, Ha1), 8.02 (d, 1H, J=9.0 Hz, Ha4), 8.00 (t, 1H, J=5.4 Hz, HNH), 7.32-7.221 (m, 4H, Ha13 and Ha14), 7.18 (dt, 1H, J=1.3, 7.2 Hz, Ha15), 6.90 (d, J=9.0 Hz, 1H, Ha5), 4.25 (s, 2H, Hb1), 3.51 (q, J=7.0 Hz, 2H, Ha9), 2.75 (m, 4H, Hb3), 2.67 (t, 2H, J=7.6 Hz, Ha11), 2.48 (m, 4H, Hb2), 1.93 (quint, J=7.2 Hz, 2H, Ha10).

<sup>13</sup>C NMR (125 MHz; CDCl<sub>3</sub>) δ 161.9 (Ca6), 159.8 (Ca2), 155.2 (Ca1), 149.3 (Ca8), 142.2 (Ca12), 128.8 (Ca13), 128.7 (Ca14), 126.2 (Ca15), 123.3 (Ca4), 116.8 (Ca5), 113.6 (Ca7), 108.2 (Ca3), 55.6 (Cb1), 53.8 (Cb2), 45.9 (Cb3), 40.6 (Ca9), 33.2 (Ca11), 30.9 (Ca10).

HRMS-ESI (m/z) calculated for $C_{22}H_{28}N_5O_1$ [M+H]<sup>+</sup>: 378.2288. found: 378.2294.

4-((3-phenylpropyl)amino)-8-((1-(2-(quinolin-4-ylamino)ethyl)piperazin-1-ylmethyl))quinazoline-7-ol (A)

To a solution of 6 (40 mg; 0.11 mmol), K<sub>2</sub>CO<sub>3</sub> (45 mg; 0.33 mmol) and a catalytic amount of KI in DMF (1 mL) was added 3 (57 mg; 0.27 μmol). The mixture was stirred at 65° C. overnight. The solvent was removed and the residue was purified by silica gel flash chromatography using a linear gradient of ammonia 1N in methanol (0→10% MeOH/NH<sub>3</sub>) in dichloromethane or by reversed phase HPLC using a linear acetonitrile gradient with 0.01% of TEA (0→80% CH<sub>3</sub>CN) to afford Compound A as a white pale yellow foam (14 mg; 25 μmol; 23%).

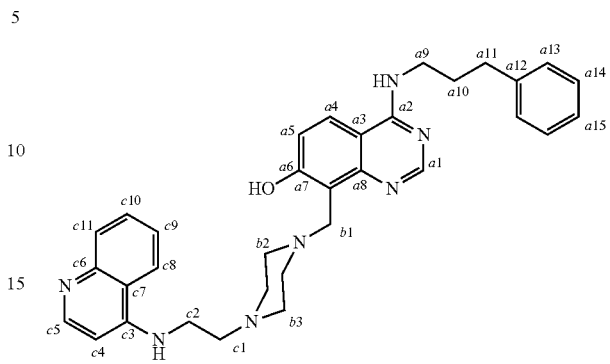

<sup>1</sup>H NMR (500 MHz; CDCl<sub>3</sub>) δ 8.40 (d, J=5.4 Hz, 1H, Hc5), 8.36 (s, 1H, Ha1), 8.16 (d, 1H, J=8.6 Hz, Hc8), 8.02 (d, 1H, J=9.0 Hz, Ha4), 8.00 (m, 1H, HNH), 7.78 (d, J=8.5 Hz, 1H, Hc11), 7.61 (dd, J=0.9, 8.0 Hz, 1H, Hc10), 7.42 (dd, J=0.9, 8.1 Hz, 1H, Hc9), 7.32-7.22 (m, 4H, Ha13 and Ha14), 7.18 (t, 1H, J=7.2 Hz, Ha15), 6.91 (d, J=8.9 Hz, 1H, Ha5), 6.47 (d, J=5.4 Hz, 1H, Hc4), 4.25 (s, 2H, Hb1), 3.86 (brt, J=7.1 Hz, 1H, HNH), 3.52 (q, J=6.2 Hz, 2H, Ha9), 3.40 (q, 2H, J=6.0 Hz, Hc2), 2.71-2.55 (m, 10H, Hc1 and Hb2 and Hb3 and Ha11), 1.93 (quint, J=7.3 Hz, 2H, Ha10).

<sup>13</sup>C NMR (125 MHz; CDCl<sub>3</sub>) δ 161.2 (Ca6), 159.8 (Ca2), 155.2 (Ca1), 151.1 (Cc5), 150.2 (Ca8), 149.4 (Cc3), 148.7 (Cc6), 142.2 (Ca12), 129.5 (Cc8), 129.1 (Cc10), 128.8 (Ca13), 128.7 (Ca14), 126.2 (Ca15), 124.3 (Cc9), 123.4 (Ca4), 121.9 (Cc11), 119.3 (Cc7), 117.0 (Ca5), 113.7 (Ca7), 108.2 (Ca3), 98.7 (Cc4), 55.6 (Cb1), 56.0 (Cc1), 54.6 (Cb2), 52.7 (Cb3), 40.5 (Ca9), 40.1 (Cc2), 33.2 (Ca11), 30.9 (Ca10).

HRMS-ESI (m/z) calculated for $C_{33}H_{38}N_7O_1$ [M+H]<sup>+</sup>: 548.3132; found: 548.3139.

Example 2: Compounds B, C and D

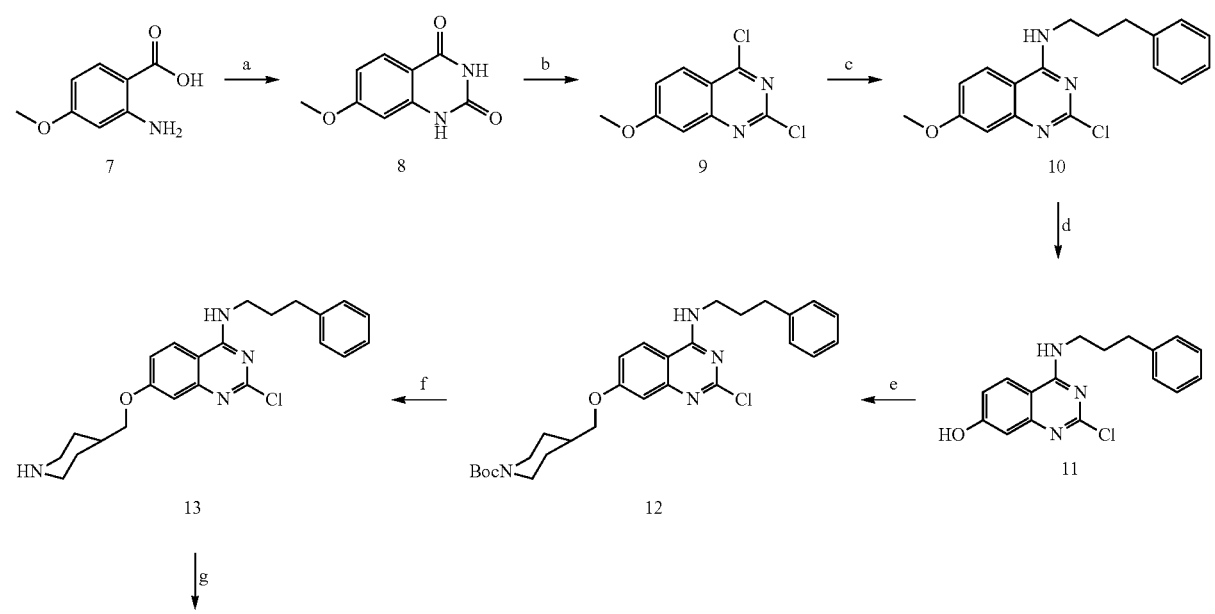

-continued

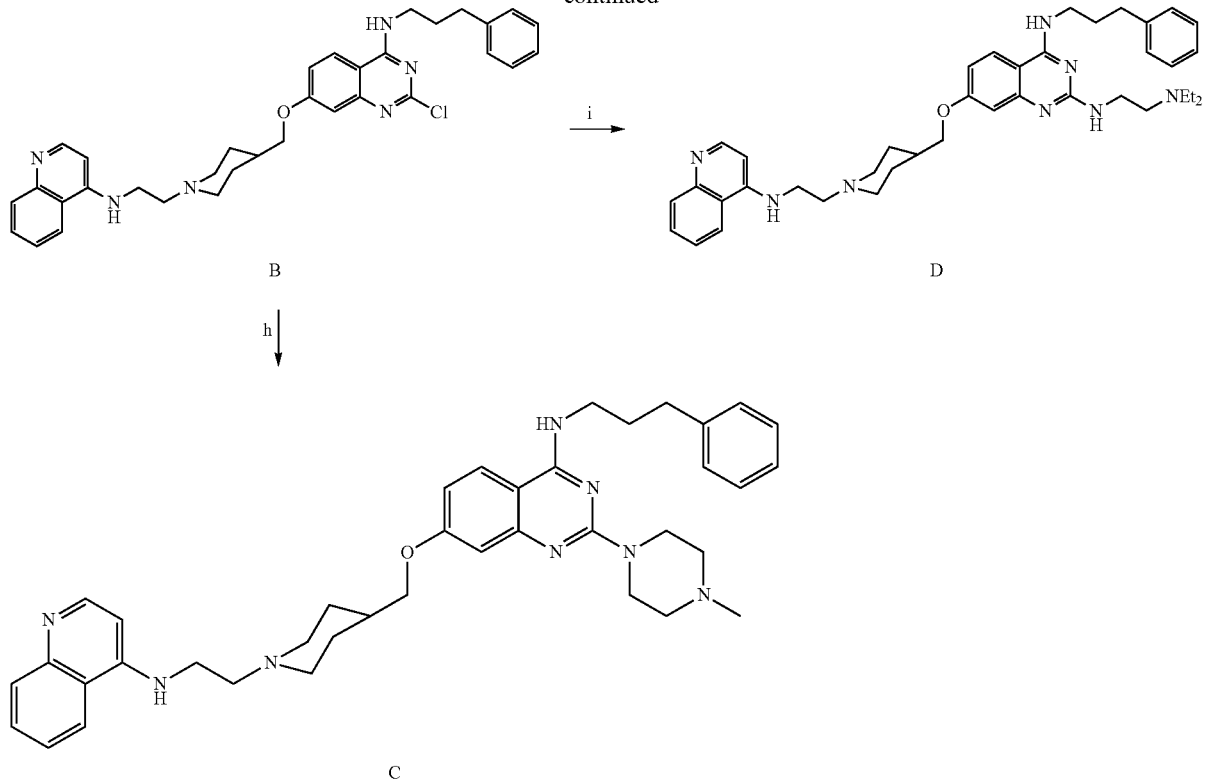

a) Urea, 155° C., 16 h, 48%. b) POCl₃, MeCN, 135° C., 8 h, 54%. c) 3-Phenylpropylamine, DIPEA, DMF, RT, 12 h, 86%. d) BBr₃, DCM, RT, 12 h, 87%. e) N-Boc-piperidine-4-methanol, DIAD, PPh₃, DCM, RT, 18 h, 98%. f) TFA, RT, 1 h, quantitative. g) 3, K₂CO₃, KI, DMF, 65° C., 12 h, 32%. h) 1-methyl-piperazine, 90° C., 2 h, 37%. i) 1. N-diethylethylene diamine, Na, 70° C., 12 h. 2. TFA, MeOH, 36%.

7-methoxyquinazoline-2,4(1H,3H)dione (8)

A mixture of 2-amino-4-methoxybenzoic acid (1 g; 5.98 mmol) and urea (7.18 g; 120 mmol) was stirred at 155° C. for 16 h. The reaction mixture was cooled to 100° C. and then 3 mL of water was added. The mixture was cooled to room temperature and was filtered. 30 mL of 1 mol/L NaOH aqueous solution was added to dissolve the precipitate. After one hour, 4.2 mL of acetic acid was added dropwise and the resulting light brown precipitate was filtered and dried. 8 was obtained as a light brown powder (0.55 g; 2.9 mmol; 48%).

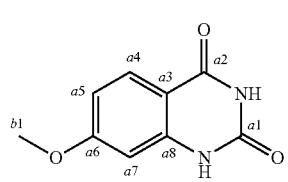

$^1$H NMR (500 MHz; DMSO) δ 11.10 (brs, 1H, HNH), 10.55 (brs, 1H, HNH), 7.8 (d, J=8.63 Hz, 1H, Ha4), 6.77 (dd, J=2.44, 8.84 Hz, 1H, Ha5), 6.64 (d, J=2.43 Hz, 1H, Ha7), 3.82 (s, 3H, Hb1).

$^{13}$C NMR (125 MHz; DMSO) δ 164.8 (Ca6), 162.8 (Ca2), 151 (Ca1), 143.3 (Ca8), 129.3 (Ca4), 111 (Ca5), 108.2 (Ca3), 98.8 (Ca7), 56.1 (Cb1).

HRMS-ESI (m/z) calculated for C₉H₈N₂O₃: 193.0489 [M+H]⁺. found: 193.0511.

2,4-dichloro-7-methoxyquinazoline (9)

7-methoxyquinazoline-2,4(1H,3H)dione (0.31 g; 1.6 mmol) was added to a solution of POCl₃ (10 mL; 107 mmol) in 3 mL of acetonitrile and the mixture was heated to reflux for 8 h. The mixture was poured into ice water and was vigorously stirred and the resulting precipitate was filtered and dried. The precipitate was filtered through silica using dichloromethane to afford 9 as a white powder (0.201 g; 0.88 mmol; 54%).

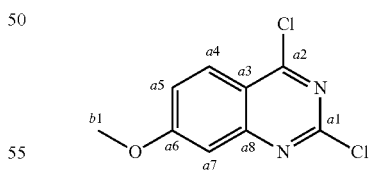

$^1$H NMR (500 MHz; DMSO) δ 8.1 (d, J=9.21 Hz, 1H, Ha4), 7.44 (dd, J=2.08, 9.26 Hz, 1H, Ha5), 7.38 (d, J=2.07 Hz, 1H, Ha7), 3.99 (s, 3H, Hb1).

$^{13}$C NMR (125 MHz; DMSO) δ 166.2 (Ca6), 162.17 (Ca2), 158 (Ca1), 154.9 (Ca8), 127.7 (Ca4), 122.95 (Ca5), 117.2 (Ca3), 106.5 (Ca7), 57 (Cb1).

HRMS-ESI (m/z) calculated for C₉H₆Cl₂N₂O: 227.9918 [M+H]⁺. found: 227.9935.

4-((3-phenylpropyl)amino)-2-chloro-7-methoxyquinazoline (10)

3-Phenyl-1-propylamine (154 μL; 1.1 mmol) was added to a solution of 2,4-dichloro-7-methoxyquinazoline (247 mg; 1.1 mmol) in DMF (3.5 mL) with DIPEA (226 μL; 1.3 mmol). The reaction mixture was stirred at room temperature for 12 h under argon. The resulting mixture was concentrated under vacuum, 1 mL of 1 mol/L NaOH aqueous solution was added to the residue. The residue was taken off with dichloromethane and washed with water and brine, and dried over sodium sulphate. The solvent was removed and the residue was purified by silica gel flash chromatography using a linear gradient of ethyl acetate (0→100% AcOEt) in cyclohexane to afford 10 as a white powder (302 mg; 0.92 mmol; 86%).

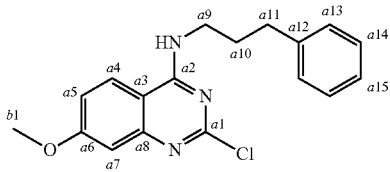

1H NMR (500 MHz; DMSO) δ 8.54 (brt, J=5.28 Hz, 1H, HNH), 8.17 (d, J=9.14 Hz, 1H, Ha4), 7.31-7.24 (m, 4H, Ha13 and Ha14), 7.20-7.16 (m, 1H, Ha15), 7.13 (dd, J=2.49, 8.95 Hz, 1H, Ha5), 7.05 (d, J=2.55 Hz, 1H, Ha7), 3.88 (s, 3H, Hb1), 3.50 (q, J=6.7 Hz, 2H, Ha9), 2.68 (t, J=7.77 Hz, 2H, Ha11), 1.96 (q, J=7.4 Hz, 2H, Ha10),
13C NMR (125 MHz; DMSO) δ 163.6 (Ca6), 161.2 (Ca2), 157.9 (Ca1), 153.1 (Ca8), 142 (Ca12), 128.8 (Ca13), 128.7 (Ca14), 126.2 (Ca15), 125 (Ca4), 117.2 (Ca5), 108 (Ca3), 107 (Ca7), 56.1 (Cb1), 40.8 (Ca9), 32.9 (Ca11), 30.4 (Ca10).
HRMS-ESI (m/z) calculated for $C_{18}H_{18}ClN_3O$: 327.1105 $[M+H]^+$. found: 327.1149.

4-((3-phenylpropyl)amino)-2-chloroquinazolin-7-ol (11)

10 (260 mg; 0.83 mmol) was added to a solution of 0.6 mol/L of boron tribromide in dichloromethane (5.6 mL). The reaction mixture was stirred at room temperature for 12 h under argon. The resulting mixture was quenched with $H_2O$ and concentrated under vacuum. The residue was diluted with ammonia 7N in methanol and the solvent was removed. The crude product was purified by silica gel flash chromatography using a linear gradient of ethyl acetate (0→70% AcOEt) in cyclohexane to afford 11 as a white powder (217 mg; 0.69 mmol; 87%)

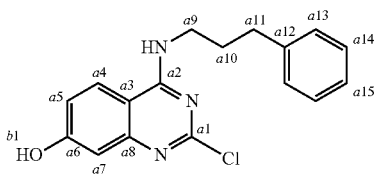

1H NMR (500 MHz; DMSO) δ 10.5 (s, 1H, Hb1), 8.44 (brt, J=5.43 Hz, 1H, HNH), 8.10 (d, J=9.14 Hz, 1H, Ha4), 7.31-7.23 (m, 4H, Ha13 and Ha14), 7.20-7.16 (m, 1H, Ha15), 6.99 (dd, J=2.44, 8.56 Hz, 1H, Ha5), 6.85 (d, J=2.53 Hz, 1H, Ha7), 3.48 (q, J=6.06 Hz, 2H, Ha9), 2.67 (t, J=7.51 Hz, 2H, Ha11), 1.94 (q, J=7.42 Hz, 2H, Ha10),
13C NMR (125 MHz; DMSO) δ 162.3 (Ca6), 161.1 (Ca2), 157.8 (Ca1), 153 (Ca8), 142 (Ca12), 128.8 (Ca13), 128.7 (Ca14), 126.2 (Ca15), 125.3 (Ca4), 117.3 (Ca5), 109.4 (Ca3), 107 (Ca7), 40.7 (Ca9), 32.9 (Ca11), 30.4 (Ca10).
HRMS-ESI (m/z) calculated for $C_{17}H_{16}ClN_3O$: 313.1035 $[M+H]^+$. found: 313.1012.

4-((3-phenylpropyl)amino)-2-chloro-7-(O—((N-Boc)piperidin-4-ylmethoxy)) quinazoline (12)

To a solution of 11 (200 mg; 0.64 mmol) in dichloromethane (2.1 mL), triphenylphosphine (185 mg; 0.7 mmol), (N-Boc)piperidin-4-ylmethanol (145 mg; 0.67 mmol) were added under argon. Diisopropylazodicarboxylate (139 μL; 0.7 mmol) was added dropwise. The reaction mixture was stirred at room temperature for 18 h. The residue was diluted with dichloromethane and washed with water and brine, and dried over sodium sulphate. The solvent was removed and the residue was purified by silica gel flash chromatography using a linear gradient of ethyl acetate (0→50% AcOEt) in cyclohexane to afford 12 as a yellow oil (320 mg; 0.63 mmol; 98%).

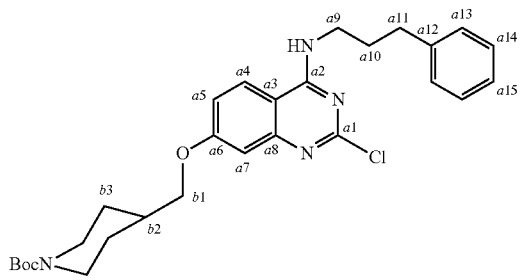

1H NMR (500 MHz; DMSO) δ 8.52 (brt, J=5.69 Hz, 1H, HNH), 8.17 (d, J=9.17 Hz, 1H, Ha4), 7.32-7.24 (m, 4H, Ha13 and Ha14), 7.20-7.16 (m, 1H, Ha15), 7.13 (dd, J=2.72, 9.25 Hz, 1H, Ha5), 7.03 (d, J=2.8 Hz, 1H, Ha7), 4.03-3.93 (m, 4H, Hb1 and Hb4eq), 3.5 (q, J=6.37 Hz, 2H, Ha9), 2.81-2.7 (m, 2H, Hb4ax), 2.68 (t, J=7.68 Hz, 2H, Ha11), 1.99-1.91 (m, 1H, Hb2), 1.96 (q, J=7.17 Hz, 2H, Ha10), 1.8-1.73 (m, 2H, Hb3eq), 1.40 (s, 9H, HBoc), 1.22-1.13 (m, 2H, Hb3ax).
13C NMR (125 MHz; DMSO) δ 162.9 (Ca6), 161.1 (Ca2), 157.9 (Ca1), 154.3 (Ca8), 142 (Ca12), 128.7 (Ca13), 128.6 (Ca14), 126.2 (Ca15), 125.2 (Ca4), 117.4 (Ca5), 107.8 (Ca7), 107.6 (Ca3), 78.9 (CBoc), 72.5 (Cb1), 55.3 (Cb4), 40.8 (Ca9), 35.6 (Cb2), 32.9 (Ca11), 30.4 (Ca10), 28.6 (Cb3), 28.5 (CBoc).
HRMS-ESI (m/z) calculated for $C_{28}H_{35}ClN_4O_3$: 511.1810 $[M+H]^+$. found: 511.1824.

4-((3-phenylpropyl)amino)-2-chloro-7-O-(1H—N-piperidin-4-ylmethoxy) quinazoline (13)

12 (320 mg; 0.63 mmol) in TFA (5 mL) was stirred at room temperature for 1 h. TFA was removed and the resulting mixture was solubilized in ammonia 7N in methanol. The solvent was removed and the residue was diluted with ethyl acetate and the organic phase was washed with saturated $K_2CO_3$ and dried over sodium sulphate. The solvent was removed and 13 was obtained as a white power (260 mg; 0.63 mmol; quantitative).

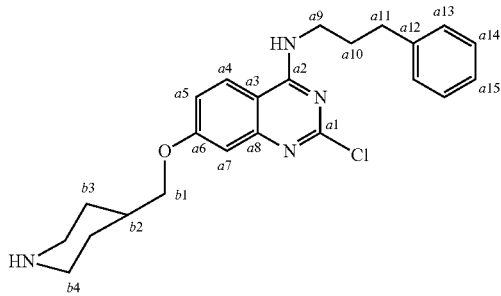

$^{1}$H NMR (500 MHz; DMSO) δ 8.5 (brt, J=5.45 Hz, 1H, HNH), 8.12 (d, J=9.10 Hz, 1H, Ha4), 7.35-7.22 (m, 4H, Ha13 and Ha14), 7.21-7.15 (m, 1H, Ha15), 7.11 (dd, J=2.65, 9.3 Hz, 1H, Ha5), 7.01 (d, J=2.75 Hz, 1H, Ha7), 3.97 (d, J=5.65 Hz, 2H, Hb1), 3.47 (q, J=6.1 Hz, 2H, Ha9), 3.00 (brd, 2H, Hb4eq), 2.15 (m, 2H, Hb4ax), 2.68 (t, J=7.68 Hz, 2H, Ha11), 2.05 (q, J=7.25 Hz, 2H, Ha10), 1.92-1.73 (m, 3H, Hb3eq and Hb2), 1.28-1.19 (m, 2H, Hb3ax).

$^{13}$C NMR (125 MHz; DMSO) δ 162.8 (Ca6), 161 (Ca2), 157.7 (Ca1), 154.3 (Ca8), 142.1 (Ca12), 128.7 (Ca13), 128.6 (Ca14), 126.1 (Ca15), 125.3 (Ca4), 117.4 (Ca5), 107.8 (Ca7), 107.6 (Ca3), 72.3 (Cb1), 53.2 (Cb4), 40.8 (Ca9), 35.6 (Cb2), 32.9 (Ca11), 30.6 (Ca10), 28.5 (Cb3).

HRMS-ESI (m/z) calculated for $C_{23}H_{27}ClN_4O$: 411.1914 $[M+H]^+$. found: 411.1938.

4-((3-phenylpropyl)amino)-2-chloro-7-((1-(2-(quinolin-4-ylamino)ethyl) piperidin-4-yl)methoxy)quinazoline (B)

To a solution of 13 (250 mg; 0.6 mmol), $K_2CO_3$ (168 mg; 1.22 mmol) and a catalytic amount of KI in DMF (3.3 mL) was added 3 (251 mg; 1.22 mmol). The mixture was stirred at 65° C. overnight then was diluted with ethyl acetate. The organic phase was washed with water and brine and dried over sodium sulfate. The solvent was removed and the residue was purified by silica gel flash chromatography using a linear gradient of ammonia 1N in methanol (0→10% MeOH/NH$_3$) in dichloromethane or by reversed phase HPLC using a linear acetonitrile gradient with 0.01% of TEA (0→80% CH$_3$CN) to afford Compound B as a white powder (113 mg; 0.19 mmol; 32%).

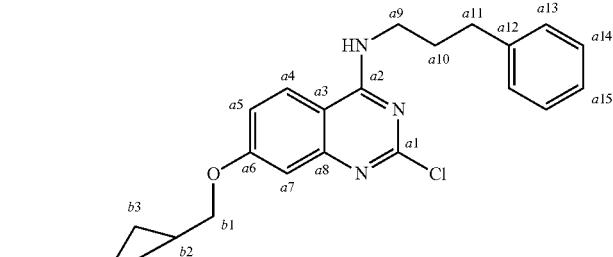
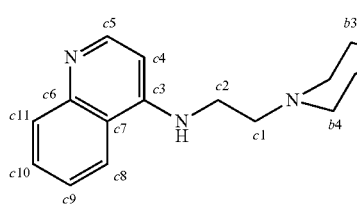

$^{1}$H NMR (500 MHz; DMSO) δ 8.53 (brt, J=5.4 Hz, 1H, HNH), 8.4 (d, J=5.58 Hz, 1H, Hc5), 8.19-8.1 (m, 2H, Hc8 and Ha4), 7.78 (dd, J=1.13, 8.56 Hz, 1H, Hc11), 7.61 (m, 1H, Hc10), 7.43 (m, 1H, Hc9), 7.32-7.17 (m, 5H, Ha13, Ha14 and Ha15), 7.15 (dd, J=2.52, 9 Hz, 1H, Ha5), 7.03 (d, J=2.55 Hz, 1H, Ha7), 7.02 (brt, 1H, HNH), 6.48 (d, J=5.58 Hz, 1H, Hc4), 3.99 (d, J=6.12 Hz, 2H, Hb1), 3.5 (q, J=6.12 Hz, 2H, Ha9), 3.41 (q, J=6.66 Hz, 2H, Hc2), 3.00 (brd, J=11.7 Hz, 2H, Hb4eq), 2.68 (t, J=7.92 Hz, 2H, Ha11), 2.63 (t, J=7.02 Hz, 2H, Hc1), 2.06 (m, 2H, Hb4ax), 1.96 (m, 2H, Ha10), 1.85-1.75 (m, 3H, Hb3eq and Hb2), 1.29-1.2 (m, 2H, Hb3ax).

$^{13}$C NMR (125 MHz; DMSO) δ 163.1 (Ca6), 161.2 (Ca2), 157.9 (Ca1), 156.6 (Cc3), 153.1 (Ca8), 151.2 (Cc5), 150.2 (Cc7), 148.7 (Cc6), 142 (Ca12), 129.5 (Cc11), 129.2 (Cc10), 128.8 (Ca13), 128.7 (Ca14), 126.2 (Ca15), 125.1 (Ca4), 124.3 (Cc9), 121.9 (Cc8), 117.4 (Ca5), 107.9 (Ca7), 107.6 (Ca3), 98.7 (Cc4), 72.8 (Cb1), 56.6 (Cc1), 53.5 (Cb4), 40.8 (Ca9), 40.5 (Cc2), 35.6 (Cb2), 32.9 (Ca11), 30.4 (Ca10), 29 (Cb3).

HRMS-ESI (m/z) calculated for $C_{34}H_{37}ClN_6O$: 581.1932 $[M+H]^+$. found: 581.1929.

4-((3-phenylpropyl)amino)-7-((1-(2-(quinolin-4-ylamino)ethyl)piperidin-4-yl)methoxy)-2-(4-methylpiperazin-1-yl)quinazoline (C)

A solution of 13 (7 mg; 12 μmol) in 1-methylpiperazine (100 μL, 0.9 mmol) was heated at 90° C. for 2 h. The resulting mixture was concentrated under vacuum and the residue was purified by reversed phase HPLC using a linear acetonitrile gradient with 0.01% of TEA (0→80% CH$_3$CN) to afford Compound C as a white powder (2.9 mg; 4.5 μmol; 37%).

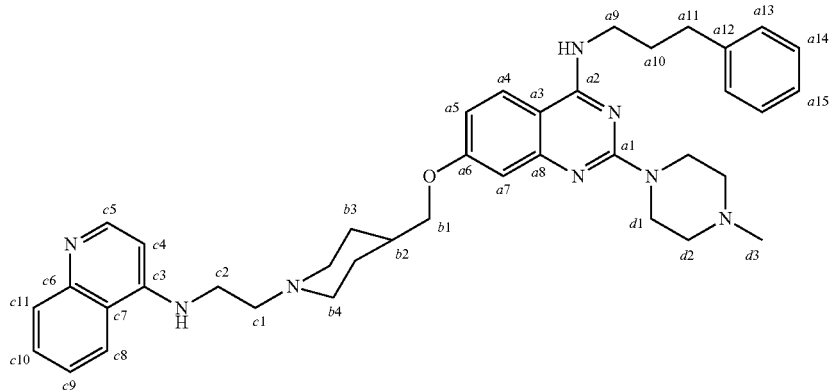 [SMILES: CN1CCN(c2nc(NCCCc3ccccc3)c3ccc(OCC4CCN(CCNc5ccnc6ccccc56)CC4)cc3n2)CC1]

$^1$H NMR (500 MHz; DMSO) δ 8.4 (d, J=5.31 Hz, 1H, Hc5), 8.15 (dd, J=1.1, 8.65 Hz, 1H, Hc8), 7.9 (d, J=9.58 Hz, 1H, Ha4), 7.8 (brt, J=5.63 Hz, 1H, HNH), 7.78 (dd, J=1.15, 8.57 Hz, 1H, Hc11), 7.61 (m, 1H, Hc10), 7.43 (m, 1H, Hc9), 7.31-7.16 (m, 5H, Ha13, Ha14 and Ha15), 7.05 (brt, 1H, HNH), 6.68-6.6 (m, 2H, Ha5 and Ha7), 6.48 (d, J=5.3 Hz, 1H, Hc4), 3.99 (d, J=5.96 Hz, 2H, Hb1), 3.72-3.65 (m, 4H, Hd1), 3.45 (q, J=5.84 Hz, 2H, Ha9), 3.41 (q, J=6.31 Hz, 2H, Hc2), 3.00 (brd, J=11.26 Hz, 2H, Hb4eq), 2.66 (t, J=7.28 Hz, 2H, Ha11), 2.63 (t, J=7.02 Hz, 2H, Hc1), 2.33-2.28 (m, 4H, Hd2), 2.21 (s, 3H, Hd3), 2.05 (m, 2H, Hb4ax), 1.92 (m, 2H, Ha10), 1.81-1.74 (m, 3H, Hb3eq and Hb2), 1.4-1.29 (m, 2H, Hb3ax).

$^{13}$C NMR (125 MHz; DMSO) δ 162.3 (Ca6), 159.9 (Ca2), 159.4 (Ca1), 154.3 (Cc3), 153.5 (Ca8), 151.2 (Cc5), 150.2 (Cc7), 148.7 (Cc6), 142 (Ca12), 129.5 (Cc11), 129.1 (Cc10), 128.8 (Ca13), 128.6 (Ca14), 126.1 (Ca15), 124.6 (Ca4), 124.3 (Cc9), 121.9 (Cc8), 111.9 (Ca5), 105.9 (Ca7), 105.2 (Ca3), 98.7 (Cc4), 72.4 (Cb1), 56.5 (Cc1), 55.1 (Cd2), 53.4 (Cb4), 46.5 (Cd3), 43.6 (Cd1), 40.3 (Ca9), 40.6 (Cc2), 35.7 (Cb2), 33.2 (Ca11), 30.7 (Ca10), 29.1 (Cb3).

HRMS-ESI (m/z) calculated for C$_{39}$H$_{48}$N$_8$O: 645.4024 [M+H]$^+$. found: 645.4015.

4-((3-phenylpropyl)amino)-N$^2$-(2-(diethylamino)ethylenediamine)-7-((1-(2-(quinolin-4-ylamino)ethyl)piperidin-4-yl)methoxy)quinazoline (D)

To dry N,N-diethylethylenediamine (200 μL; 1.4 mmol) was added sodium (5 mg; 0.22 mmol) and the mixture was stirred under utrasonication until complete disparition of sodium fragments (10 to 15 min) then 13 (9 mg; 15 μmol) in N,N-diethylethylenediamine (50 μL) was added and the reaction mixture was stirred at 70° C. for 12 h. The mixture was diluted with methanol (1 ml) and TFA (17 μL, 022 mmol) was added. The solution was purified by reversed phase HPLC using a linear acetonitrile gradient with 0.02% of TFA (0→50% CH$_3$CN) to afford Compound D as a white powder (3.6 mg; 5.5 μmol; 36%).

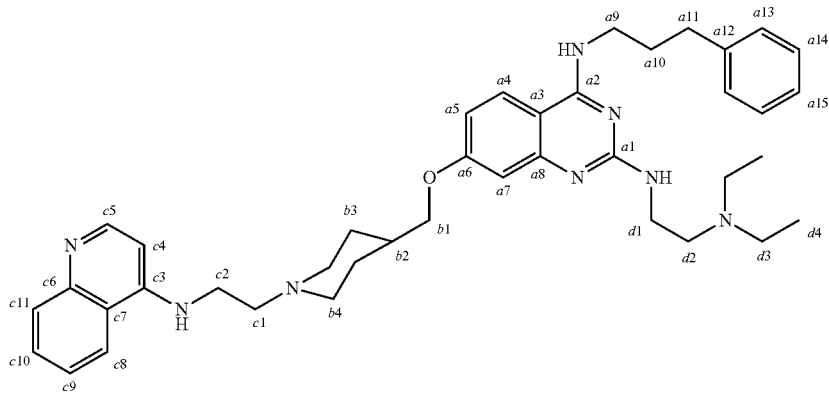 [SMILES: CCN(CC)CCNc1nc(NCCCc2ccccc2)c2ccc(OCC3CCN(CCNc4ccnc5ccccc45)CC3)cc2n1]

¹H NMR (500 MHz; DMSO) δ 8.40 (d, J=5.34 Hz, 1H, Hc5), 8.15 (dd, J=1.04, 8.4 Hz, 1H, Hc8), 7.9 (d, J=9.18 Hz, 1H, Ha4), 7.78 (dd, J=1.09, 8.25 Hz, 1H, Hc11), 7.61 (m, 1H, Hc10), 7.43 (m, 1H, Hc9), 7.32-7.20 (m, 5H, Ha13, Ha14 and Ha15), 7.05 (brt, 1H, HNH), 6.69-6.59 (m, 2H, Ha5 and Ha7), 6.48 (d, J=5.39 Hz, 1H, Hc4), 3.94-3.87 (m, 2H, Hb1), 3.68 (m, 2H, Hd1), 3.49-3.42 (m, 4H, Ha9 and Hc2), 3.00 (brd, J=11 Hz, 2H, Hb4eq), 2.66 (t, J=7.12 Hz, 2H, Ha11), 2.63 (t, J=7.32 Hz, 2H, Hc1), 2.3 (brt, 2H, Hd2), 2.05 (m, 2H, Hb4ax), 1.92 (m, 2H, Ha10), 1.81-1.74 (m, 3H, Hb3eq and Hb2), 1.4-1.33 (m, 2H, Hb3ax), 0.97 (m, 6H, Hd4).

¹³C NMR (125 MHz; DMSO) δ 162.2 (Ca6), 159.9 (Ca2), 159.4 (Ca1), 154.3 (Cc3), 153.5 (Ca8), 151.3 (Cc5), 150.2 (Cc7), 148.7 (Cc6), 142 (Ca12), 129.5 (Cc11), 129.1 (Cc10), 128.8 (Ca13), 128.6 (Ca14), 126.1 (Ca15), 124.4 (Ca4), 124.3 (Cc9), 122 (Cc8), 111.9 (Ca5), 105.9 (Ca7), 105.2 (Ca3), 98.7 (Cc4), 72.3 (Cb1), 56.6 (Cc1), 55.2 (Cd2), 53.5 (Cb4), 43.7 (Cd1), 40.3 (Ca9), 40.6 (Cc2), 35.7 (Cb2), 33.2 (Ca11), 30.9 (Ca10), 29.1 (Cb3), 12.4 (Cd4).

HRMS-ESI (m/z) calculated for $C_{40}H_{52}N_8O$: 661.4321 $[M+H]^+$. found: 661.4317.

Example 3: Compounds E and F

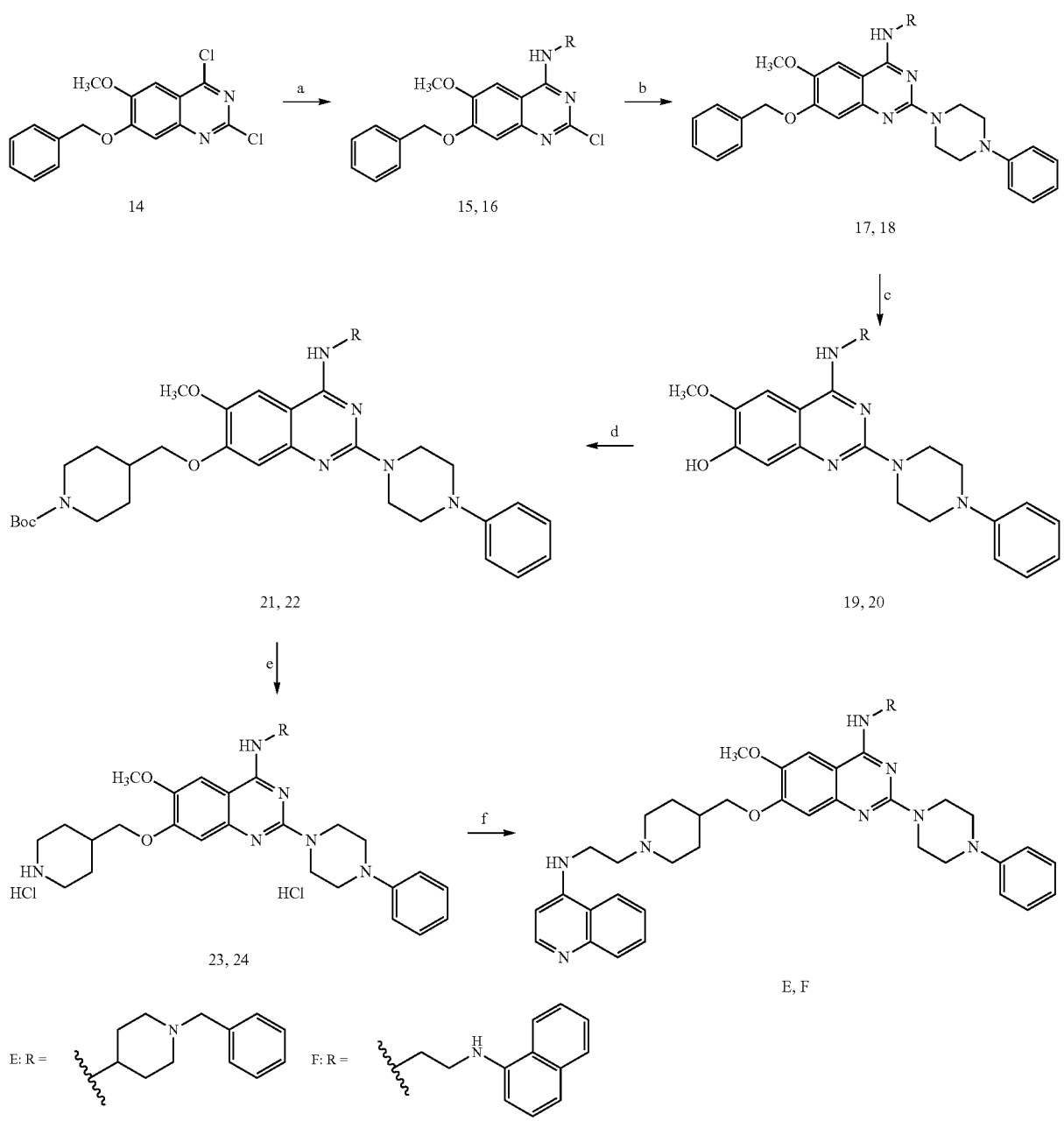

a) R—NH₂, TEA, dry THF, 0° C. to RT, 71 h, 90-94%. b) N-phenylpiperazine, 110° C., sealed tube, 4 h, 80-83%. c) TFA, 0° C. to 115° C., 35 min, quantitative yield.
d) N-Boc-4-(hydroxylmethyl)piperidine, PPh₃, DIAD, dry THF, 0° C. to RT, N₂, 26 h, 75-95%. e) HCl 4N in dioxane, dry MeOH, dry THF, 0° C., to RT, 23-49 h, quantitative yield. f) N-(2-bromoethyl)quinoline-4-amine, NaI, K₂CO₃, dry DMF, 65° C., 27-29 h, 60-65%.

General Procedure for the Preparation of the Intermediates 15 and 16

7-(benzyloxy)-N-(1-benzylpyperidin-4-yl)-2-chloro-6-methoxyquinazolin-4-amine (15)

To a solution of 14 (1.79 mmol, 600 mg, 1 eq.) in dry THF (11.5 mL) were added in sequence TEA (5.37 mmol, 543.4 mg, 0.748 mL, 3 eq.) and 4-amine-1-benzylpiperidine (2.33 mmol, 442.8 mg, 0.438 mL, 1.3 eq.) and the resulting reaction mixture was stirred at room temperature for 23 h. After three further additions of 4-amine-1-benzylpiperidine at 24 h (0.3 eq., 0.1 mL), 48 h (0.3 eq., 0.1 mL), and 55 h (0.75 eq., 0.25 mL) the mixture was filtered after 71 h. The filtrate and the washings were concentrated in vacuum and the crude solid triturated with petroleum ether, collected by filtration, washed with petroleum ether and dried under vacuum. The crude was finally purified by a silica gel column eluting with AcOEt to get 15 as a white powder (822 mg, 94%).

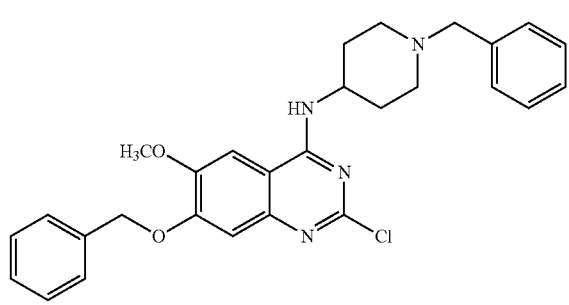 [SMILES: COc1cc2c(NC3CCN(Cc4ccccc4)CC3)nc(Cl)nc2cc1OCc1ccccc1]

M.p.: 155-158° C. $^1$H-NMR (400 MHz; DMSO) δ 1.63-1.72 (m, 2H, 2×CH piperidine ring), 1.89-1.91 (m, 2H, 2×CH piperidine ring), 2.05-2.10 (m, 2H, 2×CH piperidine ring), 2.87-2.89 (m, 2H, 2×CH piperidine ring), 3.51 (s, 2H, NCH$_2$Ph), 3.90 (s, 3H, OCH$_3$), 4.09-4.13 (broad, 1H, NHC$_4$—H-piperidine ring), 5.23 (s, 2H, OCH$_2$Ph), 7.15 (s, 1H, CH quinazoline ring), 7.26-7.28 (m, 1H, NH), 7.31-7.38 (m, 5H, CH phenyl rings), 7.40-7.43 (t, 2H, CH phenyl rings), 7.47-7.49 (d, 2H, CH phenyl rings) 7.67 (s, 1H, CH quinazoline ring), 8.03-8.05 (d, 1H, CH phenyl ring).

N$^1$-(7-(benzyloxy)-2-chloro-6-methoxyquinazolin-4-yl)-N$^2$-(naphtalen-1-yl)ethane-1,2-diamine (16)

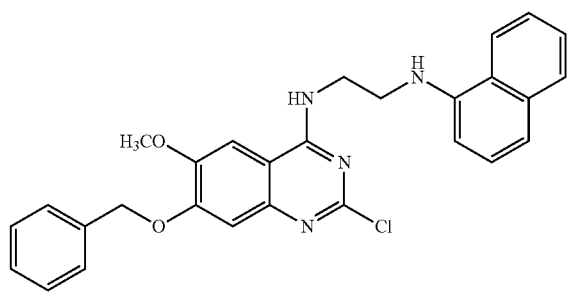 [SMILES: COc1cc2c(NCCNc3cccc4ccccc34)nc(Cl)nc2cc1OCc1ccccc1]

M.p.: 110-111° C. $^1$H-NMR (400 MHz; CDCl$_3$) δ 3.67-3.70 (t, 2H, NHCH$_2$CH$_2$NH-napht), 3.89 (s, 3H, OCH$_3$), 4.09-4.12 (m, 2H, NHCH$_2$CH$_2$NH-napht), 5.22 (s, 2H, OCH$_2$Ph), 6.04 (bt, 1H, NH), 6.69 (d, 1H, CH aromatic rings), 6.78 (s, 1H, CH quinazoline ring), 7.18 (s, 1H, CH quinazoline ring), 7.26-7.29 (m, 2H, NH and CH aromatic rings), 7.30-7.36 (m, 4H, CH aromatic rings), 7.38-7.44 (m, 4H, CH aromatic rings), 7.78-7.80 (m, 1H, CH aromatic rings), 7.89-7.91 (m, 1H, CH aromatic rings).

General Procedure for the Preparation of the Intermediates 17 and 18

7-(benzyloxy)-N-(1-benzylpyperidin-4-yl)-6-methoxy-2-(4-phenylpiperazin-1-yl)quinazolin-4-amine (17)

To the intermediate 15 (0.818 mmol, 400 mg, 1 eq.) was added N-phenylpiperazine (6.543 mmol, 1.061 g, 0.99 mL, 8 eq.) and isoamyl alcohol (3.5 mL). The reaction was stirred in a sealed tube at 110° C. for 4 h and 45 min. The reaction mixture was then cooled at room temperature, filtered, and washed over the filter with diethyl ether and petroleum ether. The crude solid was then triturated with water, collected by filtration and purified by crystallization from AcOEt to afford 17 as a white powder (400 mg, 80%).

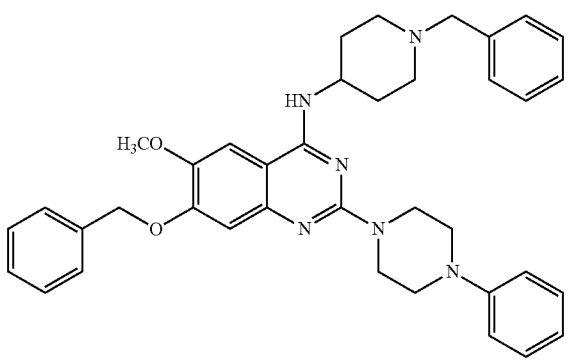 [SMILES: COc1cc2c(NC3CCN(Cc4ccccc4)CC3)nc(N3CCN(c4ccccc4)CC3)nc2cc1OCc1ccccc1]

M.p.: 199-200° C. $^1$H-NMR (400 MHz; DMSO) δ 1.63-1.68 (m, 2H, 2×CH piperidine ring), 1.97-1.99 (m, 2H, 2×CH piperidine ring), 2.06-2.12 (m, 2H, 2×CH piperidine ring), 2.89-2.91 (d, 2H, 2×CH piperidine ring), 3.18 (m, 4H, 2×CH$_2$ piperazine ring), 3.52 (s, 2H, NCH$_2$Ph), 3.83 (m, 7H, 2×CH$_2$ piperazine ring and OCH$_3$), 4.07 (bm, 1H, NHC$_4$—H-piperidine ring), 5.18 (s, 2H, OCH$_2$Ph), 6.78-6.82 (m, 1H, CH phenyl rings), 6.85 (s, 1H, CH quinazoline ring), 6.99-7.01 (m, 2H, CH phenyl rings), 7.21-7.25 (m, 3H, CH phenyl rings and NH), 7.33-7.50 (m, 11H, CH phenyl and quinazoline rings).

N[1]-(7-(benzyloxy)-6-methoxy-2-(4-phenylpiperazin-1-yl)quinazolin-4-yl)-N[2]-(naphtalen-1-yl)ethane-1,2-diamine (18)

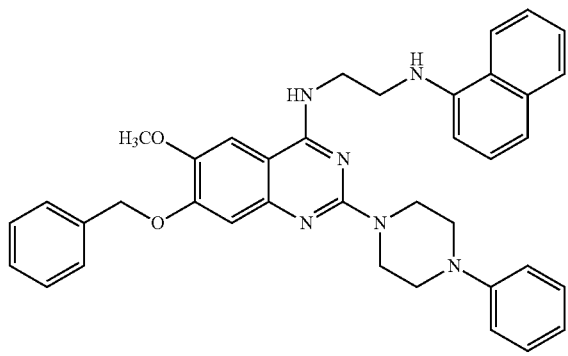 [SMILES: COc1cc2c(NCCNc3cccc4ccccc34)nc(N3CCN(c4ccccc4)CC3)nc2cc1OCc1ccccc1]

M.p.: 124° C. $^1$H-NMR (400 MHz; DMSO) δ 3.20 (m, 4H, 2×CH$_2$ piperazine ring), 3.53-3.56 (m, 2H, NHCH$_2$CH$_2$NH-napht), 3.83 (s, 3H, OCH$_3$), 3.87-3.92 (m, 6H, 2×CH$_2$ piperazine ring and NHCH$_2$CH$_2$NH-napht), 5.20 (s, 2H, OCH$_2$Ph), 6.40 (t, 1H, NH), 6.65 (d, 1H, CH aromatic rings), 6.78-6.82 (t, 1H, CH aromatic rings), 6.90 (s, 1H, CH quinazoline ring), 6.98 (d, 2H, CH aromatic rings), 7.12 (d, 1H, CH aromatic rings), 7.23 (t, 2H, CH aromatic rings), 7.29-7.48 (m, 9H, CH aromatic rings), 7.76 (d, 1H, CH aromatic rings), 8.00-8.04 (m, 2H, CH aromatic rings and NH).

General Procedure for the Preparation of the Intermediates 19 and 20

4-((1-benzylpiperidin-4-yl)amino)-6-methoxy-7-hydroxy-2-(4-phenylpiperazin-1-yl)quinazoline (19)

Trifluoroacetic acid (50.75 mmol, 5.78 g, 3.90 mL, 78 eq.) was added at 0° C. to 17 (0.65 mmol, 400 mg, 1 eq.). The resulting solution was stirred at 115° C. for 30 min, then TFA was removed under vacuum providing a crude that was suspended in H$_2$O at 0° C. The resulting suspension was basified with saturated solutions of Na$_2$CO$_3$ and NaHCO$_3$ until pH 9-10, and then the suspension was filtrated to give a crude product that was purified by a silica gel column eluting with a mixture AcOEt/MeOH/NH$_3$ (95:5:0.5) to get 19 as a white powder (quantitative yield).

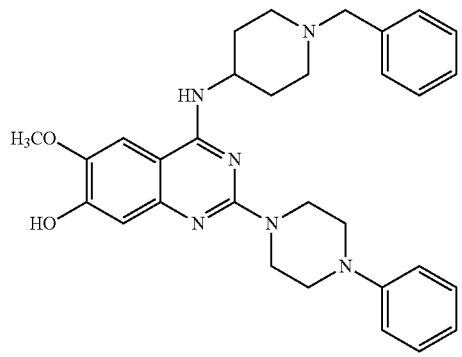 [SMILES: COc1cc2c(NC3CCN(Cc4ccccc4)CC3)nc(N3CCN(c4ccccc4)CC3)nc2cc1O]

M.p.: 131° C. $^1$H-NMR (400 MHz; DMSO) δ 1.59-1.66 (m, 2H, 2×CH piperidine ring), 1.96-1.99 (m, 2H, 2×CH piperidine ring), 2.06-2.12 (m, 2H, 2×CH piperidine ring), 2.88-2.91 (m, 2H, 2×CH piperidine ring), 3.18 (m, 4H, 2×CH$_2$ piperazine ring), 3.52 (s, 2H, NCH$_2$Ph), 3.83-3.86 (m, 7H, 2×CH$_2$ piperazine ring and OCH$_3$), 4.06-4.09 (bm, 1H, NHC$_4$—H-piperidine ring), 6.65 (s, 1H, CH quinazoline ring), 6.80 (m, 1H, CH phenyl rings), 6.99-7.01 (m, 2H, CH phenyl rings), 7.23-7.45 (m, 9H, CH phenyl rings, CH quinazoline ring and NH), 9.70 (bs, 1H, OH).

6-Methoxy-4-((2-(naphtalen-1-ylamino)ethyl)amino)-2-(4-phenylpiperazin-1-yl)quinazolin-7-ol (20)

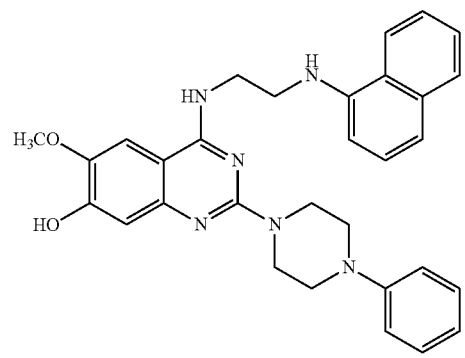 [SMILES: COc1cc2c(NCCNc3cccc4ccccc34)nc(N3CCN(c4ccccc4)CC3)nc2cc1O]

M.p.: 147-150° C. $^1$H-NMR (400 MHz; DMSO) δ 3.16-3.26 (m, 4H, 2×CH$_2$ piperazine ring), 3.52-3.55 (m, 2H, NHCH$_2$CH$_2$NH-napht), 3.87 (s, 3H, OCH$_3$), 3.89-3.90 (m, 6H, 2×CH$_2$ piperazine ring and NHCH$_2$CH$_2$NH-napht), 6.39-6.41 (t, 1H, NH), 6.64-6.66 (d, 1H, CH aromatic rings), 6.68-6.70 (s, 1H, CH aromatic rings), 6.78-6.82 (t, 1H, CH aromatic rings), 6.98-7.00 (d, 2H, CH aromatic rings), 7.11-7.13 (d, 1H, CH aromatic rings), 7.22-7.26 (m, 2H, CH aromatic rings), 7.29-7.31 (m, 1H, CH aromatic rings), 7.33-7.43 (m, 3H, CH aromatic rings), 7.75-7.77 (m, 1H, CH aromatic rings), 7.93 (bm, 1H, NH), 8.02-8.04 (m, 1H, CH aromatic rings), 9.76-9.79 (bs, 1H, OH).

General Procedure for the Preparation of the Intermediates 21 and 22

4-((1-Benzylpiperidine-4-yl)amino)-6-methoxy-2-(4-phenylpiperazin-1-yl)-7-(O—((N-Boc)piperidin-4-ylmethoxy))quinazoline (21)

To a solution of 20 (0.414 mmol, 217.6 mg, 1 eq.), N-Boc-4-(hydroxymethyl)piperidine (2.486 mmol, 535.4 mg, 6 eq.) and PPh$_3$ (3.42 mmol, 896.9 mg, 8.25 eq.) in dry THF (8.0 mL) was added DIAD (3.10 mmol, 628.6 mg, 0.611 mL, 7.5 eq.) cooling at 0° C. under a nitrogen atmosphere. The resulting reaction mixture was then stirred at RT for 28 h. After the completion of the reaction, the solvent was evaporated under vacuum and the crude product was purified by a silica gel flash chromatography (SNAP 100, Biotage Isolera One™) using a linear gradient of MeOH (0% to 40%) in AcOEt to give 21 as a white powder (283.4 mg, 95%).

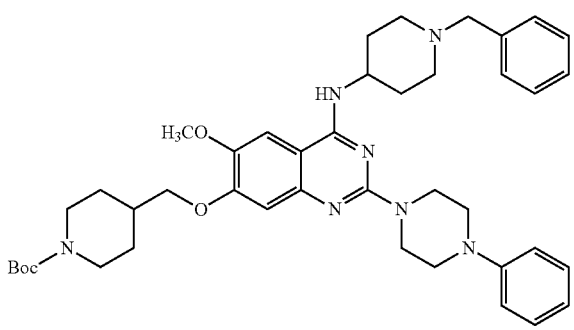 [SMILES: COc1cc2c(NC3CCN(Cc4ccccc4)CC3)nc(N3CCN(c4ccccc4)CC3)nc2cc1OCC1CCN(C(=O)OC(C)(C)C)CC1]

M.p.: 225-226° C. $^1$H-NMR (400 MHz; DMSO) δ 1.13-1.23 (m, 2H, 2×CH piperidine ring), 1.40 (s, 9H, 3×CH$_3$ t-Bu), 1.63-1.65 (m, 2H, 2×CH piperidine ring), 1.74-1.77 (m, 2H, 2×CH piperidine ring), 1.96-1.99 (m, 3H, 2×CH piperidine ring and OCH$_2$CH), 2.06-2.12 (m, 2H, 2×CH piperidine ring), 2.77 (bm, 2H, 2×CH piperidine ring), 2.88-2.91 (d, 2H, 2×CH piperidine ring), 3.18 (m, 4H, 2×CH$_2$ piperazine ring), 3.51 (s, 2H, NCH$_2$Ph), 3.82-3.84 (m, 7H, 2×CH$_2$ piperazine and OCH$_3$), 3.90 (m, 2H, OCH$_2$) 3.96-3.99 (m, 3H, NHC$_4$—H-piperidine ring and 2×CH piperidine ring), 6.75 (s, 1H, CH quinazoline ring), 6.80 (m, 1H, CH phenyl ring), 7.00 (d, 2H, CH phenyl rings), 7.21-7.25 (m, 3H, CH phenyl rings and NH), 7.33-7.37 (m, 5H, CH phenyl rings), 7.47 (s, 1H, CH quinazoline ring).

4-(((2-Naphtalen-1-ylamino)ethyl)amino)-6-methoxy-2-(4-phenylpiperazin-1-yl)-7-(O—((N-Boc)piperidin-4-ylmethoxy))quinazoline (22)

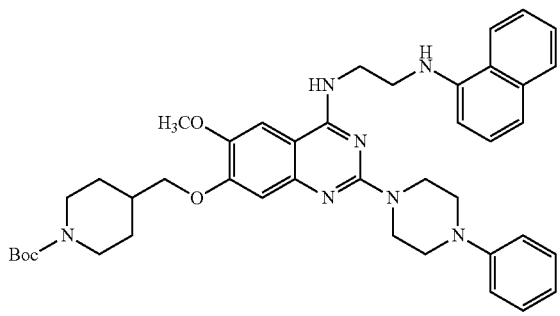 [SMILES: COc1cc2c(NCCNc3cccc4ccccc34)nc(N3CCN(c4ccccc4)CC3)nc2cc1OCC1CCN(C(=O)OC(C)(C)C)CC1]

M.p.: 174° C. $^1$H-NMR (400 MHz; DMSO) δ 1.14-1.24 (m, 2H, 2×CH piperidine ring), 1.41 (s, 9H, 3×CH$_3$ t-Bu), 1.75-1.78 (m, 2H, 2×CH piperidine ring), 1.96-2.05 (m, 1H, OCH$_2$CH), 2.76 (bm, 2H, 2×CH piperidine ring), 3.20-3.21 (m, 4H, 2×CH$_2$ piperazine ring), 3.51-3.56 (m, 2H, NHCH$_2$CH$_2$NH-napht), 3.82 (s, 3H, OCH$_3$), 3.86-4.00 (m, 10H, NHCH$_2$CH$_2$NH-napht, 2×CH$_2$ piperazine ring, OCH$_2$ and 2×CH piperidine ring), 6.38-6.41 (m, 1H, NH), 6.65 (d, 1H, aromatic rings), 6.79-6.82 (m, 2H, CH aromatic rings), 6.98-7.00 (d, 2H, CH aromatic rings), 7.11-7.13 (d, 1H, CH aromatic rings), 7.21-7.29 (m, 2H, CH aromatic rings), 7.31-7.37 (m, 1H, CH aromatic rings), 7.39-7.45 (m, 3H, CH aromatic rings), 7.76 (d, 1H, CH aromatic rings), 7.96-7.98 (t, 1H, NH), 8.02-8.06 (d, 1H, CH aromatic rings).

General Procedure for the Preparation of the Intermediates 23 and 24

N$^1$-(6-methoxy-2-(4-phenylpiperazin-1-yl)-7-(piperidin-4-ylmethoxy)quinazolin-4-yl)-N$^2$-(naphtalen-1-yl)ethane-1,2-diamine dihydrochloride (24)

A solution of HCl 4N in dioxane (5.85 mmol, 1.46 mL, 55 eq.) was added dropwise at 0° C. to a solution of 22 (0.106 mmol, 76.5 mg, 1 eq.) in a mixture of dry MeOH (4 mL) and dry THF (4 mL). The resulting reaction mixture was then stirred at RT for 49 h and half. After the completion of the reaction, the resulting suspension was filtrated and washed with dry THF and dry Et$_2$O to get 23 as a white hygroscopic salt (quantitative yield).

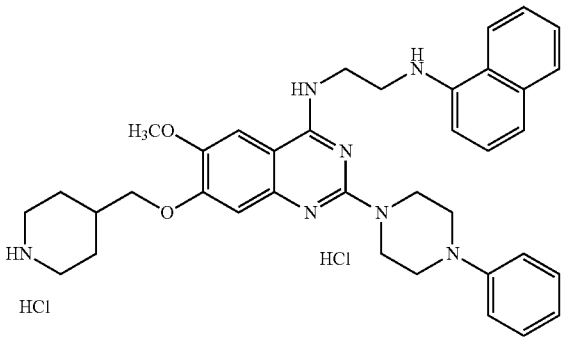 [SMILES: COc1cc2c(NCCNc3cccc4ccccc34)nc(N3CCN(c4ccccc4)CC3)nc2cc1OCC1CCNCC1 ; Cl ; Cl]

M.p.: 215° C. $^1$H-NMR (400 MHz; DMSO) δ 1.51-1.54 (m, 2H, 2×CH piperidine ring), 1.94-1.97 (m, 2H, 2×CH piperidine ring), 2.18-2.19 (m, 1H, OCH$_2$CH), 2.92-2.97 (m, 2H, 2×CH piperidine ring), 3.25 (m, 4H, 2×CH$_2$ piperazine ring), 3.31-3.34 (m, 2H, 2×CH piperidine ring), 3.61-3.64 (m, 2H, NHCH$_2$CH$_2$NH-napht), 3.90 (s, 3H, OCH$_3$), 3.97 (m, 8H, NHCH$_2$CH$_2$NH-napht, 2×CH$_2$ piperazine ring and OCH$_2$), 6.68 (d, 1H, CH aromatic rings), 6.84-6.87 (m, 1H, CH aromatic rings), 7.00-7.03 (m, 2H, CH aromatic rings), 7.14-7.16 (m, 1H, CH aromatic rings), 7.25-7.45 (m, 5H, CH aromatic rings and piperidine NH.HCl), 7.53 (s, 1H, CH quinazoline ring), 7.76 (d, 1H, CH aromatic rings), 7.94 (s, 1H, CH quinazoline ring), 8.17-8.18 (d, 1H, CH aromatic rings), 8.56 (bm, 2H, CH aromatic rings and NH), 8.87 (m, 1H, CH aromatic rings), 9.73 (s, 1H, NH), 12.18 (s, 1H, HCl).

N-(1-benzylpiperidin-4-yl)-6-methoxy-2-(4-phenylpiperazin-1-yl)-7-(piperidin-4-ylmethoxy)quinazolin-4-amine trihydrochloride (23)

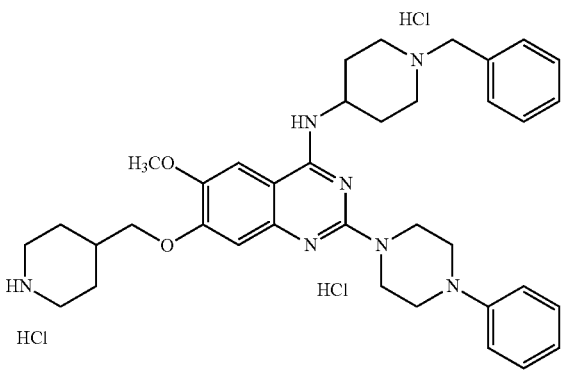 [SMILES: Cl ; Cl ; COc1cc2c(NC3CCN(Cc4ccccc4)CC3)nc(N3CCN(c4ccccc4)CC3)nc2cc1OCC1CCNCC1 ; Cl]

M.p.: 247-250° C. $^1$H-NMR (400 MHz; DMSO) δ 1.51-1.54 (m, 2H, 2×CH piperidine ring), 1.94-1.97 (m, 2H, 2×CH piperidine ring), 2.15-2.26 (m, 5H, 4×CH piperidine ring and OCH$_2$CH), 2.91-2.93 (m, 2H, 2×CH piperidine ring), 3.16-3.19 (m, 2H, 2×CH piperidine ring), 3.34-3.43 (m, 8H, 2×CH$_2$ piperazine ring and 4×CH piperidine ring), 3.90 (s, 3H, OCH$_3$), 3.98-4.0 (m, 2H, OCH$_2$), 4.07 (m, 4H, 2×CH$_2$ piperazine ring), 4.29-4.31 (d, 2H, NCH$_2$Ph), 4.40 (bs, 1H, NHC$_4$—H-piperidine ring), 6.85-6.89 (m, 1H, CH aromatic rings), 7.05 (d, 2H, CH aromatic rings), 7.26-7.30

(m, 2H, CH aromatic rings), 7.48-7.49 (m, 3H, CH aromatic rings and piperidine NH.HCl), 7.68-7.69 (m, 3H, CH aromatic rings), 8.03 (s, 1H, CH quinazoline ring), 8.64-8.67 (bm, 1H, CH aromatic rings), 8.96-9.00 (m, 1H, CH aromatic rings), 9.33-9.35 (d, 1H, NH), 11.25 (bs, 1H, PhCH₂N.HCl), 12.52 (s, 1H, HCl).

General Procedure for the Preparation of Compounds E and F

N-(1-benzylpiperidin-4-yl)-6-methoxy-2-(4-phenylpiperazin-1-yl)-7-((1-(2-(quinolin-4-ylamino)ethyl)piperidin-4-yl)methoxy)quinazolin-4-amine (E)

23 (0.123 mmol, 90 mg) was stirred for 20 min in 20 mL of Na₂CO₃ saturated solution, then extracted with CHCl₃/iPrOH (4:1) (6×20 mL) and dried over anhydrous Na₂SO₄. After filtration, the solvent was evaporated under reduced pressure to obtain the free amine. NaI (0.110 mmol, 19.27 mg, 1.25 eq.), K₂CO₃ (0.122 mmol, 19.91 mg, 1.4 eq.) and N-(2-bromoethyl)quinoline-4-amine (0.110 mmol, 32.29 mg, 1.25 eq.) were then added in sequence to the free amine of compound 23 (0.102 mmol, 64 mg, 1 eq.) and the resulting mixture was stirred in dry DMF (2 mL) at 65° C. for 29 h. After the completion of the reaction, the medium was quenched with NaCl saturated solution (10 mL) and the product was extracted with AcOEt (7×10 mL). The organic phase was then dried over anhydrous Na₂SO₄, filtered and evaporated under reduced pressure to give a crude that was purified by a silica gel column eluting with a mixture AcOEt:MeOH:NH₃ (95:5:0.5) to obtain E as a white powder (50 mg, 62.5%).

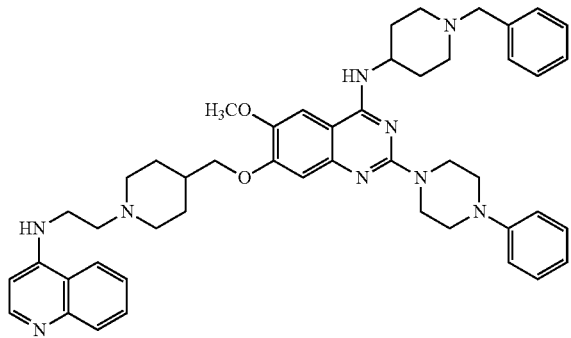 [SMILES: COc1cc2c(NC3CCN(Cc4ccccc4)CC3)nc(N3CCN(c4ccccc4)CC3)nc2cc1OCC1CCN(CCNc2ccnc3ccccc23)CC1]

M.p.: 124-126° C. ¹H-NMR (400 MHz; DMSO) δ 1.35-1.43 (m, 2H, 2×CH piperidine ring), 1.59-1.70 (m, 2H, 2×CH piperidine ring), 1.76-1.78 (m, 3H, 2×CH piperidine ring and OCH₂CH), 1.97-1.99 (m, 2H, 2×CH piperidine ring), 2.07-2.10 (m, 4H, 4×CH piperidine ring), 2.64-2.66 (m, 2H, CH₂CH₂NH-quinoline), 2.89-2.92 (m, 2H, 2×CH piperidine ring), 3.00-3.08 (m, 2H, 2×CH piperidine ring), 3.19 (m, 4H, 2×CH₂ piperazine ring), 3.42 (m, 2H, CH₂CH₂NH-quinoline), 3.52 (s, 2H, NCH₂Ph), 3.83-3.85 (m, 7H, OCH₃ and 2×CH₂ piperazine ring), 3.90-3.92 (m, 2H, CH₂O), 4.05 (bm, 1H, NHC₄—H-piperidine ring), 6.49-6.51 (d, 1H, CH quinoline ring), 6.75 (s, 1H, CH quinazoline ring), 6.78-6.80 (t, 1H, CH phenyl rings), 7.00 (d, 2H, CH phenyl rings), 7.07 (bs, 1H, NH quinoline), 7.21-7.25 (m, 3H, CH phenyl rings and NH), 7.33-7.36 (m, 5H, CH phenyl rings), 7.43-7.45 (m, 1H, CH quinoline ring), 7.47 (s, 1H, quinazoline ring), 7.62 (t, 1H, CH quinoline ring), 7.80 (d, 1H, CH quinoline ring), 8.17 (d, 1H, CH quinoline ring), 8.40 (d, 1H, CH quinoline ring).

N¹-(6-methoxy-2-(4-phenylpiperazin-1-yl)-7-((1-(2-(quinolin-4-ylamino)ethyl)piperidin-4-yl)methoxy)quinazolin-4-yl)-N²-(naphtalen-1-yl)ethane-1,2-diamine (F)

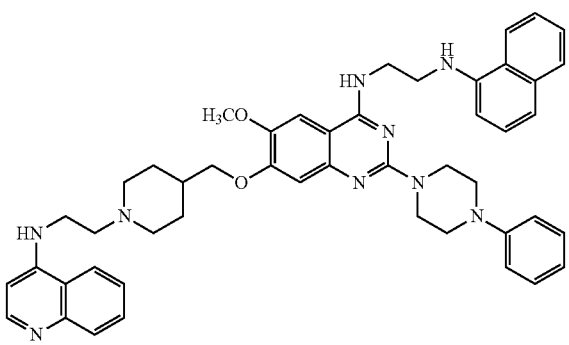 [SMILES: COc1cc2c(NCCNc3cccc4ccccc34)nc(N3CCN(c4ccccc4)CC3)nc2cc1OCC1CCN(CCNc2ccnc3ccccc23)CC1]

M.p.: 180-181° C. ¹H-NMR (400 MHz; DMSO) δ 1.36-1.39 (m, 2H, 2×CH piperidine ring), 1.78-1.80 (m, 3H, 2×CH piperidine ring and OCH₂CH), 2.04-2.09 (m, 2H, 2×CH piperidine ring), 2.63-2.65 (m, 2H, CH₂CH₂NH-quinoline), 2.99-3.01 (m, 2H, 2×CH piperidine ring), 3.20 (m, 4H, 2×CH₂ piperazine ring), 3.40 (m, 2H, CH₂CH₂NH-quinoline), 3.53-3.54 (m, 2H, NHCH₂CH₂-napht), 3.82 (s, 3H, OCH₃), 3.88-3.93 (m, 8H, CH₂O, 2×CH₂ piperazine ring and NHCH₂CH₂-napht), 6.40 (m, 1H, NH), 6.47-6.49 (d, 1H, CH quinoline ring), 6.65 (m, 1H, CH aromatic rings), 6.79-6.82 (m, 2H, CH aromatic rings), 6.98-7.04 (m, 3H, aromatic rings and NH quinoline), 7.11-7.13 (d, 1H, CH aromatic rings), 7.22-7.45 (m, 7H, CH aromatic and quinoline ring), 7.59-7.63 (t, 1H, CH quinoline ring), 7.75-7.79 (t, 2H, CH aromatic and quinoline rings), 7.98-8.04 (m, 2H, CH aromatic rings and NH), 8.16 (d, 1H, CH quinoline ring), 8.39 (d, 1H, CH quinoline ring).

Example 4: Compound G

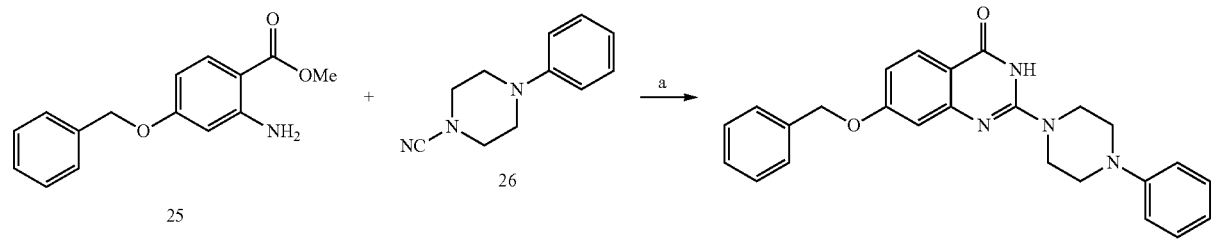

61 62

-continued

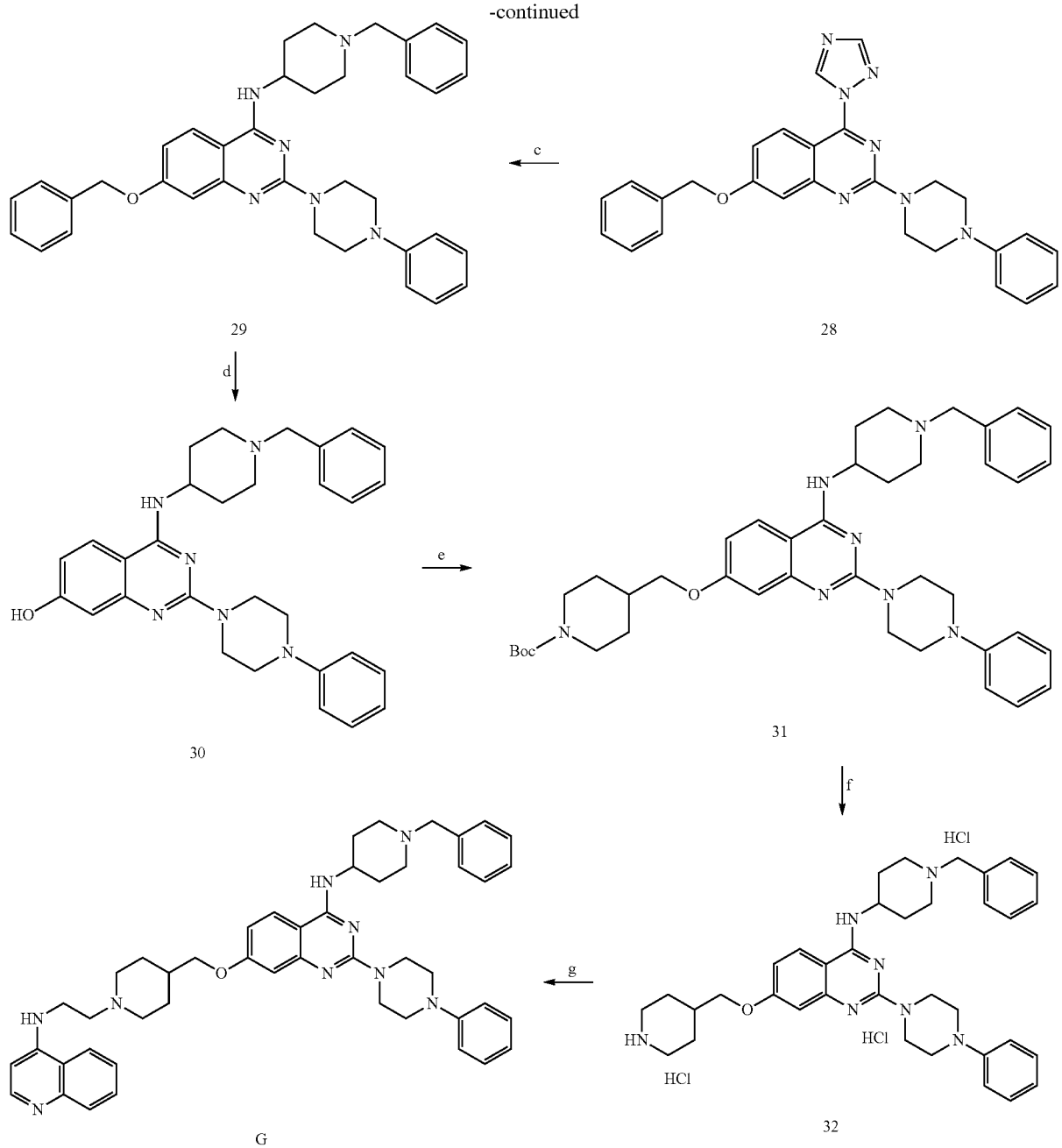

a) NaH, xylene, N₂, 140° C., 3 h 30 min, 65%. b) 1. POCl₃, TEA, 1,2,4-triazole, dry CH₃CN, 0° C. for 40 min then RT for 30 min. 2. Addition of a solution of 27 in dry CHCl₃, N₂, RT overnight then 100° C., 5 h, 70%. c) 1-benzylpiperidin-4-amine, sealed tube, 125° C., 4 h, 74%. d) TFA, 0° C. to 115° C., 30 min, quantitative yield. e) N-Boc-4-(hydroxymethyl)piperidine, DIAD, PPh₃, dry THF, 0° C. to RT, N₂, 26 h, 69%. f) HCl 4N in dioxane, dry MeOH, dry THF, 0° C. to RT, 76 h, quantitative yield. g) 35, NaI, K₂CO₃, dry DMF, 65° C., 51 h, 75%.

Preparation of Some Reagents:

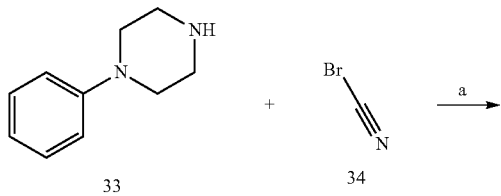

-continued

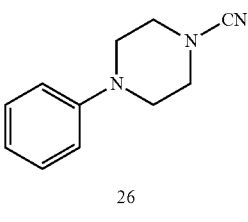

a) DIPEA, dry DCM, 0° C. to RT, 1 h, 96%.

Preparation of 4-phenylpiperazine-1-carbonitrile (26)

A 3M solution of BrCN in DCM (15.37 mmol, 5.125 mL, 1.25 eq.) was added dropwise at 0° C. to a solution of DIPEA (36.9 mmol, 6.43 mL, 3 eq.) and N-phenylpiperazine (33) (12.3 mmol, 2 g, 1.88 mL, 1 eq.) in dry DCM (22 mL). The resulting reaction mixture was then stirred at room temperature for 1 h. After the completion of the reaction, the medium was quenched with $H_2O$ (30 mL) and the aqueous phase extracted with DCM (4×20 mL). The organic phases were then combined, washed with brine (7 mL) and dried over anhydrous $Na_2SO_4$. After filtration, the solvent was evaporated under vacuum to give the desired product 26 as a white solid (96%), that was used in the subsequent step without further purification.

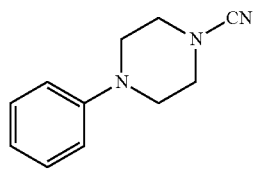 [SMILES: N#CN1CCN(c2ccccc2)CC1]

M.p.: 52-53° C. $^1$H-NMR (400 MHz; $CDCl_3$) δ 3.23 (t, 4H, 2×$CH_2$ piperazine ring), 3.39 (t, 4H, 2×$CH_2$ piperazine ring), 6.90-6.97 (m, 3H, CH phenyl ring), 7.26-7.33 (m, 2H, CH phenyl ring).

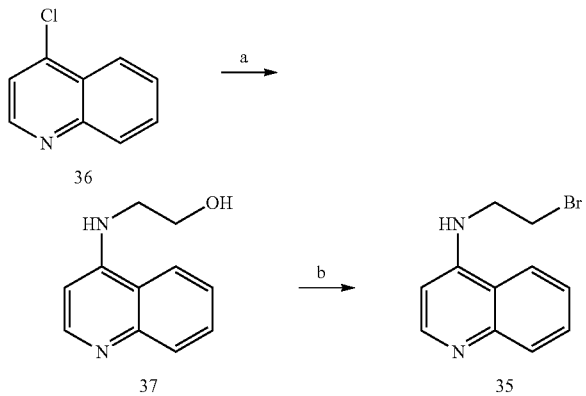

a) Ethanolamine, MW, 140° C., 22 min, 95%. b) HBr 48%, conc. $H_2SO_4$, 0° C. to 165° C., 7 h, 60%.

Preparation of 2-(quinolin-4-ylamino)ethanol (37)

A mixture of 4-chloroquinoline (36) (2.44 mmol, 400 mg, 1 eq.) and ethanolamine (9.78 mmol, 597.3 mg, 0.588 mL, 4 eq.) was placed in a 2.5 mL microwave reaction vessel equipped with a magnetic stirrer. The reaction vessel was then placed in the cavity of the microwave reactor. The temperature was raised to 140° C. and the vessel was irradiated for 22 min at the same temperature (the reaction temperature was modulated through the power switch and measured through the internal infrared sensor of the microwave apparatus). After the completion of the reaction, the mixture was cooled at room temperature and transferred with methanol in a flask of 50 mL. After the evaporation of the solvent under vacuum, a saturated solution of $Na_2CO_3$ was added and the aqueous phase was extracted with AcOEt (5×20 mL) and with $CHCl_3$/iPrOH (4:1) (2×20 mL). The crude product was then triturated with a mixture AcOEt/diethyl ether (1:1) and the desired pure product 37 was finally collected by filtration as a white powder (437.2 mg, 95%).

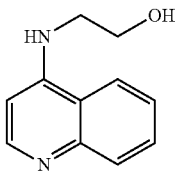 [SMILES: OCCNc1ccnc2ccccc12]

M.p.: 148-151° C. $^1$H-NMR (400 MHz; DMSO) δ 3.35-3.37 (m, 2H, $NHCH_2CH_2OH$), 3.67 (m, 2H, $NHCH_2CH_2OH$), 4.86 (bs, 1H, OH), 6.48 (m, 1H, CH quinoline ring), 7.09 (m, 1H, NH), 7.41 (m, 1H, CH quinoline ring), 7.60 (m, 1H, CH quinoline ring), 7.77 (d, 1H, CH quinoline ring), 8.20 (d, 1H, CH quinoline ring), 8.38 (m, 1H, CH quinoline ring).

Preparation of N-(2-bromoethyl)quinolin-4-amine (35)

HBr 48% (27 mmol, 2.182 g, 1.467 mL, 27 eq.) and concentrated $H_2SO_4$ (9.9 mmol, 945.3 mg, 0.513 mL, 9.9 eq.) were added in sequence at 0° C. to the previously obtained 2-(quinolin-4-ylamino)ethanol (37) (1 mmol, 188.2 mg, 1 eq.). The reaction mixture was then stirred for 7 h at 165° C., then it was cooled down at room temperature and transferred with methanol in a flask of 50 mL. After the evaporation of the solvent under vacuum, ice (2.5 mL) and $Na_2CO_3$ saturated solution (2.5 mL) were added to the residue, that was cooled at 0° C. and made basic (up to pH 10) with NaOH 2N. The aqueous layer was then extracted with AcOEt (8×20 mL), and the organic phase dried over anhydrous $Na_2SO_4$ and concentrated under reduced pressure. The crude product was finally purified by a silica gel flash chromatography (SNAP 50, Biotage Isolera Spektra One™) using a linear gradient of MeOH (1 to 10%) in $CHCl_3$ to give 35 as a white powder (150 mg, 60%).

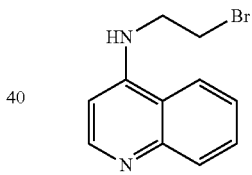

M.p.: 138-140° C. $^1$H-NMR (400 MHz; DMSO) δ 3.73-3.77 (m, 4H, $NHCH_2CH_2Br$), 6.57-6.58 (d, 1H, CH quinoline ring), 7.47-7.49 (t, 1H, CH quinoline ring), 7.52 (m 1H, NH), 7.63-7.67 (t, 1H, CH quinoline ring), 7.80-7.82 (d, 1H, CH quinoline ring), 8.19-8.21 (d, 1H, CH quinoline ring), 8.42-8.43 (d, 1H, CH quinoline ring).

7-(benzyloxy)-2-(4-phenylpiperazin-1-yl)quinazolin-4-ol (27)

26 (2.67 mmol, 500 mg, 1 eq.) and dry sodium hydride (9.346 mmol, 224.3 mg, 3.5 eq.) were added in sequence under nitrogen atmosphere to a solution of methyl 7-benzyloxy-2-aminobenzoate 25 (4.005 mmol, 1.03 g, 1.5 eq.) in xylenes (mixture of isomers) (17 mL). The resulting mixture was then heated at 140° C. for 3 h and 30 min. After the completion of the reaction, the medium was quenched with water (23 mL) and the product was extracted with AcOEt (5×23 mL) and with $CHCl_3$/iPrOH (4:1) (5×23 mL). The organic phases were combined and dried over $Na_2SO_4$. After filtration, the solvent was removed under vacuum and the product was purified by a silica gel column eluting with a mixture $CHCl_3$:MeOH (99.5:0.5) to afford 27 as a white powder (715 mg, 65%).

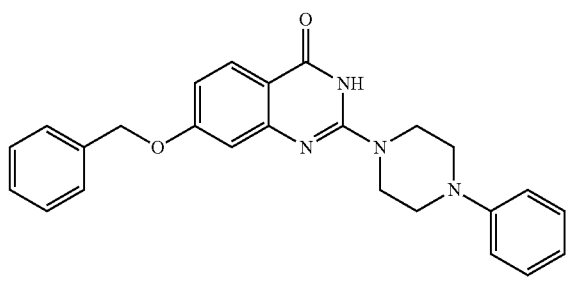 [SMILES: O=c1[nH]c(N2CCN(c3ccccc3)CC2)nc2cc(OCc3ccccc3)ccc12]

M.p.: >250° C. $^1$H-NMR (400 MHz; DMSO) δ 3.20-3.23 (m, 4H, 2×CH$_2$ piperazine ring), 3.76-3.78 (m, 4H, 2×CH$_2$ piperazine ring), 5.21 (s, 2H, OCH$_2$Ph), 6.79-6.83 (m, 3H, CH aromatic rings), 6.98-7.00 (d, 2H, CH aromatic rings), 7.22-7.26 (t, 2H, CH aromatic rings), 7.34-7.37 (m, 1H, CH aromatic rings), 7.39-7.43 (t, 2H, CH aromatic rings), 7.46-7.48 (d, 2H, CH aromatic rings), 7.82 (d, 1H, CH aromatic rings), 11.05-11.36 (bs, 1H, NH).

7-benzyloxy-2-(4-phenylpiperazin-1-yl)-4-(1H-1,2,4-triazol-1-yl)quinazoline (28)

To a solution of triazole (2.959 mmol, 198.5 mg, 6.7 eq.) in dry acetonitrile (5.5 mL) at 0° C. under nitrogen atmosphere, were added phosphorous oxychloride (0.972 mmol, 149 mg, 0.091 mL, 2.2 eq.) in one portion and triethylamine (2.959 mmol, 299 mg, 0.412 mL, 6.7 eq.) dropwise. The mixture was vigourously stirred at 0° C. for 40 min. and then at room temperature for 30 min. A solution of 27 (0.442 mmol, 182.2 mg, 1 eq.) in dry CHCl$_3$ (5.5 mL) was then added and the resulting mixture was stirred at room temperature overnight. To get the complete disappearance of the starting material, the temperature of the reaction was raised up to 100° C. and furtherly stirred for 5 h. After completion of the reaction, the medium was quenched with water (12 mL) and the product was extracted with AcOEt (5×12 mL) and with CHCl$_3$/iPrOH (4:1) (5×12 mL). The organic phases were combined and dried over Na$_2$SO$_4$. After filtration, the solvent was removed under vacuum and the product was purified by a silica gel column eluting with a mixture CHCl$_3$:hexane (85:15) to obtain the desired product 28 as a yellow powder (143 mg, 70%).

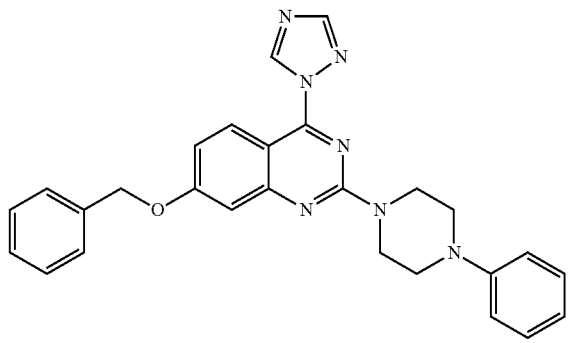 [SMILES: c1ccc(COc2ccc3c(-n4cncn4)nc(N4CCN(c5ccccc5)CC4)nc3c2)cc1]

M.p.: 196-197° C. $^1$H-NMR (400 MHz; CDCl$_3$) δ 3.33-3.35 (m, 4H, 2×CH$_2$ piperazine ring), 4.13-4.16 (m, 4H, 2×CH$_2$ piperazine ring), 5.23 (s, 2H, OCH$_2$Ph), 6.94 (t, 1H, CH aromatic rings), 7.01-7.04 (m, 3H, CH aromatic rings), 7.09 (d, 1H, CH aromatic rings), 7.31-7.51 (m, 7H, CH aromatic rings), 8.25 (s, 1H, CH triazole ring), 8.88 (d, 1H, CH aromatic rings), 9.27 (s, 1H, CH triazole ring).

7-benzyloxy-N-(1-benzylpiperidin-1-yl)-2-(4-phenylpiperazin-1-yl)quinazolin-4-amine (29)

A mixture of 28 (0.235 mmol, 109 mg, 1 eq.) and N-benzylpiperidine-4-amine (3.53 mmol, 671 mg, 0.72 mL, 15 eq.) was stirred in sealed tube at 125° C. for 4 h. The reaction was diluted with AcOEt and the organic phase was washed with NaCl saturated solution (12×3 mL) to remove the amine in excess. The organic phase was then dried over Na$_2$SO$_4$. After filtration, the solvent was removed under vacuum and the crude product was purified on a silica gel column eluting with a mixture AcOEt/hexane/MeOH/NH$_3$ (20:80:1:0.1) to afford 29 as a white powder (101.5 mg, 74%).

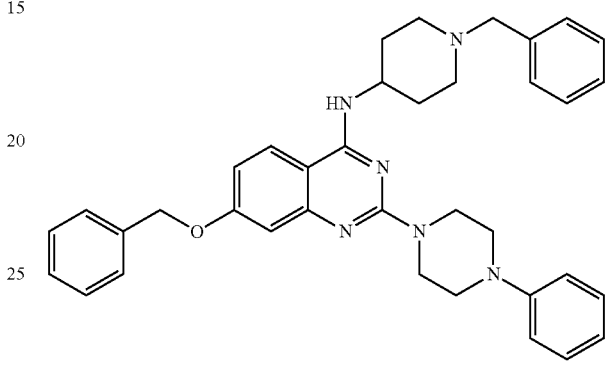

M.p.: 104-105° C. $^1$H-NMR (400 MHz; DMSO) δ 1.59-1.67 (m, 2H, 2×CH piperidine ring), 1.93-1.96 (m, 2H, 2×CH piperidine ring), 2.06-2.11 (m, 2H, 2×CH piperidine ring), 2.86-2.89 (m, 2H, 2×CH piperidine ring), 3.19 (m, 4H, 2×CH$_2$ piperazine ring), 3.50 (s, 2H, NCH$_2$Ph), 3.89 (m, 4H, 2×CH$_2$ piperazine ring), 4.02-4.07 (bm, 1H, NHC$_4$—H-piperidine ring), 5.19 (s, 2H, OCH$_2$Ph), 6.75-6.82 (m, 3H, CH aromatic rings), 6.99-7.01 (d, 2H, CH aromatic rings), 7.21-7.27 (m, 3H, CH aromatic rings and NH), 7.33-7.36 (m, 5H, CH aromatic rings), 7.39-7.43 (t, 2H, CH aromatic rings), 7.46-7.48 (m, 3H, CH aromatic rings), 8.00 (d, 1H, CH aromatic rings).

4-((1-Benzylpiperidin-4-yl)amino)-2-(4-phenylpiperazin-1-yl)quinazolin-7-ol (30)

Prepared according to the general procedure for preparing intermediates 19 and 20.

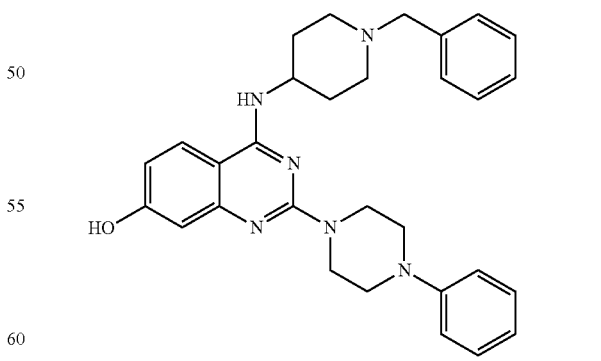

M.p.: 158-160° C. $^1$H-NMR (400 MHz; DMSO) δ 1.58-1.66 (m, 2H, 2×CH piperidine ring), 1.92-1.95 (m, 2H, 2×CH piperidine ring), 2.05-2.11 (m, 2H, 2×CH piperidine ring), 2.86-2.88 (m, 2H, 2×CH piperidine ring), 3.18 (m, 4H, 2×CH$_2$ piperazine ring), 3.50 (s, 2H, NCH$_2$Ph), 3.87 (m, 4H, 2×CH$_2$ piperazine ring), 4.03-4.08 (bm, 1H, NHC$_4$—H- piperidine ring), 6.55-6.57 (m, 2H, CH aromatic rings), 6.78-6.82 (t, 1H, CH aromatic rings), 6.99-7.01 (m, 2H, CH aromatic rings), 7.21-7.36 (m, 8H, CH aromatic rings and NH), 7.90 (d, 1H, CH quinazoline ring), 9.85 (s, 1H, OH).

4-((1-benzylpiperidine-4-yl)amino)-2-(4-phenylpiperazin-1-yl)-7-(O—((N-Boc)piperidin-4-ylmethoxy)) quinazoline (31)

Prepared according to the general procedure for preparing intermediates 21 and 22.

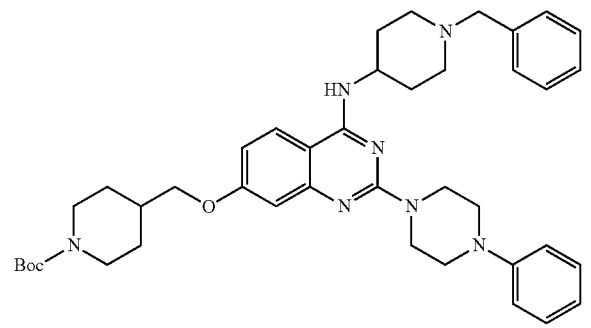 [SMILES: CC(C)(C)OC(=O)N1CCC(COc2ccc3c(NC4CCN(Cc5ccccc5)CC4)nc(N4CCN(c5ccccc5)CC4)nc3c2)CC1]

M.p.: 186-187° C. $^1$H-NMR (400 MHz; DMSO) δ 1.13-1.24 (m, 2H, 2×CH piperidine ring), 1.40 (s, 9H, 3×CH$_3$ t-Bu), 1.61-1.66 (m, 2H, 2×CH piperidine ring), 1.75-1.77 (m, 2H, 2×CH piperidine ring), 1.93-1.99 (m, 3H, 2×CH piperidine ring and OCH$_2$CH), 2.05-2.11 (m, 2H, 2×CH piperidine ring), 2.71-2.80 (bm, 2H, 2×CH piperidine ring), 2.86-2.89 (m, 2H, 2×CH piperidine ring), 3.18-3.19 (m, 4H, 2×CH$_2$ piperazine ring), 3.50 (s, 2H, NCH$_2$Ph), 3.89-3.92 (m, 6H, 2×CH$_2$ piperazine and OCH$_2$), 3.97-4.02 (bm, 3H, NHC$_4$—H-piperidine ring and 2×CH piperidine ring), 6.66-6.70 (m, 2H, CH aromatic rings), 6.78-6.82 (t, 1H, CH aromatic rings), 7.00 (d, 2H, CH aromatic rings), 7.21-7.28 (m, 3H, CH aromatic rings and NH), 7.31-7.34 (m, 4H, CH aromatic rings), 7.45-7.46 (d, 1H, CH aromatic rings), 7.96 (d, 1H, CH quinazoline ring).

N-(1-benzylpiperidin-4-yl)-2-(4-phenylpiperazin-1-yl)-7-(piperidin-4-ylmethoxy)quinazolin-4-amine trihydrochloride (32)

Prepared according to the general procedure for preparing intermediates 23 and 24.

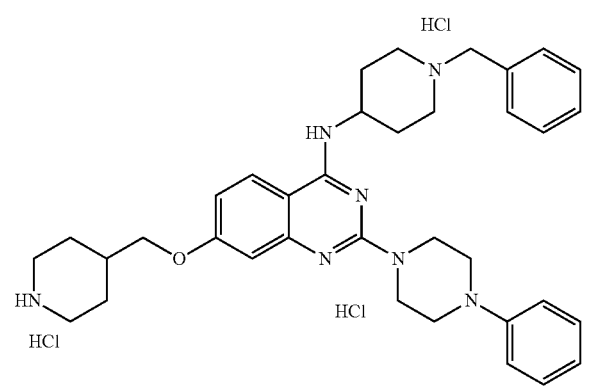 [SMILES: Cl ; c1ccc(CN2CCC(Nc3nc(N4CCN(c5ccccc5)CC4)nc4cc(OCC5CCNCC5)ccc34)CC2)cc1 ; Cl ; Cl]

M.p.: >250° C. $^1$H-NMR (400 MHz; DMSO) δ 1.45-1.62 (m, 2H, 2×CH piperidine ring), 1.91-1.98 (m, 2H, 2×CH piperidine ring), 2.19-2.22 (m, 5H, 4×CH piperidine ring and OCH$_2$CH), 2.89-2.92 (m, 2H, 2×CH piperidine ring), 3.17-3.18 (m, 2H, 2×CH piperidine ring), 3.29-3.4 (m, 8H, 2×CH$_2$ piperazine ring and 4×CH piperidine ring), 3.98-4.00 (m, 2H, OCH$_2$), 4.15 (m, 4H, 2×CH$_2$ piperazine ring), 4.28-4.30 (d, 2H, NCH$_2$Ph), 4.40-4.42 (bs, 1H, NHC$_4$—H-piperidine ring), 6.88-6.92 (m, 1H, CH aromatic rings), 7.04-7.10 (m, 3H, CH aromatic rings), 7.28-7.31 (m, 2H, CH aromatic rings), 7.47 (m, 3H, CH aromatic rings and piperidine NH.HCl), 7.66-7.69 (m, 3H, CH aromatic rings), 8.45 (d, 1H, CH aromatic rings), 8.81-8.83 (m, 1H, CH aromatic rings), 9.06-9.08 (m, 1H, CH aromatic rings), 9.34-9.36 (m, 1H, NH), 11.28 (bs, 1H, PhCH$_2$N.HCl), 12.70 (bs, 1H, HCl).

N-(1-benzylpiperidin-4-yl)-2-(4-phenylpiperazin-1-yl)-7-((1-(2-(quinolin-4-ylamino)ethyl)piperidin-4-yl)methoxy)quinazolin-4-amine (G)

Prepared according to the general procedure for preparing compounds E and F.

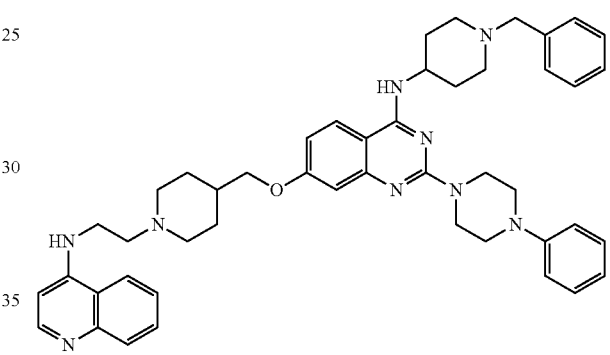

M.p.: 122-124° C. $^1$H-NMR (400 MHz; DMSO) δ 1.34-1.37 (m, 2H, 2×CH piperidine ring), 1.62-1.67 (m, 2H, 2×CH piperidine ring), 1.76-1.79 (m, 3H, 2×CH piperidine ring and OCH$_2$CH), 1.93-1.96 (m, 2H, 2×CH piperidine ring), 2.03-2.11 (m, 4H, 4×CH piperidine ring), 2.62-2.65 (m, 2H, CH$_2$CH$_2$NH-quinoline), 2.86-2.89 (m, 2H, 2×CH piperidine ring), 2.98-3.01 (m, 2H, 2×CH piperidine ring), 3.19 (m, 4H, 2×CH$_2$ piperazine ring), 3.44 (m, 2H, CH$_2$CH$_2$NH-quinoline), 3.50 (s, 2H, NCH$_2$Ph), 3.90 (m, 6H, CH$_2$O and 2×CH$_2$ piperazine ring), 4.04-4.05 (bm, 1H, NHC$_4$—H-piperidine ring), 6.48-6.49 (d, 1H, CH quinoline ring), 6.67-6.70 (m, 2H, CH aromatic rings), 6.78-6.82 (m, 1H, CH aromatic rings), 7.00 (d, 2H, CH aromatic rings), 7.07 (s, 1H, NH quinoline), 7.21-7.27 (m, 3H, CH aromatic rings and NH), 7.33 (m, 4H, CH aromatic rings), 7.45-7.46 (m, 2H, CH aromatic and quinoline ring), 7.59-7.63 (t, 1H, CH quinoline ring), 7.77-7.79 (d, 1H, CH quinoline ring), 7.97-7.99 (d, 1H, CH aromatic rings), 8.15-8.17 (d, 1H, CH quinoline ring), 8.39 (d, 1H, CH quinoline ring).

Example 5: Hydrochlorides of Compounds E, F and G

General Procedure to Obtain the Hydrochloride of the Final Free Amine Compounds E, F, and G.

To a solution of the final free amine compound in dry THF was added HCl 4N in dioxane (15 eq. every salt convertible position) at 0° C. The reaction mixture was then stirred for about 1 h at 0° C. Finally, the white suspension was filtered

Example 6: Compound H

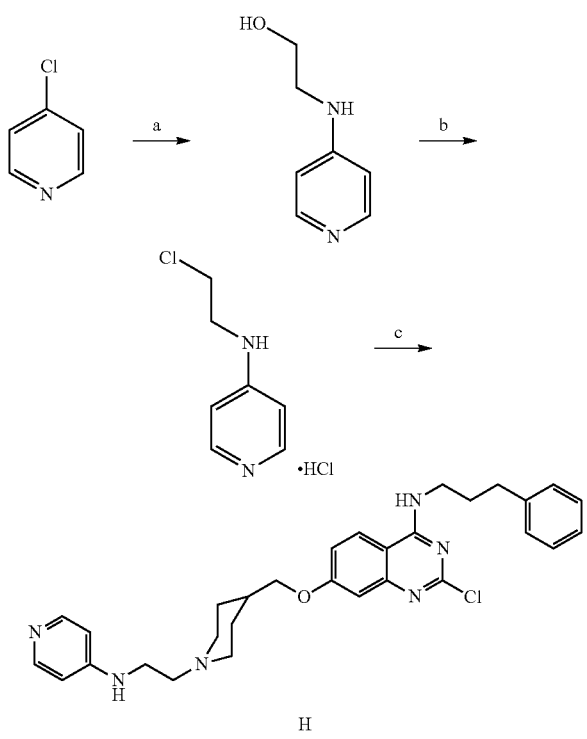

a) Ethanolamine, 125° C., 4 h, quantitative yield. b) SOCl₂, DMF, Flash boiling, quantitative yield. c) 13, K₂CO₃, KI, DMF, 90° C., 12 h, 20%.

4-((2-Hydroxyethyl)amino)pyridine (33)

A mixture of 4-chloropyridine (500 mg; 4.41 mmol) in ethanolamine (2.6 mL; 44 mmol) was stirred at 110° C. for 3 h. The solvent was removed and the residue was purified by silica gel flash chromatography using a linear gradient of ethyl acetate (0→100% AcOEt) in cyclohexane to afford 33 as a white powder (607 mg; 4.40 mmol; quantitative yield).

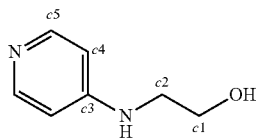

$^1$H NMR (500 MHz, DMSO) δ 8.00 (d, J=6.1 Hz, 1H, Hc5), 6.49 (m, 3H, Hc4 and HNH), 4.77 (brs, 1H, HOH), 3.53 (t, J=6.0 Hz, 2H, Hc1), 3.13 (q, J=5.9 Hz, 2H, Hc2).

$^{13}$C NMR (125 MHz, DMSO) δ: 154.1 (Cc3), 149.7 (Cc5), 107.5 (Cc4), 59.7 (Cc1), 40.6 (Cc2).

HRMS-ESI (m/z) calculated for $C_7H_{10}N_2NaO$ [M+Na]⁺: 161.0685. found: 161.0650.

4-((2-chloroethyl)amino)quinoline hydrochloride (34)

33 (300 mg; 1.92 mmol) was solubilized in thionyl chloride (2 ml). The mixture was flash boiled and the solvent was removed. Toluene was added to remove the residual thionyl chloride by co-evaporation. The residue was triturated in dichloromethane and the solid was filtrated to afford the hydrochloride 34 as a white solid (360 mg; 1.87 mmol; 97%).

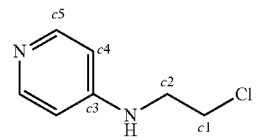

$^1$H NMR (500 MHz, DMSO) δ 8.22 (brs, 1H, HNH), 8.11 (d, J=6.8 Hz, 2H, Hc5), 6.81 (d, J=6.8 Hz, 2H, Hc4), 3.76 (t, J=6.0 Hz, 2H, Hc1), 3.58 (q, J=5.6 Hz, 2H, Hc2).

$^{13}$C NMR (125 MHz, DMSO) δ: 156.6 (Cc3), 143.9 (Cc5), 107.8 (Cc4), 44.1 (Cc1), 43.5 (Cc2).

HRMS-ESI (m/z) calculated for $C_7H_{10}N_2Cl$ [M+H]⁺: 157.0527. found: 157.0541.

1-Chloro-4-(3-phenylpropylamino)-7-((1-(2-(pyridin-4-ylamino)ethyl)piperidin-4-yl)methoxy)quinazoline (Compound H)

To a solution of 13 (15 mg; 36 μmol), K₂CO₃ (10 mg; 72 μmol) and a catalytic amount of KI in DMF (0.5 mL) was added 34 (11 mg; 72 μmol). The mixture was stirred at 65° C. overnight. The mixture was diluted with ethyl acetate. The organic phase was washed with water and brine and dried over sodium sulfate. The solvent was removed and the residue was purified by silica gel flash chromatography using a linear gradient of ammonia 1N in methanol (0→10% MeOH/NH₃) in dichloromethane or by reversed phase HPLC using a linear acetonitrile gradient with 0.01% of TEA (0→80% CH₃CN) to afford Compound H (4.0 mg; 7.5 μmol; 20%) as a white powder.

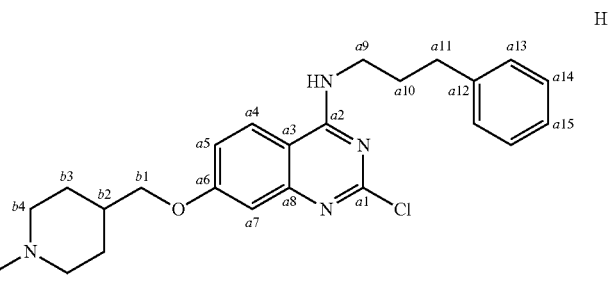

¹H NMR (500 MHz; DMSO) δ 8.55 (m, 1H, HNH), 8.19 (d, J=9.1 Hz, 2H, Hc4), 7.33-7.22 (m, 4H, Ha4, Ha15 and Ha13), 7.22-7.10 (m, 2H, Ha14), 7.02 (d, J=2.5 Hz, 1H, Ha5), 6.57-5.54 (m, 1H, HNH), 6.34 (m, 2H, Hc4), 3.92 (d, J=5.5 Hz, 2H, Hb1), 3.92-3.82 (m, 2H, Ha9), 3.54-355 (m, 2H, Hc2), 3.21-3.10 (m, 2H, Hb4eq), 2.98-2.89 (m, 2H, Ha11), 2.68 (t, J=7.2 Hz, 2H, Hc1), 2.05-1.89 (m, 4H, Ha10 and Hb4ax), 1.86-1.71 (m, 3H, Hb2 and Hb3eq), 1.43-1.41 (m, 2H, Hb3ax).

¹³C NMR (125 MHz, DMSO) δ 162.5 (Ca6), 160.6 (Ca2), 157.4 (Ca1), 153.4 (Cc3), 152.6 (Ca8), 152.3 (Cc5), 141.5 (Ca12), 128.3 (Ca13), 128.2 (Ca14), 125.7 (Ca15), 124.6 (Ca4), 116.9 (Ca5), 107.4 (Ca3), 107.1 (Ca7), 94.7 (Cc4), 72.4 (Cb1), 56.7 (Cc1), 53.0 (Cb4), 40.4 (Ca9), 35.1 (Cb2), 32.4 (Ca11), 31.3 (Ca10), 29.0 (Cb3).

MS-ESI (m/z) calculated for $C_{30}H_{36}ClN_6O$ [M+H]⁺: 421.263. found: 421.265.

II. Biological Tests of the Compounds According to the Invention

DNMT3A Assay.

DNMT3A enzyme inhibition was adapted from the restriction-based fluorescence assay protocol described in Ceccaldi et al. (*ChemBioChem* 2011, 12, 1337-45). Briefly, a 5'-labelled biotin oligonucleotide is hybridized to its complementary strand labelled with 6-carboxyfluorescein at the 3'-end into a 384 well microplate (black Optiplates; Perkin Elmer) pre-coated with avidin. The duplex contains a unique CpG site overlapping with a restriction site of a methylation sensitive restriction enzyme. The human C-terminal DNMT3A (a.a. 623-908), produced as described in Gros et al. (*Nucleic Acids Research* 2013 41(19):e185), was added in each well (200 ng/well) and mixed with the chemical compounds at desired concentrations and freshly prepared AdoMet (20 μM final concentration) to start the reaction in a total volume of 50 μL. After 1 hour incubation at 37° C. each well were washed three times with PBS, Tween-20 0.05%, NaCl (500 mM) and three more times with PBST. Specific fluorescent signals were detected with the methylation-sensitive restriction enzyme HpyCH4IV (NEB) as described and measured on a Perkin Elmer Envision detector. The percentage of inhibition is reported. The formula used to calculate the percentage of inhibition is [(X−Y)/X]×100, where X is the signal determined in the absence of the inhibitor and Y is the signal obtained in the presence of the inhibitor. The concentration at which 50% of efficacy of inhibition is observed (EC50) was determined by analysis of a concentration range of the tested compound in triplicates. The non-linear regression fittings with sigmoidal dose-response (variable slope) were performed with GraphPad Prism 4.03 (GraphPad Software).

DNMT1 Assay.

His-DNMT1 (182 kDa, human) was cloned, expressed and purified as described in Halby et al. (*ChemBioChem* 2012, 13, 157-65). The reaction was performed in a 10 μL total reaction volume in low volume NBS™ 384-well microplates (Corning), containing the tested compound (up to 1% DMSO), 1 μM of a SAM/[methyl-³H] SAM (3 TBq/mmol, PerkinElmer) mix in a ratio of 3-to-1 (isotopic dilution 1*:3), 0.3 μM of biotinylated hemimethylated DNA duplex (5'-GATmCGCmCGATGmCGmCGAATmCGmC-GATmCGATGmCGAT-3' and BIOT-5'-ATCGCATC-GATCGCGATTCGCGCATCGGCGATC-3'), and 90 nM of DNMT1 in methylation buffer (20 mM HEPES pH 7.2, 1 mM EDTA, 50 mM KCl, 25 μg/mL BSA). The reaction was incubated at 37° C. for 2 hours. 8 μL are then transferred into a streptavidin 96-well scintillant coated Flashplate™ (PerkinElmer) containing 190 μL of 20 μM SAH in 50 mM Tris-HCl pH 7.4. The Flashplate™ was agitated at room temperature for 1 hour, washed three times with 200 μL of 0.05% Tween®-20 in 50 mM Tris-HCl pH 7.4, and read in 200 μL of 50 mM Tris-HCl pH 7.4 on TopCount NXT™ (PerkinElmer).

The results of these tests obtained with the compounds of the invention are indicated below:

| | DNMT1 (% of inhibition) | | | DNMT3A (% of inhibition) | | |
|---|---|---|---|---|---|---|
| Compound | 32 μM | 10 μM | $EC_{50}$ μM | 3.2 μM | 1 μM | $EC_{50}$ μM |
| A | 0 | 0 | — | 18 | 0 | ND |
| B | 93 | 5 | 19 | 73 | 0 | ND |
| C | 94 | 0 | 23 | 43 | 0 | ND |
| D | 98 | 35 | 13 | 81 | 52 | ND |
| E | 100 | 59 | 10 | 100 | 74 | 0.6 |
| F | 93 | 45 | 11.7 | 84 | 75 | ND |
| G | 100 | 54 | 10 | 95 | 57 | ND |
| H | — | — | — | 32 | 0 | ND |

Anti-Proliferative Activity. (on KG-1)

KG-1 human leukemia cells were obtained from the ATCC (USA) and cultivated in RPMI 1640 medium (with HEPES and Glutamine, BE12-115F, Lonza, France) supplemented with, respectively, 20% and 15% foetal calf serum (Lonza, France), at 37° C. and under 5% $CO_2$. To measure the anti-proliferative properties of tested molecules, 2×10⁴ cells are seeded at day 0 in a 96 wells plate. The compounds to be tested, stored at −20° C. as 10⁻² M stock solution in 100% DMSO, are freshly diluted on day 1 in RPMI 1640 medium, before adding a dose range of 3.2 nM to 10 μM to the cells. This treatment is repeated on day 2 and 3, and on day 4 cell viability is assessed using the ATPLite™ kit from Perkin (ATPlite™ 1 Step Luminescence Assay System, ref 3016739), following the provider instructions. The raw data are analyzed with GraphPad Prism software (v4.03) to generate $EC_{50}$ values corresponding to the compound concentrations giving 50% reduction in cell viability. The values presented are the mean results of at least two independent experiments. The 95% confidence intervals for these $EC_{50}$ values are also indicated.

Cells were then incubated for 72 h at 37° C. in humidified 5% $CO_2$ atmosphere.

At the end of the experiment, cell viability was evaluated by determining the level of ATP released by viable cells.

$EC_{50}$ values were determined with curve fitting analysis method (non linear regression model with a sigmoid dose response, variable Hill slope coefficient) provided by the Prism Software (GraphPad). Results were expressed as average $EC_{50}$ values (concentration of tested compound that inhibits 50% of the maximum effect for the considered compound).

The results of these tests obtained with the compounds of the invention are indicated below:

| | $EC_{50}$ (μM) | % proliferation inhibition | | | |
|---|---|---|---|---|---|
| Compound | KG-1 | 10 μM | 5 μM | 1 μM | 0.1 μM |
| A | ND | 84.5 | 29.7 | 6.1 | −0.8 |
| B | ND | 99.9 | 95.9 | 3.8 | −1.7 |
| C | ND | 99.7 | 99.1 | 5.7 | −3.1 |
| D | ND | 99.5 | 79.7 | 13.2 | −2.3 |
| E | 2.5 | 99.8 | 92.1 | 15.4 | −2.3 |
| F | ND | 99.9 | 99.6 | 31.9 | 2.0 |
| G | ND | 99.8 | 99.6 | 32.2 | −2.2 |

Gene Expression. (CMV-Luc Reactivation)

KG-1 cell line, stably transfected with the luciferase Firefly (Luc+ from pGL3 by Promega) reporter gene under the control of the CMV promoter (from pEGFP-N1 by Clontech) partially methylated (50%), is seeded at 20,000 cell per well in 96-well plate. After 24 h of incubation in the presence of the compounds or the solvent DMSO, the induction of the promoter is measured by quantification of luciferase with the Brite-lite™ assay system (Perkin Elmer) according to the manufacturer protocol. The luminescence is measured on EnVision™ Multilabel Plate Reader (Perkin Elmer) and the data are expressed in induction factor compared to the DMSO control condition. The mean of 3 experiments and its standard error is reported in the table below.

| Compound | Reactivation fold of luciferase gene reporter Concentration (μM) | | | |
|---|---|---|---|---|
| | 10 | 5 | 1 | 0.1 |
| A | 6.0 ± 0.6 | 4.4 ± 0.5 | 1.2 ± 0.1 | 1.1 ± 0.1 |
| B | 0.0 ± 0.0 | 5.8 ± 1.6 | 1.4 ± 0.0 | 1.1 ± 0.0 |
| C | 0.0 ± 0.0 | 0.1 ± 0.0 | 1.7 ± 0.1 | 1.1 ± 0.0 |
| D | 1.1 ± 1.0 | 12.7 ± 0.6 | 1.7 ± 0.0 | 1.1 ± 0.0 |
| E | 0.0 ± 0.0 | 1.3 ± 1.2 | 3.5 ± 0.0 | 1.1 ± 0.0 |
| F | 0.0 ± 0.0 | 1.0 ± 0.8 | 4.4 ± 0.4 | 1.1 ± 0.0 |
| G | 0.0 ± 0.0 | 0.2 ± 0.1 | 5.3 ± 0.4 | 1.1 ± 0.0 |

The invention claimed is:

1. A compound of the following formula (I):

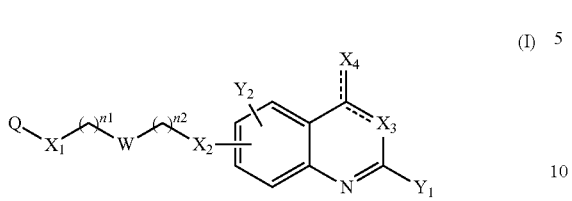

or a pharmaceutically acceptable salt thereof,
wherein:
= represents a single bond or a double bond on the condition that the two bonds = do not represent a double bond at the same time,
n1 and n2 represent, independently of each other, an integer comprised between 0 and 8,
Q represents an optionally substituted aryl or an optionally substituted nitrogen-containing heterocycle,
W represents $NR_0$, a divalent monoglycosyl, a piperidinediyl, a piperazinediyl or a pyrrolidinediyl,
$X_1$ represents O or $NR_1$,
$X_2$ represents O, $NR_2$ or a bond,
$X_3$ represents:
  N when = $X_3$ represents a double bond =$X_3$, and
  $NR_3$ when = $X_3$ represents a single bond —$X_3$,
$X_4$ represents:
  O or $NR_4$ when = $X_4$ represents a double bond =$X_4$, and
  $OR_4$ or $NR_4R_5$ when = $X_4$ represents a single bond —$X_4$,
$Y_1$ and $Y_2$ represent, independently of each other, a halogen atom, $R_{100}$, $OR_{101}$ or $NR_{102}R_{103}$, provided that at least one of $Y_1$ and $Y_2$ represent a group other than H,
$R_0$ represents H; CHO; $CO_2$—(($C_1$-$C_6$)alkyl); or a ($C_1$-$C_6$)alkyl optionally substituted with CHO, $CO_2H$ or $CO_2$—(($C_1$-$C_6$)alkyl),
$R_1$ and $R_2$ represent, independently of each other, H or a ($C_1$-$C_6$)alkyl,
$R_3$ and $R_4$ represent, independently of each other, H, ($C_1$-$C_6$)alkyl, aryl, heterocycle, —(($C_1$-$C_6$)alkyl)-$X_5$-aryl or —(($C_1$-$C_6$)alkyl)-$X_5$-heterocycle,
with $X_5$ representing a bond, O, S or $NR_6$ and each aryl or heterocycle moiety being optionally substituted,
$R_5$ and $R_6$ represent, independently of each other, H or a ($C_1$-$C_6$)alkyl,
$R_{100}$, $R_{101}$, $R_{102}$ and $R_{103}$ represent, independently of one another, H, optionally substituted aryl, optionally substituted heterocycle, or —(($C_1$-$C_6$)alkyl)-$X_6$-$A_1$,
with $X_6$ representing a bond, O, S or $NR_{104}$ and Ai representing H, ($C_1$-$C_6$)alkyl, optionally substituted aryl or optionally substituted heterocycle,
or, for the $R_{102}$ and $R_{103}$ groups, $R_{102}$ and $R_{103}$ form together, with the nitrogen carrying them, an optionally substituted heterocycle, and
$R_{104}$ represents H or a ($C_1$-$C_6$)alkyl.

2. The compound according to claim 1, which is a compound of the following formula (I-3c) or (I-4c):

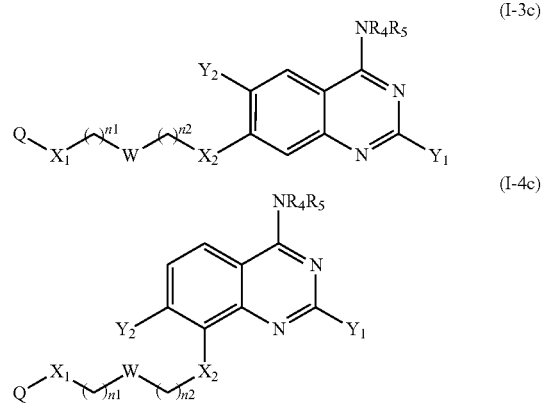

or a pharmaceutically acceptable salt thereof.

3. The compound according to claim 1, wherein:
n1 and n2 represent, independently of each other, an integer comprised between 0 and 4,
$X_1$ represents NH and $X_2$ represents a bond or O, and
W represents

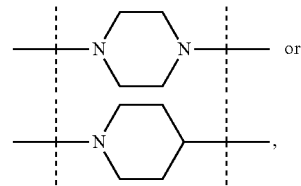

the nitrogen atom being linked to $(CH_2)_{n1}$.

4. The compound according to claim 1, wherein Q represents an aryl or nitrogen-containing heterocycle optionally substituted with one or several groups selected from halogen; oxo (=O); $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; and aryl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$,
with $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ to $R_{40}$ representing, independently of one another, H or ($C_1$-$C_6$)alkyl.

5. The compound according to claim 4, wherein Q represents a cycle of the following formula:

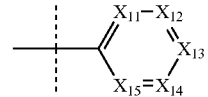

wherein:
$X_{11}$ represents N or $CR_{41}$,
$X_{12}$ represents N or $CR_{42}$,
$X_{13}$ represents N or C—$NR_{43a}R_{43b}$,
$X_{14}$ represents N or $CR_{44}$,
$X_{15}$ represents N or $CR_{45}$,
$R_{43a}$ and $R_{43b}$ each represent, independently of each other, H or ($C_1$-$C_6$)alkyl, $R_{41}$, $R_{42}$, $R_{44}$ and $R_{45}$ each represent, independently of each other, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; or aryl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$, or in the case of $R_{44}$ and $R_{45}$, $R_{44}$ and $R_{45}$ form together a chain of the following formula:

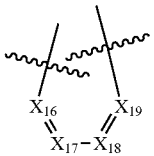

wherein:
$X_{16}$ represents N or $CR_{46}$,
$X_{17}$ represents N or $CR_{47}$,
$X_{18}$ represents N or $CR_{48}$,
$X_{19}$ represents N or $CR_{49}$, and
$R_{46}$, $R_{47}$, $R_{48}$ and $R_{49}$ each represent, independently of one another, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; or aryl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$ on the proviso that no more than three of $X_{11}$, $X_{12}$, $X_{14}$, $X_{15}$, $X_{16}$, $X_{17}$, $X_{18}$ and $X_{19}$ represent N.

6. The compound according to claim 5, wherein Q represents

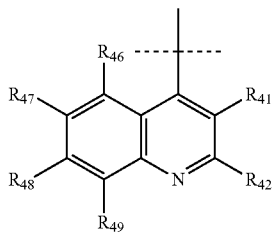

where $R_{41}$, $R_{42}$, $R_{46}$, $R_{47}$, $R_{48}$ and $R_{49}$ each represent, independently of each other, hydrogen, halogen, $OR_{11}$, or $NR_{12}R_{13}$.

7. The compound according to claim 1, wherein $R_3$ and $R_4$ represent, independently of each other, H, $(C_1-C_6)$alkyl, aryl, heterocycle, —$((C_1-C_6)$alkyl$)$-$X_5$-aryl or —$((C_1-C_6)$alkyl$)$-$X_5$-heterocycle, each aryl or heterocycle moiety being optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, with $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ to $R_{40}$ and $R_{50}$, $R_{51}$, $R_{52}$, $R_{53}$, $R_{54}$, $R_{55}$, $R_{56}$, $R_{57}$, $R_{58}$, $R_{59}$, $R_{60}$ to $R_{61}$ representing, independently of one another, H or $(C_1-C_6)$alkyl.

8. The compound according to claim 7, wherein $R_3$ and $R_4$ represent, independently of each other, H, $(C_1-C_6)$alkyl, aryl, heterocycle, —$((C_1-C_6)$alkyl$)$-$X_5$-aryl or —$((C_1-C_6)$alkyl$)$-$X_5$-heterocycle each aryl or heterocycle moiety being optionally substituted with one or several groups selected from halogen; $OR_{11}$; $NR_{12}R_{13}$; $(C_1-C_6)$alkyl optionally substituted with one or several groups selected from halogen, $OR_{21}$ and $NR_{22}R_{23}$; and aryl or aryl-$(C_1-C_6)$alkyl optionally substituted with one or several groups selected from halogen, $OR_{31}$ and $NR_{32}R_{33}$.

9. The compound according to claim 1, wherein $Y_1$ and $Y_2$ represent, independently of each other, H, a halogen atom, $OR_{101}$ or $NR_{102}R_{103}$, provided that at least one of $Y_1$ and $Y_2$ represent a group other than H, where $R_{101}$, $R_{102}$ and $R_{103}$ represent, independently of one another, H, optionally substituted aryl, optionally substituted heterocycle, or —$((C_1-C_6)$alkyl$)$-$X_6$-$A_1$, with $X_6$ representing a bond, O or $NR_{104}$, and $A_1$ representing H, $(C_1-C_6)$alkyl, optionally substituted aryl or optionally substituted heterocycle, or, for the $R_{102}$ and $R_{103}$ groups, $R_{102}$ and $R_{103}$ form together, with the nitrogen carrying them, an optionally substituted heterocycle, and where the optionally substituted aryl and optionally substituted heterocycle are optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, with $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ to $R_{40}$ and $R_{50}$, $R_{51}$, $R_{52}$, $R_{53}$, $R_{54}$, $R_{55}$, $R_{56}$, $R_{57}$, $R_{58}$, $R_{59}$, $R_{60}$ to $R_{61}$ representing, independently of one another, H or $(C_1-C_6)$alkyl.

10. The compound according to claim 9, wherein $Y_1$ represents H, a halogen atom or $NR_{102}R_{103}$, and $Y_2$ represents H or $OR_{101}$, provided that at least one of $Y_1$ and $Y_2$ represent a group other than H, with $R_{101}$ representing H, $(C_1-C_6)$alkyl, aryl, aryl-$(C_1-C_6)$alkyl or $(C_1-C_6)$alkyl-aryl, and $R_{102}$ and $R_{103}$ representing, independently of one another, H, $(C_1-C_6)$alkyl, aryl, heterocycle, aryl-$(C_1-C_6)$alkyl, heterocycle-$(C_1-C_6)$alkyl or —$((C_1-C_6)$alkyl$)$-$NR_{104}$-$A_1$, with $A_1$ representing H, $(C_1-C_6)$alkyl, aryl or heterocycle, or $R_{102}$ and $R_{103}$ forming together, with the nitrogen carrying them, a heterocycle, and where each aryl and heterocycle moiety is optionally substituted with one or several groups selected from halogen, oxo (=O), $(C_1-C_6)$alkyl, aryl, and aryl-$(C_1-C_6)$alkyl.

11. The compound according to claim 1, which is selected from the following compounds:

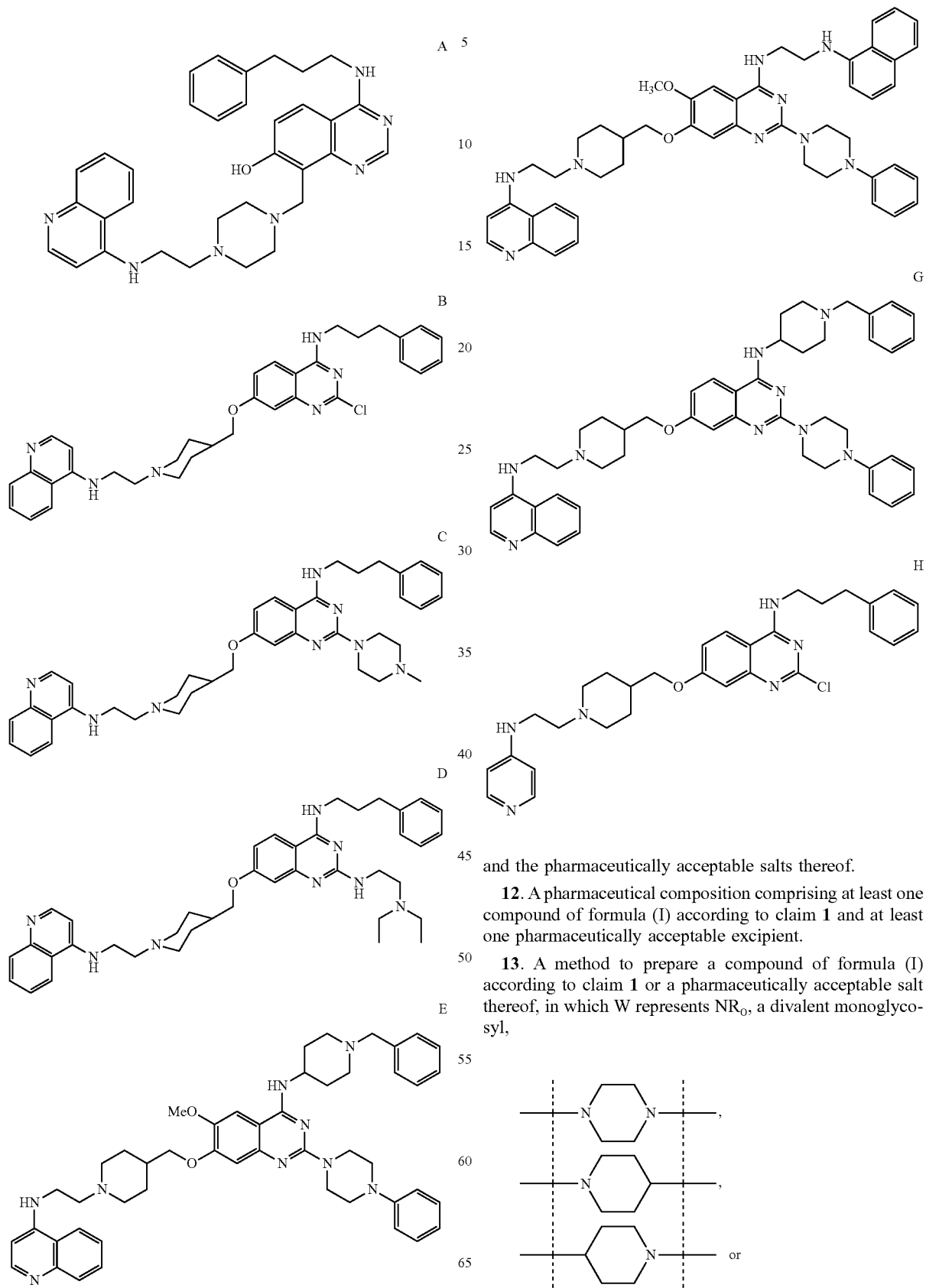

and the pharmaceutically acceptable salts thereof.

12. A pharmaceutical composition comprising at least one compound of formula (I) according to claim 1 and at least one pharmaceutically acceptable excipient.

13. A method to prepare a compound of formula (I) according to claim 1 or a pharmaceutically acceptable salt thereof, in which W represents $NR_0$, a divalent monoglycosyl, -continued

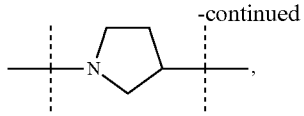

comprising:
(1) reacting a compound of the following formula (II):

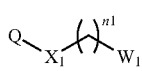
(II)

in which Q, $X_1$ and n1 are as defined in claim 1 and $W_1$ represents $LG_1$, $NHR_8$, a monovalent monoglycosyl,

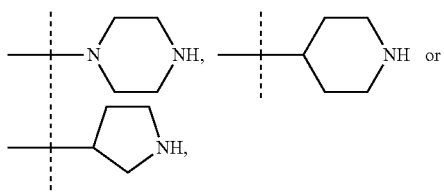

with a compound of the following formula (III):

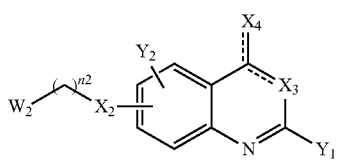
(III)

in which $X_2$, $X_3$, $X_4$, $Y_1$, $Y_2$ and n2 are as defined in claim 1 and $W_2$ represents $LG_2$, $NHR_8$, a monovalent monoglycosyl, or

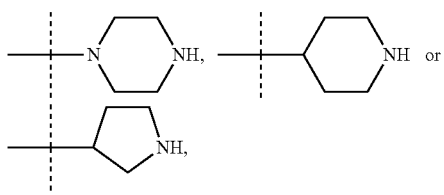

wherein $LG_1$ and $LG_2$ represent, independently of each other, a leaving group and $R_8$ represents $R_0$ as defined in claim 1 or a N-protecting group,
on the condition that:
when $W_1$ represents $LG_1$, then $W_2$ represents $NHR_8$, a monovalent monoglycosyl,

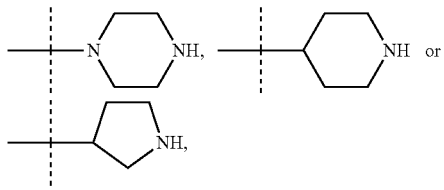

and
when $W_1$ represents $NHR_8$, a monovalent monoglycosyl,

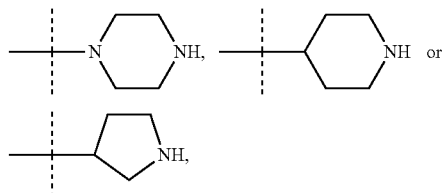

then $W_2$ represents $LG_2$, and, when $W_1$ or $W_2$ represents $NHR_8$ with $R_8$ representing a N-protecting group, deprotecting the nitrogen atom bearing the N-protecting group,
to give a compound of formula (I) as defined in claim 1 in which W represents $NR_0$, a divalent monoglycosyl,

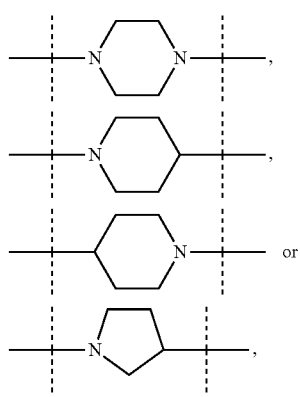

and
(2) optionally salifying or solvating the compound obtained in step (1) to give a pharmaceutically acceptable salt of a compound of formula (I) as defined in claim 1 in which W represents $NR_0$, a divalent monoglycosyl,

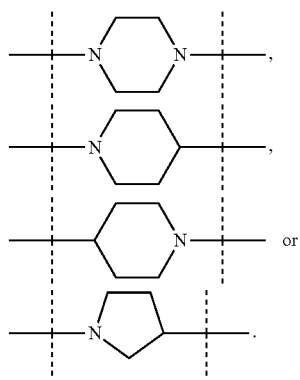

14. A method to prepare a compound of formula (I) according to claim 1, in which at least one of $Y_1$ and $Y_2$ represents a $OR_{101}$ or $NR_{102}R_{103}$ group, or a pharmaceutically acceptable salt thereof, comprising:

(i) reacting a compound of the following formula (XI):

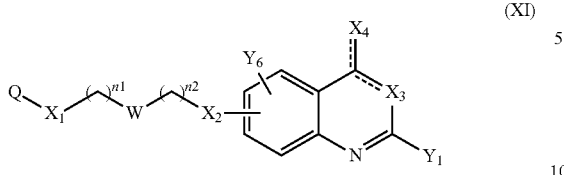

in which $Y_5$ represents $Y_1$ as defined in claim 1, and $Y_6$ represents $Y_2$ as defined in claim 1, provided that at least one of $Y_5$ and $Y_6$ represents a halogen atom, with $HOR_{101}$ or $HNR_{102}R_{103}$, to give a compound of formula (I) as defined in claim 1 in which at least one of $Y_1$ and $Y_2$ represents a $OR_{101}$ or $NR_{102}R_{103}$ group, and (ii) optionally salifying or solvating the compound obtained in step (i) to give a pharmaceutically acceptable salt of a compound of formula (I) as defined in claim 1 in which at least one of $Y_1$ and $Y_2$ represents a $OR_{101}$ or $NR_{102}R_{103}$ group.

15. The compound according to claim 3, wherein:
n1 and n2 represent, independently of each other, 1 or 2,
$X_2$ represents O, and
W represents

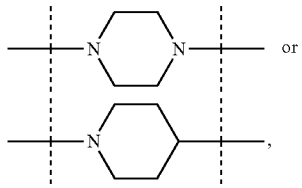

the nitrogen atom being linked to $(CH_2)_{n1}$.

16. The compound according to claim 5, wherein:
$X_{11}$ represents $CR_{41}$,
$X_{12}$ represents $CR_{42}$,
$X_{13}$ represents N or C—$NR_{43a}R_{43b}$,
$X_{14}$ represents $CR_{44}$,
$X_{15}$ represents $CR_{45}$,
$R_{41}$, $R_{42}$, $R_{44}$ and $R_{45}$ each represent, independently of each other, hydrogen; halogen; $OR_{11}$; $NR_{12}R_{13}$; ($C_1$-$C_6$)alkyl optionally substituted with one or several groups selected from halogen, $OR_{21}$, and $NR_{22}R_{23}$; or aryl optionally substituted with one or several groups selected from halogen, $OR_{31}$, and $NR_{32}R_{33}$, or
in the case of $R_{44}$ and $R_{45}$, $R_{44}$ and $R_{45}$ form together a chain of the following formula:

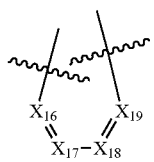

wherein:
$X_{16}$ represents $CR_{46}$,
$X_{17}$ represents $CR_{47}$,
$X_{18}$ represents $CR_{48}$,
$X_{19}$ represents $CR_{49}$, and
$R_{46}$, $R_{47}$, $R_{48}$ and $R_{49}$ each represent, independently of one another, hydrogen; halogen; $OR_{11}$; $NR_{12}R_{13}$; ($C_1$-$C_6$)alkyl optionally substituted with one or several groups selected from halogen, $OR_{21}$, and $NR_{22}R_{23}$; or aryl optionally substituted with one or several groups selected from halogen, $OR_{31}$, and $NR_{32}R_{33}$.

17. The compound according to claim 6, wherein Q represents

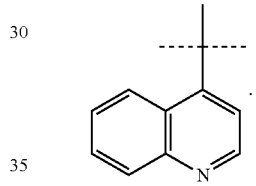

18. The compound according to claim 8, wherein $R_3$ and $R_4$ represent, independently of each other, aryl, heterocycle, aryl-($C_1$-$C_6$)alkyl, heterocycle-($C_1$-$C_6$)alkyl, —(($C_1$-$C_6$)alkyl)-NH-aryl or —(($C_1$-$C_6$)alkyl)-NH-heterocycle,
each aryl or heterocycle moiety being optionally substituted with one or several groups selected from halogen; $OR_{11}$; $NR_{12}R_{13}$; ($C_1$-$C_6$)alkyl optionally substituted with one or several groups selected from halogen, $OR_{21}$ and $NR_{22}R_{23}$; and aryl or aryl-($C_1$-$C_6$)alkyl optionally substituted with one or several groups selected from halogen, $OR_{31}$ and $NR_{32}R_{33}$.

* * * * *

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: DNA duplex
<220> FEATURE:
<221> NAME/KEY: modified_base
<222> LOCATION: (4)..(4)
<223> OTHER INFORMATION: methylCys
<220> FEATURE:
<221> NAME/KEY: modified_base
<222> LOCATION: (7)..(7)
<223> OTHER INFORMATION: methylCys
<220> FEATURE:
<221> NAME/KEY: modified_base
<222> LOCATION: (12)..(12)
<223> OTHER INFORMATION: methylCys
<220> FEATURE:
<221> NAME/KEY: modified_base
<222> LOCATION: (14)..(14)
<223> OTHER INFORMATION: methylCys
<220> FEATURE:
<221> NAME/KEY: modified_base
<222> LOCATION: (19)..(19)
<223> OTHER INFORMATION: methylCys
<220> FEATURE:
<221> NAME/KEY: modified_base
<222> LOCATION: (21)..(21)
<223> OTHER INFORMATION: methylCys
<220> FEATURE:
<221> NAME/KEY: modified_base
<222> LOCATION: (25)..(25)
<223> OTHER INFORMATION: methylCys
<220> FEATURE:
<221> NAME/KEY: modified_base
<222> LOCATION: (30)..(30)
<223> OTHER INFORMATION: methylCys

<400> SEQUENCE: 1
gatcgccgat gcgcgaatcg cgatcgatgc gat                               33

<210> SEQ ID NO 2
<211> LENGTH: 33
<212> TYPE: DNA
<213> ORGANISM: Artificial Sequence
<220> FEATURE:
<223> OTHER INFORMATION: DNA duplex
<220> FEATURE:
<221> NAME/KEY: misc_binding
<222> LOCATION: (1)..(1)
<223> OTHER INFORMATION: Biotinylation

<400> SEQUENCE: 2
atcgcatcga tcgcgattcg cgcatcggcg atc                               33
```